(12) United States Patent
Rapacki et al.

(10) Patent No.: US 11,712,370 B2
(45) Date of Patent: *Aug. 1, 2023

(54) LACRIMAL IMPLANTS AND RELATED METHODS

(71) Applicant: Mati Therapeutics Inc., Austin, TX (US)

(72) Inventors: Alan R. Rapacki, Redwood City, CA (US); Valery Rubinchik, Richmond (CA); Charles Richard Kjellbotn, Parksville (CA)

(73) Assignee: Mati Therapeutics Inc., Austin, TX (US)

( * ) Notice: Subject to any disclaimer, the term of this patent is extended or adjusted under 35 U.S.C. 154(b) by 359 days.

This patent is subject to a terminal disclaimer.

(21) Appl. No.: 16/361,046

(22) Filed: Mar. 21, 2019

(65) Prior Publication Data

US 2019/0216646 A1 Jul. 18, 2019

Related U.S. Application Data

(62) Division of application No. 12/710,855, filed on Feb. 23, 2010, now Pat. No. 10,238,535.

(51) Int. Cl.
*A61F 9/007* (2006.01)
*A61K 9/00* (2006.01)

(52) U.S. Cl.
CPC ........ *A61F 9/00772* (2013.01); *A61K 9/0051* (2013.01); *A61F 2250/0003* (2013.01)

(58) Field of Classification Search
CPC ......... A61F 9/00772; A61F 2250/0003; A61K 9/0051
See application file for complete search history.

(56) References Cited

U.S. PATENT DOCUMENTS 3,923,939 A * 12/1975 Baker ................. A61K 9/0039
264/49
6,196,993 B1 * 3/2001 Cohan ................. A61F 9/0017
604/891.1

(Continued)

OTHER PUBLICATIONS

Final Written Decision in IPR 2019-00448 U.S. Pat. No. 9,849,082; dated Jun. 18, 2020.

*Primary Examiner* — Ariana Zimbouski
(74) *Attorney, Agent, or Firm* — Koren Anderson

(57) ABSTRACT

Lacrimal implants and related methods providing secure, wedgable retention within a lacrimal punctum and associated canaliculus of an eye are disclosed. The lacrimal implants can comprise an implant body configured for at least partial insertion through the lacrimal punctum and into the canaliculus. The implant body can include first and second portions, and can extend from a proximal end of the first portion defining a longitudinal proximal axis to a distal end of the second portion defining a longitudinal distal axis. The implant body can be configured such that, when implanted using an integral dilator, an angled intersection exists between the proximal and distal axes. In this way, at least a portion of the implant body can be biased against at least a portion of the lacrimal canaliculus located at or more distal to a canalicular curvature, thereby retaining an implanted position of the lacrimal implant using anatomical structures.

20 Claims, 37 Drawing Sheets

(56) References Cited

U.S. PATENT DOCUMENTS

| | | | | |
|---|---|---|---|---|
| 6,629,533 | B1* | 10/2003 | Webb | A61B 17/12022 |
| | | | | 128/887 |
| 8,333,726 | B2* | 12/2012 | Rapacki | A61F 9/00772 |
| | | | | 604/8 |
| 8,702,643 | B2* | 4/2014 | Rapacki | A61F 9/0017 |
| | | | | 604/9 |
| 9,763,824 | B2* | 9/2017 | Rapacki | A61F 9/00772 |
| 10,238,535 | B2* | 3/2019 | Rapacki | A61K 9/0051 |
| 2006/0020253 | A1* | 1/2006 | Prescott | A61F 9/00772 |
| | | | | 604/500 |
| 2007/0092570 | A1* | 4/2007 | Missel | A61K 9/0051 |
| | | | | 424/473 |
| 2007/0243230 | A1* | 10/2007 | de Juan | A61L 31/16 |
| | | | | 424/427 |
| 2008/0181930 | A1* | 7/2008 | Rodstrom | A61F 9/00781 |
| | | | | 424/427 |
| 2010/0274204 | A1* | 10/2010 | Rapacki | A61F 9/00772 |
| | | | | 604/285 |

* cited by examiner

SECTION 3B-3B

SECTION 6B-6B

SECTION 7B-7B

SECTION 8B-8B

SECTION 10B-10B

SECTION 42B-42B

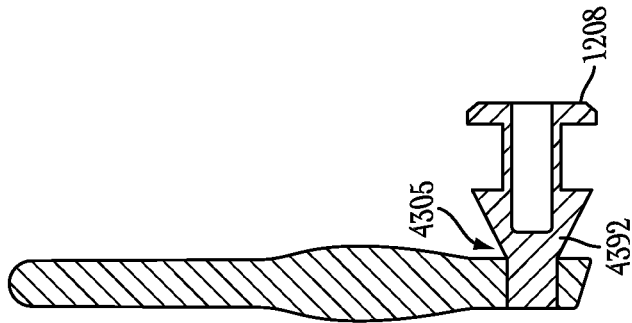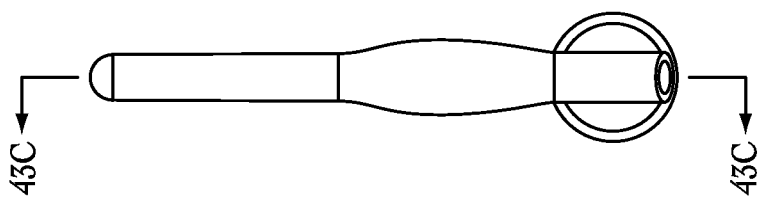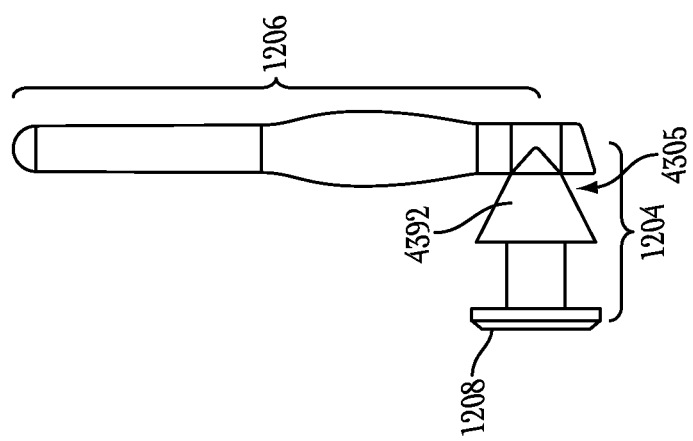

SECTION 44B-44B

SECTION 45B-45B

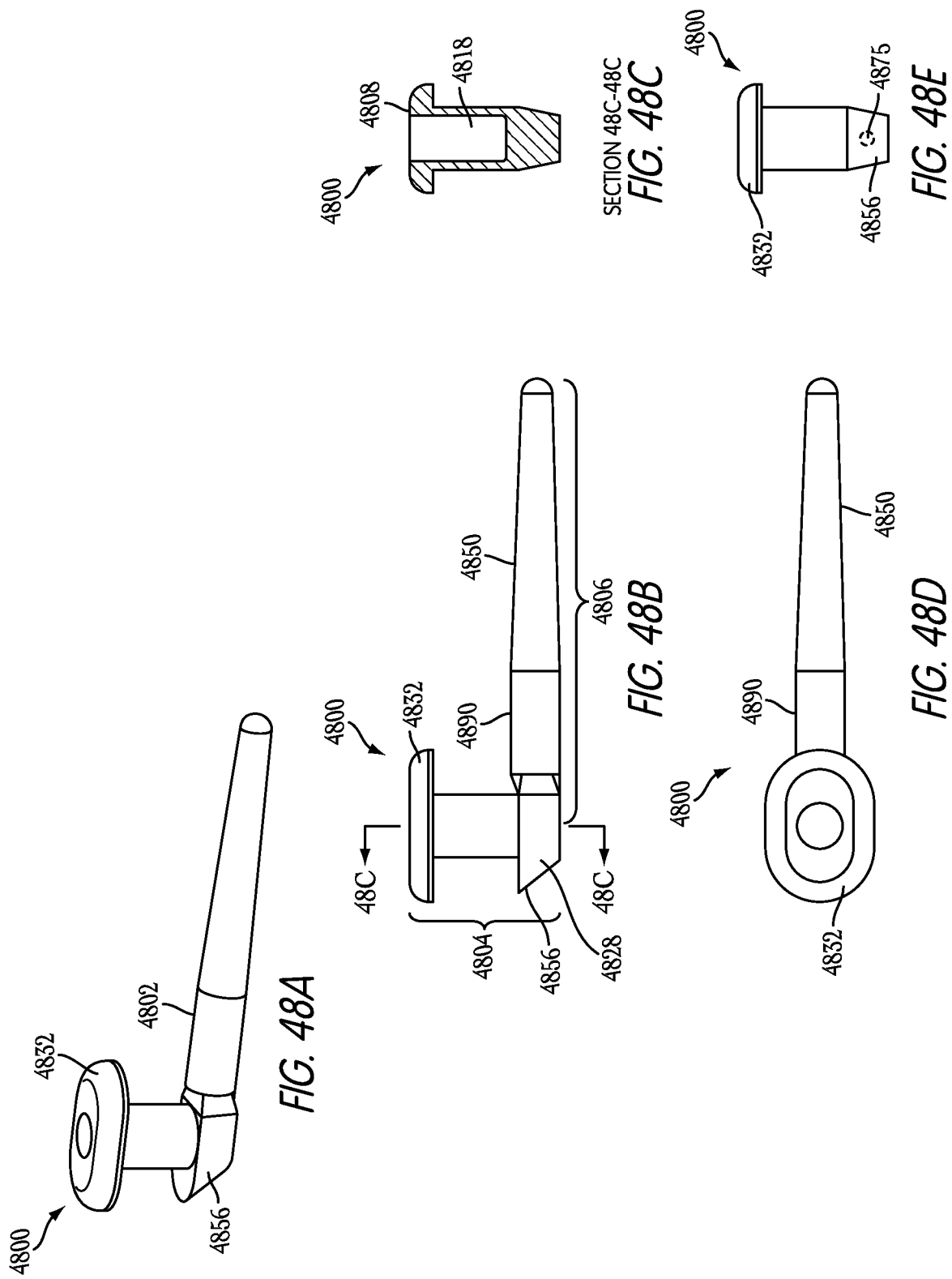

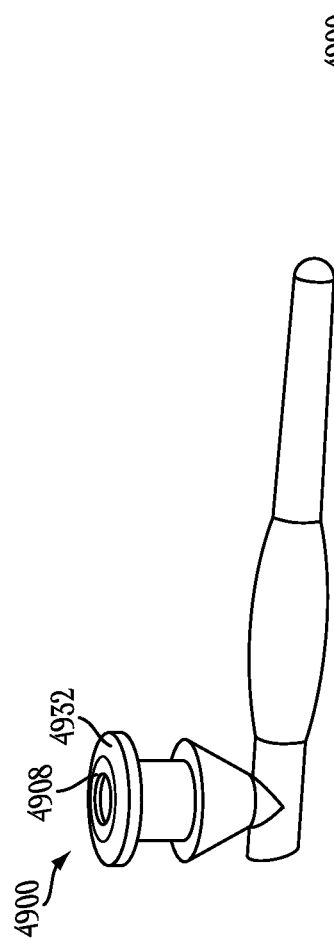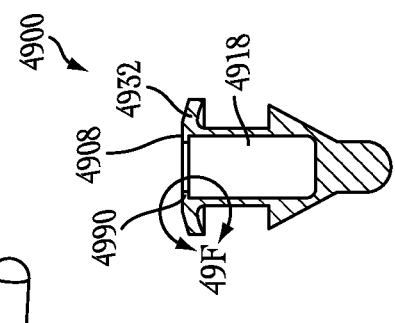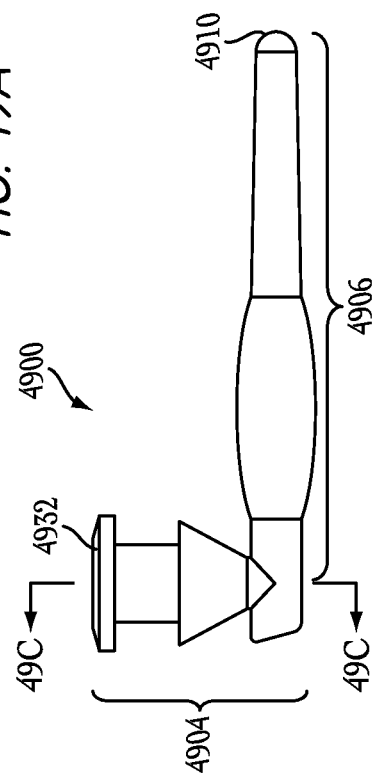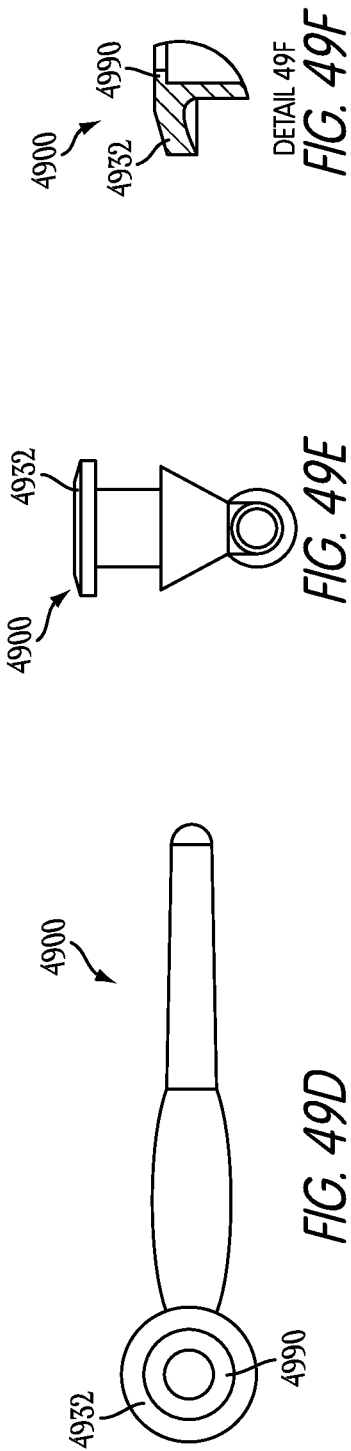

SECTION 50B-50B

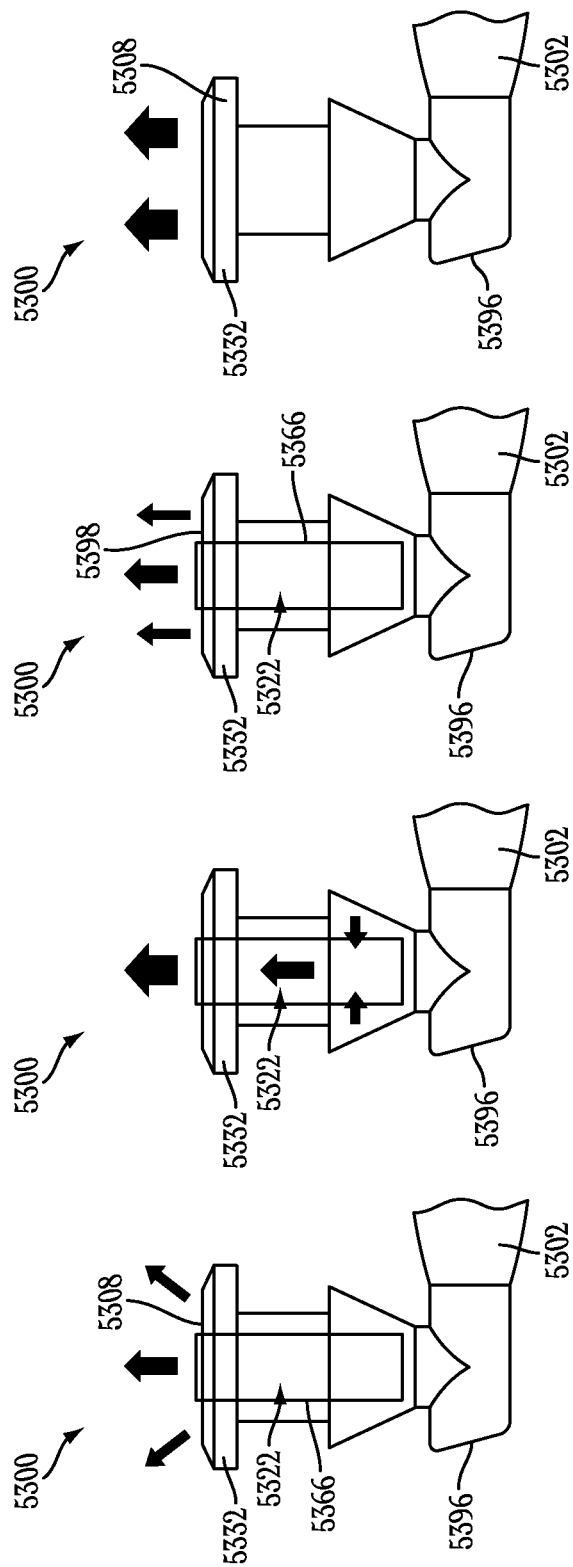

LACRIMAL IMPLANTS AND RELATED METHODS

CROSS REFERENCES TO RELATED APPLICATIONS

This patent application claims the benefit of priority from U.S. Provisional Patent Application Ser. No. 61/154,693, filed Feb. 23, 2009, entitled "LACRIMAL IMPLANTS AND RELATED METHODS," 61/209,036, filed Mar. 2, 2009, entitled "LACRIMAL IMPLANTS AND RELATED METHODS," 61/209,630, filed Mar. 9, 2009, entitled "LACRIMAL IMPLANTS AND RELATED METHODS," 61/271,862, filed Jul. 27, 2009, entitled "LACRIMAL IMPLANTS AND RELATED METHODS," and 61/252,057, filed Oct. 15, 2009, entitled "LACRIMAL IMPLANTS AND RELATED METHODS," all of which are pending and all of which are incorporated herein by reference in their entireties.

This patent application is related to U.S. patent application Ser. No. 12/231,989 filed Sep. 5, 2008, entitled "LACRIMAL IMPLANTS AND RELATED METHODS," which is pending.

TECHNICAL FIELD

This patent document pertains generally to ophthalmic devices, and particularly to ocular implants. More particularly, but not by way of limitation, this patent document pertains to lacrimal implants, methods of making such implants, and methods of treating ocular, respiration, inner ear or other diseases or disorders (e.g., pulmonary or immunological disorders) using such implants.

BACKGROUND

Dry eye, including keratoconjunctivitis sicca, is a common ocular condition that can require therapy. Dry eye has been experienced by a broad demographic band, and is common in elderly individuals. A variety of current treatment modalities target physiological conditions that contribute to dry eye, including augmentation of normal tear fluid, enhancement of tear film component production, and methods to enhance the residence time of tears, such as blocking the tear flow from an eye into and through a lacrimal canaliculus.

Many current tear flow blockage techniques have drawbacks, including being irreversible in nature. For instance, some tear flow blockage techniques involve closing a canalicular canal by stitching the associated punctal opening shut or by using electrical or laser cauterization to seal the punctal opening. Although such procedures can provide the desired result of blocking tear flow to treat dry eye, they are not reversible without reconstructive surgery.

In addition to dry eye symptom relief, a variety of challenges face patients and physicians in the area of ocular, respiration and inner ear disease or disorder management, including adequate drug or other therapeutic agent delivery to the eyes, nasal passage or inner ear. In ocular management, for example, many current ocular drug delivery systems require repetitive manual administration and are often ineffective due to a lack of patient compliance or inadequate drug concentrations reaching the eye. For instance, when an eye drop is instilled in an eye, it often overfills the conjunctival sac (i.e., the pocket between the eye and the lids) causing a substantial portion of the drop to be lost due to overflow of the lid margin and spillage onto the cheek. A large portion of the drop remaining on the ocular surface can be washed away into and through a lacrimal canaliculus shortly after application, thereby diluting the concentration of the drug before it can absorbingly treat the eye. Moreover, topically applied drugs often have a peak ocular effect for about two hours post-application, after which additional applications of the drugs should be, but are often not, administered to maintain the desired drug therapeutic benefit.

In a field different from ocular management, control of respiration-related (e.g., allergies) and inner ear diseases or disorders often requires repetitive manual digestion or other intake of a medication (e.g., drugs or other therapeutic agents), and can be ineffective due to a lack of patient compliance or non-localized drug delivery.

EXEMPLARY ASPECTS AND EMBODIMENTS OF THE INVENTION

The present inventors have recognized various promising techniques to increase the residence time of tears on an eye and delivery of drug or other therapeutic agent to the eye, nasal passage, inner ear or other bodily system. These techniques can include placing a removable, and optionally drug releasing, lacrimal implant through a lacrimal punctum and into the associated canaliculus. It is believed that by designing lacrimal implants that utilize the features of the nasolacrimal drainage system (e.g., by mimicking the shape of the lacrimal canaliculus), patient comfort and implant retention in the ocular anatomy can be satisfied. In this way, the present lacrimal implants can overcome some of the drawbacks associated with current dry eye relief, such as being irreversible in nature, and manual drop or digestion-based drug administration, such as poor patient compliance, waste, untimely application, or non-localized delivery.

Further yet, the present inventors have recognized that a lacrimal implant can benefit from one or more of: the ability to be easily implanted and removed without much biasing of the lacrimal punctum or associated canaliculus, the ability to be securely retainable in the lacrimal canaliculus upon implantation, optionally without being pre-sized to a particular lacrimal punctum or canaliculus diameter, the ability to permit tear fluid, drug or other agent to flow into the nasolacrimal system, and, when made and used as a drug delivery system, the ability to allow for the sustained, localized release of one or more drugs or other therapeutic agents at a desired therapeutic level for an extended period of time.

In light of these recognitions, lacrimal implants for treating diseases or disorders are disclosed. More particularly, lacrimal implants, methods of making such implants, and methods of treating ocular, respiration, inner ear, pulmonary or immunological diseases or disorders using such implants are disclosed. Clinical trials to evaluate the safety, tolerability, comfort, ease of handling, insertion and removal, retention, efficacy and dosing of the various lacrimal implants disclosed in this patent document indicate that the lacrimal implants, such as the lacrimal implants shown in FIGS. 12, 13 and 43A-43C, are effective and well tolerated by clinical test patients. In addition, retention rates of certain lacrimal implants, such as the lacrimal implants of the type shown in FIG. 13 have been found to be about 60% or higher at 8 weeks, and about 47% percent or higher at 12 weeks, while retention rates of other lacrimal implants, such as the type those shown in FIGS. 12 and 43A-C, have been found to be about 75% or higher after eight weeks.

To better illustrate the subject matter described herein, a non-limiting list of exemplary aspects and embodiments is provided here:

1. A lacrimal implant insertable into a lacrimal canaliculus, comprising: an implant body, including first and second portions, the implant body extending from a proximal end of the first portion to a distal end of the second portion; the proximal end of the first portion defining a longitudinal proximal axis and including a retainment projection laterally protruding non-equidistantly around its circumference; the distal end of the second portion defining a longitudinal distal axis; and the implant body configured such that, when implanted in the lacrimal canaliculus, an angled intersection exists between the proximal axis and the distal axis for biasing at least a portion of the implant body against at least a portion of the lacrimal canaliculus located at or more distal to a canalicular curvature.

2. The lacrimal implant according to aspect 1, wherein a proximal end of the retainment projection of the first portion laterally protrudes outward in a non-equal lateral distance about its circumference and tapers down to an outer diameter of a distal end of the first portion.

3. The lacrimal implant according to aspect 2, comprising a graspable projection extending at least partially from the proximal end of the first portion, the graspable projection configured to seat against or near a lacrimal punctum when the implant body is implanted; and wherein the proximal end of the retainment projection of the first portion includes a perimeter numerically about equal to a perimeter of the graspable projection.

4. The lacrimal implant according to any of aspects 2 or 3, wherein the proximal end of the retainment projection of the first portion protrudes outward in opposite directions on opposing first and second sides without protruding outwardly from the outer diameter on opposing third and fourth sides.

5. The lacrimal implant according to any of aspects 1-4, further comprising one or more therapeutic agents.

6. The lacrimal implant according to aspect 5, wherein the one or more therapeutic agents are provided in a drug insert at least partially positioned in the first portion, the drug insert configured to deliver a sustained release of the one or more therapeutic agents.

7. A kit comprising the lacrimal implant according to any of aspects 1-6, and an instruction for using the lacrimal implant to treat an eye disorder.

8. A lacrimal implant insertable into a lacrimal canaliculus, comprising: an implant body, including first and second portions, the implant body extending from a proximal end of the first portion to a distal end of the second portion; the proximal end of the first portion defining a longitudinal proximal axis; the distal end of the second portion defining a longitudinal distal axis and including a retainment projection laterally protruding around its circumference, the retainment projection including an outward lateral step at one of a proximal end of the retainment projection or a distal end of the retainment projection; and the implant body configured such that, when implanted in the lacrimal canaliculus, an angled intersection exists between the proximal axis and the distal axis for biasing at least a portion of the implant body against at least a portion of the lacrimal canaliculus located at or more distal to a canalicular curvature.

9. The lacrimal implant according to aspect 8, wherein the lateral step extends laterally outward in a direction perpendicular from a direction in which the second portion extends, the lateral step being greater than or equal to about 0.14 mm.

10. The lacrimal implant according to any of aspects 8 or 9, wherein the lateral step is positioned at the proximal end of the retainment projection and tapers toward an outer diameter of the second portion at the distal end of the retainment projection.

11. The lacrimal implant according to aspect 10, wherein the distal end of the retainment projection includes an integral dilator to facilitate implantation of the implant body into the lacrimal canaliculus.

12. The lacrimal implant according to any of aspects 8-11, further comprising one or more therapeutic agents.

13. The lacrimal implant according to aspect 12, wherein the one or more therapeutic agents are provided in a drug insert at least partially positioned in the first portion, the drug insert configured to deliver a sustained release of the one or more therapeutic agents.

14. The lacrimal implant according to aspect 13, wherein the drug insert comprises at least about 44 micrograms of the one or more therapeutic agents.

15. The lacrimal implant according to aspect 13, wherein the drug insert comprises at least about 81 micrograms of the one or more therapeutic agents.

16. A kit comprising the lacrimal implant according to any of aspects 8-15, and an instruction for using the lacrimal implant to treat an eye disorder.

17. A lacrimal implant for insertion into a lacrimal canaliculus, comprising: an implant body non-linearly extending from a proximal end portion positionable within a vertical section of the lacrimal canaliculus to a distal end portion positionable within a horizontal section of the lacrimal canaliculus and having an intermediate portion therebetween; the intermediate portion partially extending in a first direction toward the proximal end portion and partially extending in a second direction toward the distal end portion such that, when implanted in the lacrimal canaliculus; and wherein the intermediate portion includes a recess storing an expandable material, the expandable material configured for partially expanding in a third direction, substantially opposite the second direction, toward a lacrimal canaliculus ampulla when the implant body is implanted.

18. The lacrimal implant according to aspect 17, wherein the expandable material includes hydrogel.

19. The lacrimal implant according to any of aspects 17 or 18, wherein the expandable material partially expands laterally, relative to the second direction, when the implant body is implanted, the lateral expansion urging one or more surrounding portions of the implant body outward against a wall of the lacrimal canaliculus.

20. The lacrimal implant according to any of aspects 17-19, wherein at least one of the proximal end portion or the distal end portion comprises at least one intermediately-disposed retainment projection having a cross-sectional size greater than an adjacent implant body portion.

21. The lacrimal implant according to any of aspects 17-20, further comprising one or more therapeutic agents.

22. The lacrimal implant according to aspect 21, wherein the one or more therapeutic agents are provided in a drug insert at least partially positioned in the proximal end portion, the drug insert including at least one exposed surface configured to deliver a sustained release of the one or more therapeutic agents.

23. A kit comprising the lacrimal implant according to any of aspects 17-22, and an instruction for using the lacrimal implant to treat an eye disorder.

24. A lacrimal implant insertable into a lacrimal canaliculus, comprising: an implant body, including first and second portions, the implant body extending from a proximal end of the first portion to a distal end of the second portion; the proximal end of the first portion defining a longitudinal proximal axis and including a retainment projection laterally protruding around its circumference; the distal end of the second portion defining a longitudinal distal axis; the retainment projection including an outward lateral step at a proximal end thereof and tapering directly into the second portion; and the implant body configured such that, when implanted in the lacrimal canaliculus, an angled intersection exists between the proximal axis and the distal axis for biasing at least a portion of the implant body against at least a portion of the lacrimal canaliculus located at or more distal to a canalicular curvature.

25. The lacrimal implant according to aspect 24, wherein a length of the retention projection is about 0.96 mm or more.

26. The lacrimal implant according to any of aspects 24 or 25, wherein a distal end of the retainment projection includes an integral dilator to facilitate implantation of the implant body into the lacrimal canaliculus.

27. The lacrimal implant according to any of aspects 24-26, further comprising one or more therapeutic agents.

28. The lacrimal implant according to aspect 27, wherein the one or more therapeutic agents are provided in a drug insert at least partially positioned in the first portion, the drug insert configured to deliver a sustained release of the one or more therapeutic agents.

29. The lacrimal implant according to aspect 28, wherein the drug insert is positioned within a first cavity of the first portion, the first cavity having a diameter at least about 0.56 mm.

30. The lacrimal implant of to any of aspects 28 or 29, wherein the drug insert comprises at least about 81 micrograms of the one or more therapeutic agents.

31. A kit comprising the lacrimal implant according to any of aspects 24-28, and an instruction for using the lacrimal implant to treat an eye disorder.

32. A lacrimal implant insertable into a lacrimal canaliculus, comprising: an implant body non-linearly extending from a proximal end portion positionable within a vertical section of the lacrimal canaliculus to a distal end portion positionable within a horizontal section of the lacrimal canaliculus and having an intermediate portion; the intermediate portion partially extending in a first direction toward the proximal end portion and partially extending in a second direction, in a generally narrowing manner, toward the distal end portion such that when implanted in the lacrimal canaliculus, the implant body directionally biases laterally against at least a portion of the lacrimal canaliculus located at or more distal to a canalicular curvature; the extension in the second direction having a longitudinal length less than four times a longitudinal length of the extension in the first direction; and wherein the intermediate portion partially extends in a third direction, substantially opposite the second direction, toward a lacrimal canaliculus ampulla when the implant body is implanted, the extension in the third direction including a flat hull-like shape.

33. The lacrimal implant according to aspect 32, comprising a graspable projection extending at least partially from the proximal end portion, the graspable projection including an ovoid shape.

34. The lacrimal implant according to any of aspects 32 or 33, wherein the flat hull-like shape includes a length between about 0.4 to 0.5 millimeters, and a thickness of about 0.5 to 0.6 millimeters.

35. The lacrimal implant according to any of aspects 32-34, further comprising a therapeutic agent.

36. The lacrimal implant according to aspect 35, comprising at least one drug insert, distinct from the implant body, disposed in a cavity of the proximal end portion, the drug insert comprising a polymeric matrix including the therapeutic agent.

37. The lacrimal implant according to any of aspects 35 or 36, wherein the therapeutic agent is integrated into one or more portions of the implant body.

38. A kit comprising the lacrimal implant according to any of aspects 32-37, and an instruction for using the lacrimal implant to treat an eye disease.

39. A lacrimal implant insertable into a lacrimal canaliculus, comprising: an implant body, including first and second portions, the implant body extending from a proximal end of the first portion to a distal end of the second portion, the proximal end of the first portion defining a longitudinal proximal axis and the distal end of the second portion defining a longitudinal distal axis; the implant body configured such that, when implanted in the lacrimal canaliculus, an angled intersection exists between the proximal axis and the distal axis for biasing at least a portion of the implant body against at least a portion of the lacrimal canaliculus located at or more distal to a canalicular curvature; and a graspable projection extending at least partially from the proximal end of the first portion, the graspable projection including an inward-extending retaining lip that overhangs a cavity within the first portion.

40. The lacrimal implant according to aspect 39, further comprising at least one drug insert, distinct from the implant body, disposed in the cavity of the first portion, the drug insert comprising a therapeutic agent.

41. The lacrimal implant according to aspect 40, wherein the inward-extending retaining lip overhangs a proximal surface of the drug insert, when fully seated in the cavity, thereby securing a position of the insert.

42. The lacrimal implant according to aspect 41, wherein the overhang does not appreciably effect a release rate of the drug stored in the drug insert.

43. A method of manufacturing a lacrimal implant insertable into a lacrimal canaliculus, the method comprising: forming an implant body extending from a proximal end of a first body portion to a distal end of a second body portion, including forming a cavity in the first body portion, extending the second body portion to a longitudinal length which is less than four times a longitudinal length of the first body portion, and configuring the proximal end and the distal end to respectively define, when implanted in the lacrimal canaliculus, a longitudinal proximal axis and a longitudinal distal axis that intersect at an angle such that the implant body is configured to directionally bias laterally against at least a portion of the lacrimal canaliculus located at or more distal to a canaliculus curvature; and disposing a drug insert, distinct from the implant body, in the cavity of the first body portion, including positioning an exposed surface of the drug insert above the proximal end of the first body portion.

44. A lacrimal implant for insertion into a lacrimal canaliculus, comprising: an implant body extending from a proximal end portion positionable within a vertical section of the lacrimal canaliculus to a distal end portion positionable within a horizontal section of the lacrimal canaliculus and having an intermediate portion therebetween; the intermediate portion partially extending in a first direction toward the proximal end portion and partially extending in a second direction toward the distal end portion such that, when implanted in the lacrimal canaliculus, the implant body directionally biases laterally against at least a portion of the lacrimal canaliculus located at or more distal to a canalicular curvature; and a retention projection disposed at or near the distal end portion.

45. The lacrimal implant according to aspect 44, wherein the second direction extension includes a generally concave shape relative to the first direction extension; and wherein a radius of the generally concave shape is less than the radius of the canaliculus curvature.

46. A lacrimal implant for insertion into a lacrimal canaliculus, comprising: an implant body including at least one cavity; a drug insert, distinct from the implant body, disposed in the at least one cavity;, the drug insert including a polymeric matrix and therapeutic agent; and wherein the implant body includes therapeutic agent integrated with one or more body portions.

47. The lacrimal implant according to aspect 46, further comprising a sheath body surrounding one or more surfaces of the drug insert.

48. The lacrimal implant according to any of aspects 46 or 47, further comprising a coating applied to one or more portions of an outer implant body surface.

49. The lacrimal implant according to aspect 48, wherein a first coating thickness is applied to a first implant body surface portion and a second coating thickness, different from the first coating thickness, is applied to a second implant body surface portion.

50. The lacrimal implant according to any of aspects 48 or 49, wherein the coating includes at least one of parylene, ceramic or silver.

51. The lacrimal implant according to any of aspects 46-50, wherein the drug insert includes a first supply of therapeutic agent and the implant body includes a second supply of therapeutic agent.

These and other embodiments, advantages, and aspects of the present lacrimal implants and methods will be set forth in part in following Detailed Description. This Exemplary Embodiment section is intended to provide an overview of subject matter of the present patent application. It is not intended to provide an exclusive or exhaustive explanation of the present inventive implants. The Detailed Description is included to provide further information about the present patent document.

BRIEF DESCRIPTION OF THE DRAWINGS

In the drawings, like numerals can be used to describe similar components throughout the several views. Like numerals having different letter suffixes can be used to represent different instances of similar components. The drawings illustrate generally, by way of example, but not by way of limitation, various embodiments discussed in the present document.

FIGS. 21A-22B illustrate side views of example lacrimal implants configured to be retained within a lacrimal punctum and associated canalicular anatomy, each lacrimal implant including one or more laterally extendable arms.

FIGS. 43A-43C illustrate an example lacrimal implant configured to be retained within a lacrimal punctum and associated canalicular anatomy, the lacrimal implant including at least one intermediately-disposed retainment projection, such as with a retention mechanism on a proximal segment that can taper into a distal segment.

FIGS. 48A-48E illustrate an example lacrimal implant configured to be retained within a lacrimal punctum and associated canalicular anatomy, the lacrimal implant including a robust projection disposable within a lacrimal canaliculus ampulla.

FIGS. 49A-49F illustrate an example lacrimal implant configured to be retained within a lacrimal punctum and associated canalicular anatomy, the lacrimal implant including a retaining lip configured to help secure a distinct drug insert within an implant body cavity.

FIGS. 53A-53D illustrate example lacrimal implants configured to be retained within a lacrimal punctum and associated canalicular anatomy, the lacrimal implant including one or both of a distinct drug insert or drug integrated with an implant body.

DETAILED DESCRIPTION

In this patent document, lacrimal implants and related methods providing secure, wedgable retention within a lacrimal punctum and associated canaliculus of an eye are described. The lacrimal implants can comprise an implant body configured for at least partial insertion through the lacrimal punctum and into the associated canaliculus. The implant body can include first and second portions, and can extend from a proximal end of the first portion defining a longitudinal proximal axis to a distal end of the second portion defining a longitudinal distal axis. The implant body can be configured such that, when implanted using an integral dilator, an at least 45 degree angled intersection, for example, exists between the proximal axis and the distal axis. In this way, at least a portion of the implant body can be biased against at least a portion of the lacrimal canaliculus located at or more distal to a canalicular curvature, thereby retaining an implanted position of the lacrimal implant using anatomical structures.

In various examples, the lacrimal implant can further comprise a distinct drug insert or integrated drug or other agent disposed in at least one of the first portion or the second portion of the implant body, providing a sustained release of a drug or other therapeutic agent to one or more of an eye, nasal passage or inner ear system.

Figure 1:
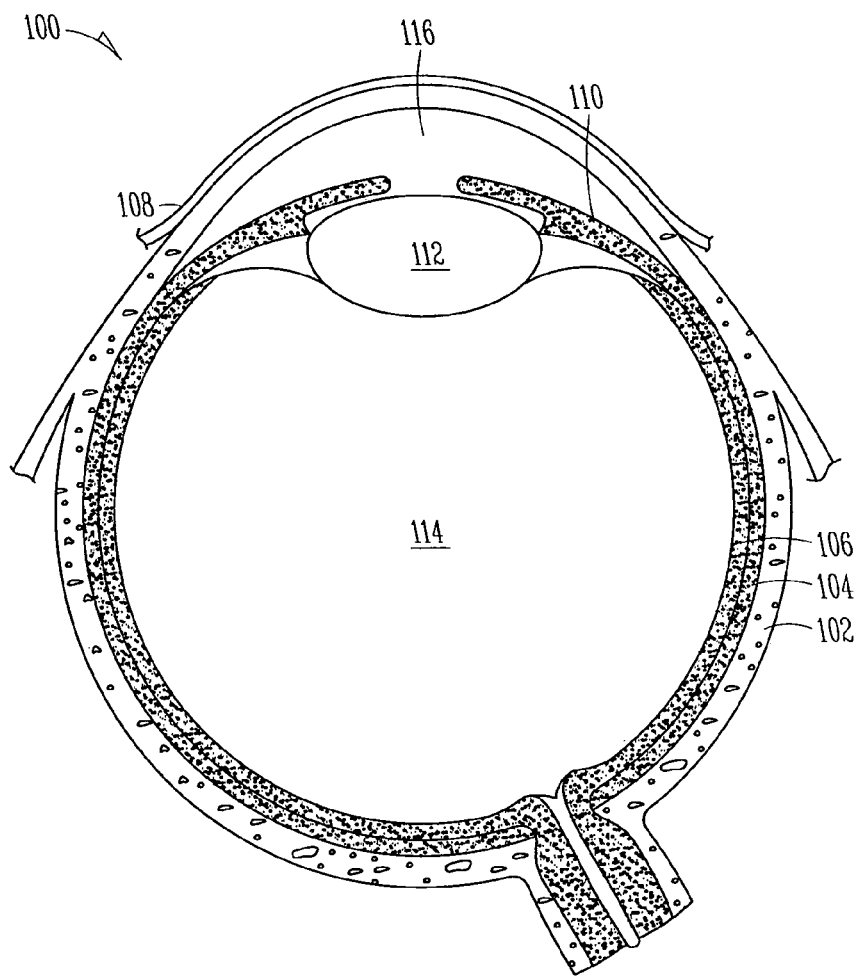
FIGS. 1-2 illustrate example views of anatomical tissue structures associated with the eye, certain of these tissue structures providing a suitable environment in which a lacrimal implant can be used.
Figure 2:
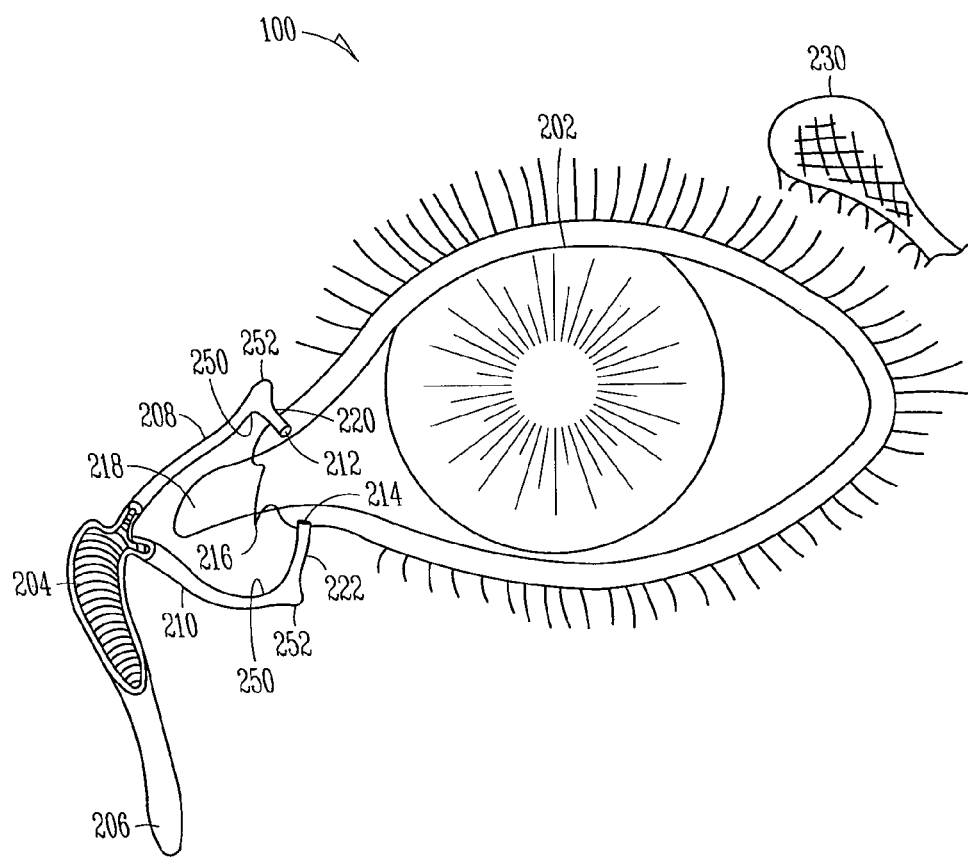

FIGS. 1-2 illustrate example views of anatomical tissue structures associated with an eye 100. Certain of the anatomical tissue structures shown can be suitable for treatment using the various lacrimal implants and methods discussed herein. The eye 100 is a spherical structure including a wall having three layers: an outer sclera 102, a middle choroid layer 104 and an inner retina 106. The sclera 102 includes a tough fibrous coating that protects the inner layers. It is mostly white except for the transparent area at the front, commonly known as the cornea 108, which allows light to enter the eye 100.

The choroid layer 104, situated inside the sclera 102, contains many blood vessels and is modified at the front of the eye 100 as a pigmented iris 110. A biconvex lens 112 is situated just behind the pupil. A chamber 114 behind the lens 112 is filled with vitreous humour, a gelatinous substance. Anterior and posterior chambers 116 are situated between the cornea 108 and iris 110, respectively and filled with aqueous humour. At the back of the eye 100 is the light-detecting retina 106.

The cornea 108 is an optically transparent tissue that conveys images to the back of the eye 100. It includes avascular tissue to which nutrients and oxygen are supplied via bathing with lacrimal fluid and aqueous humour as well as from blood vessels that line the junction between the cornea 108 and sclera 102. The cornea 108 includes a pathway for the permeation of drugs into the eye 100.

Turing to FIG. 2, other anatomical tissue structures associated with the eye 100 including the lacrimal drainage system, which includes a secretory system 230, a distributive system and an excretory system, are shown. The secretory system 230 comprises secretors that are stimulated by blinking and temperature change due to tear evaporation and reflex secretors that have an efferent parasympathetic nerve supply and secrete tears in response to physical or emotional stimulation. The distributive system includes the eyelids 202 and the tear meniscus around the lid edges of an open eye, which spread tears over the ocular surface by blinking, thus reducing dry areas from developing.

The excretory part of the lacrimal drainage system includes, in order of flow drainage, the lacrimal puncta, the lacrimal canaliculi, the lacrimal sac 204 and the lacrimal duct 206. From the lacrimal duct 206, tears and other flowable materials drain into a passage of the nasolacrimal system. The lacrimal canaliculi include an upper (superior) lacrimal canaliculus 208 and a lower (inferior) lacrimal canaliculus 210, which respectively terminate in an upper 212 and lower 214 lacrimal punctum. The upper 212 and lower 214 punctum are slightly elevated at the medial end of a lid margin at the junction 216 of the ciliary and lacrimal portions near a conjunctival sac 218. The upper 212 and lower 214 punctum are generally round or slightly ovoid openings surrounded by a connective ring of tissue. Each of puncta 212, 214 leads into a vertical portion 220, 222 of their respective canaliculus before turning more horizontal at a canaliculus curvature 250 to join one another at the entrance of the lacrimal sac 204. The canaliculi 208, 210 are generally tubular in shape and lined by stratified squamous epithelium surrounded by elastic tissue, which permits them to be dilated. As shown, a lacrimal canaliculus ampulla 252 exists near an outer edge of each canaliculus curvature 250.

Figure 3A:
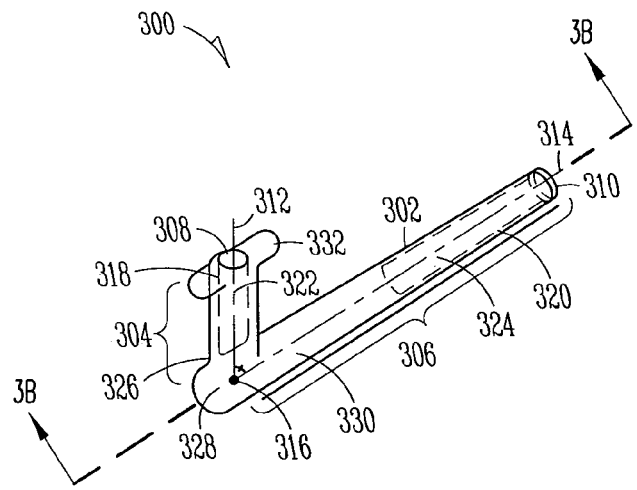
FIG. 3A illustrates an isometric view of an example lacrimal implant configured to be retained within a lacrimal punctum and associated canalicular anatomy, the lacrimal implant including an angled intersection between first and second implant body portions.

FIG. 3A illustrates an example lacrimal implant 300 that can be insertable through a lacrimal punctum 212, 214 and into the associated canaliculus 208, 210 (FIG. 2). The insertion of the lacrimal implant 300 through the lacrimal punctum 212, 214 and into the associated canaliculus 208, 210 can allow for one or more of: inhibition or blockage of tear flow therethrough (e.g., to treat dry eyes) or the sustained delivery of a drug or other therapeutic agent to an eye (e.g., to treat an infection, inflammation, glaucoma or other ocular disease or disorder), a nasal passage (e.g., to treat a sinus or allergy disorder) or an inner ear system (e.g., to treat dizziness or a migraine).

As shown in this example, the lacrimal implant 300 can comprise an implant body 302 including first 304 and second 306 portions, and can extend from a proximal end 308 of the first portion 304 to a distal end 310 of the second portion 306. In various examples, the proximal end 308 can define a longitudinal proximal axis 312 and the distal end 310 can define a longitudinal distal axis 314. The implant body 300 can be configured such that, when implanted within the lacrimal punctum and associated canaliculus, an at least 45 degree angled intersection 316 exists between the proximal axis 312 and the distal axis 314 for biasing at least a portion of the implant body 302 against at least a portion of a lacrimal canaliculus 208, 210 (FIG. 2) located at or more distal to a canaliculus curvature 250 (FIG. 2). In some examples, the implant body 302 can be configured such that the angled intersection 316 is between about 45 degrees and about 135 degrees. In this example, the implant body 302 is configured such that the angled intersection 316 is about 90 degrees (i.e., the intersection 316 between the proximal axis 312 and the distal axis. 314 is about perpendicular). In various examples, a distal end 326 of the first portion 304 can be integral with the second portion 306 at or near a proximal end 328 of the second portion 306.

In certain examples, the implant body 302 can include angularly disposed cylindrical-like structures comprising one or both of a first cavity 318 disposed near the proximal end 308 or a second cavity 320 disposed near the distal end 310. In this example, the first cavity 318 extends inward from the proximal end 308 of the first portion 304, and the second cavity 320 extends inward from the distal end 310 of the second portion 306. Optionally, one or more portions of the implant body 302 can include an ovoid cross-sectional shape for anatomical fitting purposes.

A first drug-releasing or other agent-releasing insert (e.g., drug core) 322 can be disposed in the first cavity 318 to provide a sustained drug or other therapeutic agent release to an eye, while a second drug-releasing or other agent-releasing insert (e.g., drug core) 324 can alternatively or conjunctively be disposed in the second cavity 320 to provide a sustained drug or other therapeutic agent release to a nasal passage or inner ear system, for example. An implant body septum 330 can be positioned between the first cavity 318 and the second cavity 320, and can be used to inhibit or prevent communication of a material (e.g., agent) between the first drug insert 322 and the second drug insert 324. In various examples, one or both of the first drug-releasing or other agent-releasing insert 322 or the second drug-releasing or other agent-releasing insert 324 can include at least 21 micrograms, at least 42 micrograms, at least 44 micrograms, at least 81 micrograms, or at least 95 micrograms of a drug (e.g., latanoprost), such as is further discussed in commonly-owned Butuner et al., U.S. patent application Ser. No. 12/463,279, entitled "SUSTAINED RELEASE DELIVERY OF ACTIVE AGENTS TO TREAT GLAUCOMA AND OCULAR HYPERTENSION," filed May 8, 2009, and commonly-owned Utkhede, U.S. Patent Application No. 61/277,000, entitled "IMPROVED DRUG CORES FOR SUSTAINED OCULAR RELEASE OF THERAPEUTIC AGENTS," filed Sep. 18, 2009, both of which are incorporated by reference in their entirety, including their descriptions of drug or other agent concentration.

In some examples, the implant body 302 is substantially solid in the fact that it does not include one or more cavities or other voids for receiving a drug-releasing or other agent-releasing insert. Rather, the implant body 302 can be configured to receive one or more drugs or other agents integrated throughout one or more body portions. In this way, the entire implant body 302, or portions thereof, can act as the drug-releasing or other agent-releasing insert, and agent release can be directed using a preformed opening(s) in an impermeable or substantially impermeable cover (e.g., parylene cover) surrounding portions of the implant body 302. In other examples, a permeable cover material can be used to allow for drug or other agent release.

In some examples, the drug or other therapeutic agent release can occur, at least in part, via an exposed, non-sheath covered, surface of the drug inserts 322, 324. By controlling geometry of the exposed surface, a predetermined drug or agent release rate can be achieved. For instance, the exposed surface can be constructed with a specific geometry or other technique appropriate to control the release rate of the drug or other therapeutic agent onto an eye 100, such as on an acute basis or on a chronic basis, between outpatient doctor visits. Further description regarding effective release rates of one or more drugs or other therapeutic agents from a drug insert 322, 324 can be found in commonly-owned DeJuan et al., U.S. patent application Ser. No. 11/695,545, entitled "NASOLACRIMAL DRAINAGE SYSTEM IMPLANTS FOR DRUG THERAPY," which is herein incorporated by reference in its entirety, including its description of obtaining particular release rates.

Figure 3B:
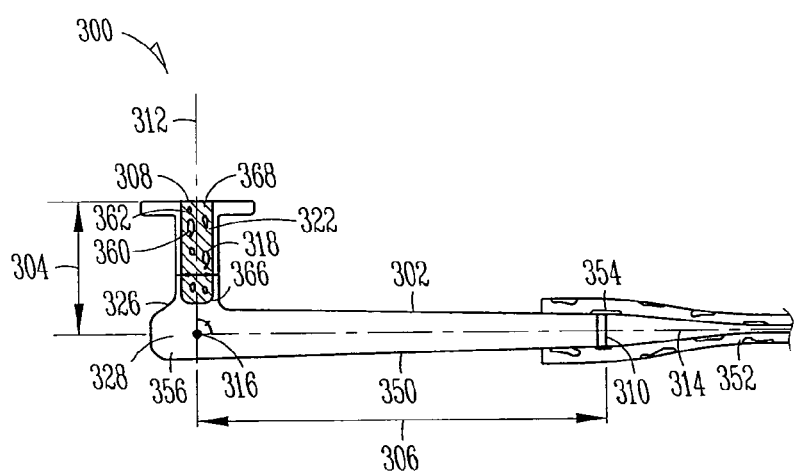
FIG. 3B illustrates a cross-sectional view of an example lacrimal implant taken along a line parallel to a longitudinal axis of the implant, such as along line 3B-3B, and a dilation of implant-receiving anatomical tissue structure.
Figure 4:
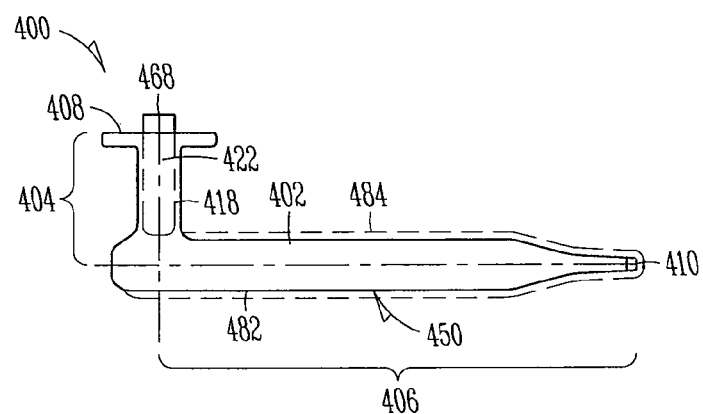
FIG. 4 illustrates a side view of an example lacrimal implant configured to be retained within a lacrimal punctum and associated canalicular anatomy, the lacrimal implant including an integral dilator.

In some examples, such as is shown in FIG. 3B, the exposed surface of the drug insert 322, 324 can be flush or slightly below the proximal end 308 of the first portion 304 or the distal end 310 of the second portion 306, respectively, such that the drug insert does not protrude outside of the implant body 302. In some examples, such as is shown in FIG. 4, the exposed surface of the first drug insert 322, for instance, can be positioned above the proximal end 308 such that the first drug insert 322 at least partially protrudes outside of the implant body 302.

The implant body 302 can include a graspable or other projection 332, such as one or more projections extending laterally at least partially from or around a proximal end 308 of the first implant body portion 304. In some examples, the graspable or other projection 332 can include a set of wings for use in inserting the lacrimal implant 300 into, or removing the lacrimal implant 300 from, an implanted position. The set of wings or other projection 332 can be configured without migration in mind, as the non-linear configuration of the implant body 302 can prevent implant 300 migration by assuming a size or shape of the canaliculus curvature 250 and optionally, the lacrimal canaliculus ampulla 252 (FIG. 2). In some examples, the graspable or other projection 332 can be configured to seat against or near the punctal opening 212, 214, such as for inhibiting or preventing the lacrimal implant 300 from passing completely within the lacrimal canaliculus 208, 210, or for providing tactile or visual feedback information to an implanting user, e.g., as to whether the implant is fully implanted.

Figure 34A:
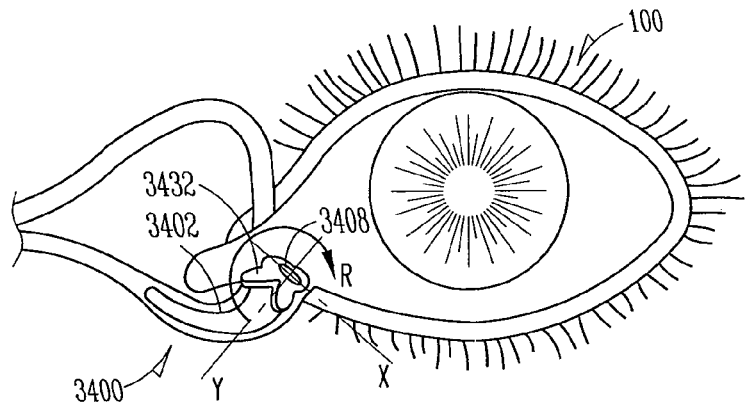
FIGS. 34A-34B illustrate schematic views of example lacrimal implants retained within a lacrimal punctum and associated canalicular anatomy, each lacrimal implant including an oriented graspable projection.
Figure 34B:
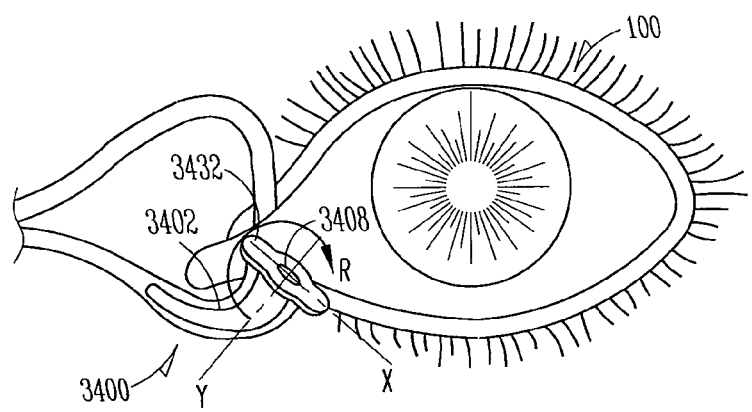

As shown in FIGS. 34A-34B, and discussed further below, the graspable or other projection 332 can extend laterally in a direction parallel to or away from an eye 100 when implanted. It is believed that this may reduce irritation to the eye 100, as compared to a case in which a portion of the projection extends toward the eye 100. In addition, a lateral extension direction of the projection 332 from the proximal end 308 can be substantially the same as a lateral extension direction of the second implant body portion 306 relative to the distal end 326 of the first implant body portion 304, as shown in FIGS. 3A-3B, for example. This can also avoid projection extension toward the eye and facilitate insertion orientation for an implanting caregiver physician. The first drug insert 322 can partially extend though the region of the projection 332, such as to provide sustained release of a first drug or other therapeutic agent onto an eye.

In various examples, the implant body 302 can be molded using an elastic material, such as silicone, polyurethane or other urethane-based polymer or copolymer, NuSil (e.g., NuSil 4840 with 2% 6-4800) or an acrylic of a non-biodegradable, partially biodegradable or biodegradable nature (i.e., erodeable within the body) allowing an implant body 302 configured such that, when implanted in a lacrimal canaliculus 208, 210, an angled intersection 316 exists between a proximal 312 and distal 314 axis to be formed. Silicone, for example, is believed to be soft enough to be comfortable for patients, and stiff enough to facilitate insertion by a caregiver physician. In various examples, a biocompatible colorant (e.g., green colorant) can be mixed with the elastic material of the implant body 302 allowing patients and their caregivers to more easily see the implant and verify it remains in an implanted position. In some examples, the biocompatible colorant can be mixed with materials of the drug insert 322 for implant feedback or to indicate the type, size, agent or other characteristic of the implant.

In some examples, the biodegradable elastic materials can include cross-linked polymers, such as poly (vinyl alcohol). In some examples, the implant body 302 can comprise a silicone/polyurethane co-polymer. Other co-polymers that can be used to form the implant body 302 include, but are not limited to, silicone/urethane, silicone/poly (ethylene glycol) (PEG), and silicone/2hydroxyethyl methacrylate (HEMA). As discussed in commonly-owned Utkhede et al., U.S. patent application Ser. No. 12/231,986, entitled "DRUG CORES FOR SUSTAINED RELEASE OF THERAPEUTIC AGENTS," filed Sep. 5, 2008, which is herein incorporated by reference in its entirety, urethane-based polymer and copolymer materials allow for a variety of processing methods and bond well to one another.

FIG. 3B illustrates an example cross-sectional view of the lacrimal implant 300 taken along a line parallel to a longitudinal axis of the implant, such as along line 3B-3B of FIG. 3A. As shown in FIG. 3B, the lacrimal implant 300 can include an implant body 302 including first 304 and second 306 portions, and can extend from a proximal end 308 of the first portion 304 to a distal end 310 of the second portion 306. In various examples, the proximal end 308 can define a longitudinal proximal axis 312 and the distal end 310 can define a longitudinal distal axis 314. The implant body 300 can be configured such that, when implanted, an at least 45 degree angled intersection 316 exists between the proximal axis 312 and the distal axis 314 for biasing at least a portion of the implant body 302 against at least a portion of a lacrimal canaliculus 208, 210 (FIG. 2) located at or more distal to a canaliculus curvature 250 (FIG. 2). In this example, the implant body 300 is configured such that the angled intersection 316 is approximately about 90 degrees.

In various examples, a distal end 326 of the first portion 304 can be integral with the second portion 306 at or near a proximal end 328 of the second portion 306. In some examples, the second portion 306 can include a length having a magnitude less than four times a length of the first portion 304. In one example, the second portion 306 can include a length of less than about 10 millimeters and have a configuration similar to that shown in FIG. 3B. In another example, the second portion 306 can include a length less than about 2 millimeters and have a configuration similar to that shown in FIG. 24.

In various examples, the second portion 306 can comprise an integral dilator 350 to dilate anatomical tissue 352, such as one or both of a lacrimal punctum 212, 214 (FIG. 2) or associated canaliculus 208, 210, to a sufficient diameter as the lacrimal implant 300 is being implanted. In this way, the lacrimal implant 300 can be implanted in various sized ocular anatomies without the need for pre-dilation via a separate enlarging tool. The dilator 350 can be formed so as to not be traumatic to an inner lining of the punctum 212, 214 and the canaliculus 208, 210. In some examples, a lubricious coating disposed on, or impregnated in, an outer surface of the implant body 302 can be used to further aid insertion of the lacrimal implant 300 into the anatomical tissue 352. In one example, the lubricious coating can include a silicone lubricant.

The dilator 350 can generally narrow from a location near the proximal end 328 of the second portion 306 to the distal end 310 of the second portion 306, such as from a diameter of about 0.6 millimeters to a diameter of about 0.2 millimeters. In some examples, an outer surface slope of the dilator 350, as measured from the location near the proximal end 328 of the second portion 306 to the distal end 310 of the second portion 306, can be between about 1 degree and about 10 degrees (e.g., 2 degrees, 3 degrees, 4 degrees, or 5 degrees) with respect to the longitudinal distal axis 314. In some examples, the slope of the dilator 350 can be less than 45 degrees with respect to the longitudinal distal axis 314. Among other factors, a determination of a desirable dilator 350 slope for a given implant situation can be made by balancing an implant body 302 strength desirable for implantation with a desire to have a soft, flexible and conforming implant body (e.g., to conform to a lacrimal canaliculus anatomy) upon implantation. In some examples, a diameter of a dilator tip 354 can be between about 0.2 millimeters and about 0.5 millimeters.

In certain examples, the proximal end 328 of the second implant body portion 306 can include a retention element 356 configured to bias against at least a portion of a lacrimal canaliculus ampulla 252 (FIG. 2) when implanted. In this example, the retention element 356 projects proximally from the intersection between the first 304 and second 306 implant body portions, such as in an opposite direction as the extension of the dilator 350. When present and implanted in the ampulla 252, the retention element 356 can help secure a seated position of the graspable or other projection 332 against the punctal opening 212, 214.

In certain examples, the implant body 302 includes a first cavity 318 disposed near the proximal end 308. In this example, the first cavity 318 extends inward about 2 millimeters or less from the proximal end 308, and houses a first drug-releasing or other agent-releasing drug insert 322 to provide a sustained drug or other agent release to an eye. In some examples, the drug insert 322 can include a plurality of therapeutic agent inclusions 360, which can be distributed in a matrix 362. In some examples, the inclusions 360 can comprise a concentrated (e.g., crystalline) form of the therapeutic agent. In some examples, the matrix 362 can comprise a silicone matrix or the like, and the distribution of inclusions 360 within the matrix can be substantially homogenous or non-homogeneous. In some examples, the agent inclusions 360 can include droplets of oil, such as Latanoprost oil. In still other examples, the agent inclusions 360 can comprise solid particles, such as Bimatoprost particles in crystalline form. In some examples, the drug insert 322 comprises a urethane-based (e.g., polyurethane) polymer or copolymer comprising therapeutic agent inclusions deliverable into the eye or surrounding tissues. The inclusions can be of many sizes and shapes. For instance, the inclusions can include microparticles having dimensions on the order of about 1 micrometer to about 100 micrometers. Further discussion of drug-releasing or other agent-releasing drug inserts can be found in commonly-owned Utkhede et al., U.S. patent application Ser. No. 12/231,986, entitled "DRUG CORES. FOR SUSTAINED RELEASE OF THERAPEUTIC AGENTS," filed Sep. 5, 2008, which is herein incorporated by reference in its entirety.

In various examples, the drug insert 322 can include a sheath body 366 disposed over at least a portion of the insert to define at least one insert exposed surface 368. The exposed surface 368 can be located at or near the proximal end 308 of the implant body 302, for example, thereby allowing direct contact with a tear or a tear film fluid and release of a drug or other therapeutic agent from the drug insert 322 over a sustained time period when the lacrimal implant 300 is inserted through the lacrimal punctum 212, 214 and into the associated canaliculus 208, 210.

FIG. 4 illustrates an example side view of another integral dilator 450 of an implant body 402 second portion 406 of a lacrimal implant 400. In this example, the dilator 450 narrows abruptly near a distal end 410 of the second portion 406. As shown, an implant body first portion 404 can include a first cavity 418 disposed near the proximal end 408. In this example, the first cavity 418 extends inward from the proximal end 408, and houses a first drug-releasing or other agent-releasing drug insert 422 to provide a sustained drug or other therapeutic agent release to an eye, for instance. In some examples, the drug or other therapeutic agent can released to an eye via an exposed, non-sheath covered surface 468 of the drug insert 422. In this example, the exposed surface 468 of the drug insert 422 is positioned above the proximal end 408 such that the drug insert 422 at least partially protrudes outside of the implant body 402.

In various examples, the outer surface 482 of the implant body 402 can be formed, or surface treated to be, generally smooth to inhibit bacteria from attaching to the lacrimal implant 400 and incubating. The generally smooth outer surface 482 can also prevent damage to the inner lining of the receiving anatomical tissue, such as a lacrimal punctum 212, 214 (FIG. 2) or associated canaliculus 208, 210 (FIG. 2), during implantation. As further discussed in commonly-owned Rapacki et al., U.S. patent application Ser. No. 12/283,002, entitled "SURFACE TREATMENT OF IMPLANTS AND RELATED METHODS," filed Sep. 5, 2008, which is herein incorporated by reference in its entirety, the outer surface 482 of the implant body 402 can be surface treated to be generally smooth via a polishing process. The polishing process can include causing a molded implant body 402 to be impacted with polishing media during an ongoing period of time in which the body 402 is in an enlarged, swelled state. This can smooth one or more surfaces or edges of the implant body 402. In various examples, the polishing media can include at least some granules that are greater than about 3 millimeters in diameter.

In various examples, an antimicrobial coating 484 can be disposed on or impregnated in at least a portion of the outer surface 482 to further prevent bacteria growth on the implant body 402. In some examples, the antimicrobial coating 484 can include an agent selected from the group consisting of 2-bromo-2-nitropropane-1,3-diol, 5-bromo-5-nitro-1,3-dioxane, 7-ethyl bicyclooxazolidine, benzalkonium chloride, benzethonium chloride, benzoic acid, benzyl alcohol, boric acid, bronopol, cetylpyridinium chloride, chlorhexidine digluconate, chloroacetamide, chlorobutanol, chloromethyl isothiazolinone and methyl isothiazoline, dimethoxane, dimethyl oxazolidine, dimethyl hydroxymethyl pyrazole, chloroxylenol, dehydroacetic acid, diazolidinyl urea, dichlorobenzyl alcohol, DMDM hydantoin, ethyl alcohol, formaldehyde, glutaraldehyde, hexachlorophene, hexetidine, hexamethylenetramine, imidazolidinyl urea, iodopropynyl butylcarbamate, isothiazolinones, methenammonium chloride, methyldibromo glutaronitrile, MDM hydantoin, minocycline, ortho phenylphenol, p-chloro-m-cresol, parabens (butylparaben, ethylparaben, methylparaben), phenethyl alcohol, phenoxyethanol, piroctane olamine, polyaminopropyl biguanide, polymethoxy bicyclic oxazolidine, polyoxymethylene, polyquaternium-42, potassium benzoate, potassium sorbate, propionic acid, quaternium-15, rifampin, salicylic acid, selenium disulfide, sodium borate, sodium iodate, sodium hydroxymethylglycinate, sodium propionate, sodium pyrithione, sorbic acid, thimerosal, triclosan, triclocarban, undecylenic acid, zinc phenosulfonate, and zinc pyrithione. In some examples, the antimicrobial coating 484 can include a material selected from the group consisting of silver lactate, silver phosphate, silver citrate, silver acetate, silver benzoate, silver chloride, silver iodide, silver Iodate, silver nitrate, silver sulfadiazine, silver palmitate, or one or more mixtures thereof. In some examples, the antimicrobial coating 484 can include at least one of an antibiotic or an antiseptic. For instance, the antimicrobial coating 484 can include a temporary anesthetic lasting, on average, between a few hours and a day. In still other examples, the antimicrobial coating 484 can include a drug or other therapeutic agent used to treat an underlying disease, such as a bolus, for immediate effect.

Figure 5:
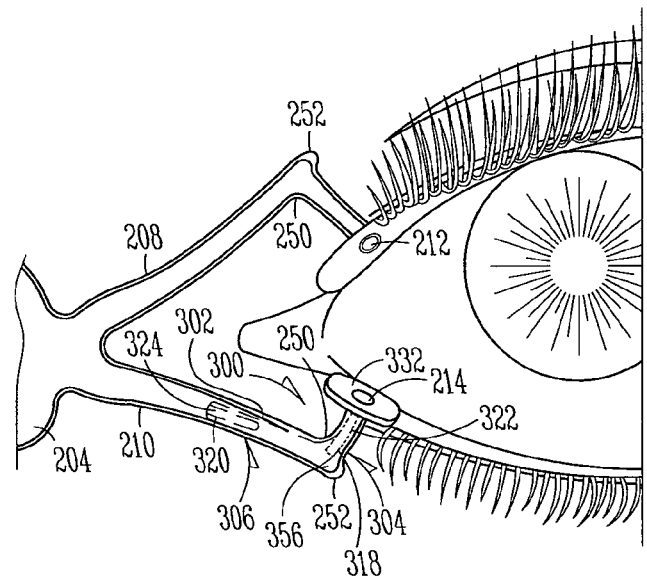
FIG. 5 illustrates a schematic view of an example lacrimal implant retained within a lacrimal punctum and associated canalicular anatomy, the lacrimal implant including at least one drug or other therapeutic agent.

FIG. 5 illustrates an example schematic view of a lacrimal implant, such as the lacrimal implant 300 shown in FIG. 3, implanted in a lower lacrimal punctum 214 and associated canaliculus 210. In some examples, a lacrimal implant 300 can be implanted in an upper lacrimal punctum 212 and canaliculus 208. As further discussed above, the lacrimal implant 300 can comprise an implant body 302 including first 304 and second 306 portions. In various examples, the implant body 302 can be configured such that, when implanted, at least a portion of the implant body 302 is biased against at least a portion of the lacrimal canaliculus 210 located at or more distal to a canaliculus curvature 250 to securely retain an implanted position of the implant 300. As shown, the first portion 304 can be configured to be inserted through the lacrimal punctum 214 and into the associated canaliculus 210 and rest between the punctal opening and a lacrimal canaliculus ampulla 252, while the second portion 306 can be configured to insert through the lacrimal punctum 214 and into the canaliculus 210 and rest between the ampulla 252 and the lacrimal sac 204. In certain examples, a retention element 356 projecting from a proximal end of the second portion 306 can be configured to bias into and against at least a portion of the ampulla 252 when implanted. In various examples, the first 304 and second 306 portions can be configured to bend, stretch or collapse, as desired, to maintain an adequate anatomical implanted fit without unduly stretching ocular anatomy.

In certain examples, to further secure an implant 300 within the lacrimal punctum 214 and canaliculus 210 or to make the implant body 302 adjustable in size, a hydrogel or other fluid swellable material can be disposed (e.g., coated) on an outer surface portion of the implant body 302. The fluid swellable material can effectively expand an outer surface diameter portion of the implant body 302 when implanted. In certain examples, the outer surface of the implant body 302 can include longitudinal channels or grooves or coatings of a wicking material so as to allow fluid flow around the implant body 302. Using one or a combination of these techniques, a lacrimal implant 300 can be configured to completely occlude or only partially occlude the lacrimal canaliculus 208, 210 when implanted therein. For instance, using the longitudinal channels or grooves in one or both of the first 304 or second 306 portions of the implant body 302 can allow diminished volumes or tear drainage can occur, potentially facilitating the release of a drug or other therapeutic agent from a drug insert.

Forceps or another insertion tool can be used to implant the lacrimal implant 300 through the lacrimal punctum 212, 214 and into the associated canaliculus 208, 210. In some examples, an insertion tool as discussed in commonly-owned De Juan, et al., U.S. patent application Ser. No. 12/231,984, entitled "INSERTION AND EXTRACTION TOOLS FOR LACRIMAL IMPLANTS," filed Sep. 5, 2008, which is herein incorporated by reference in its entirety, can be used to implant the lacrimal implant 300. In various examples, the second portion 306 of the implant body 302 can be advanced into the depth of the lacrimal canaliculus 208, 210 by manipulation of the inserter tool until a graspable or other projection 332, if present, can be seated against the punctal opening 212, 214.

In various examples, after a punctal size has been measured and an appropriately-sized implant 300 (e.g., small, medium or large) is selected, the punctum 212, 214 can optionally be dilated pre-insertion or during insertion (e.g., via an implant's integral dilator). The implant 300 can be grasped at the second portion 306 with forceps or another insertion tool and introduced into the punctum 212, 214 vertically. The implant 300 can then be rotated to advance it into the horizontal portion of the lacrimal canaliculus 208, 210 up to the heel-like retention element 356. The forceps or other insertion tool can further be used to grasp the retention element 356 portion of the implant 300 to rotate it into the punctum 212, 214 such that the graspable or other cap-like projection 332 can be seated on the punctum.

When it is desired to remove the lacrimal implant 300, the projection 332 can be grasped with the forceps, for example, and withdrawn from the punctal opening 212, 214 through a gentle tugging motion. Optionally, a drop or two of an anesthetic can be administered prior to implant 300 removal. Care may need to be taken not to grasp the outermost edge of the projection 332, as this may cause the projection 332 to tear or separate.

In certain examples, the implant body 302 can include one or both of a first cavity 318 disposed near the proximal end 308 or a second cavity 320 disposed near the distal end 310. In this example, the first cavity 318 extends inward from the proximal end 308 of the first portion 304, and the second cavity 320 extends inward from the distal end 310 of the second portion 306. A first drug-releasing or other agent-releasing drug insert 322 can be disposed in the first cavity 318 to provide a sustained drug or other therapeutic agent release to the eye (e.g., to treat an infection, inflammation, glaucoma or other ocular disease or disorder), while a second drug-releasing or other agent-releasing drug insert 324 can be disposed in the second cavity 320 to provide a sustained drug or other therapeutic agent release to the nasal passage (e.g., to treat a sinus or allergy disorder) or inner ear system (e.g., to treat dizziness or a migraine), for example.

Figure 6A:
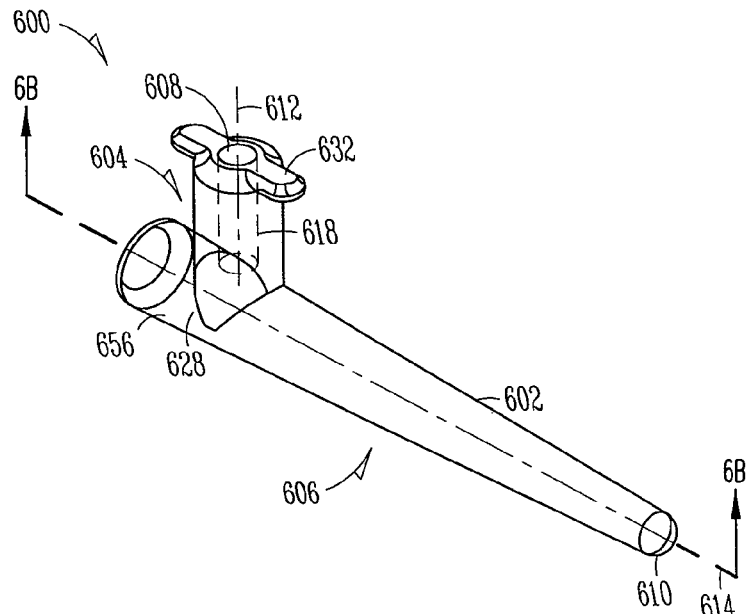
FIG. 6A illustrates an isometric view of an example lacrimal implant configured to be retained within a lacrimal punctum and associated canalicular anatomy, the lacrimal implant including a portion disposable within a lacrimal canaliculus ampulla.
Figure 6B:
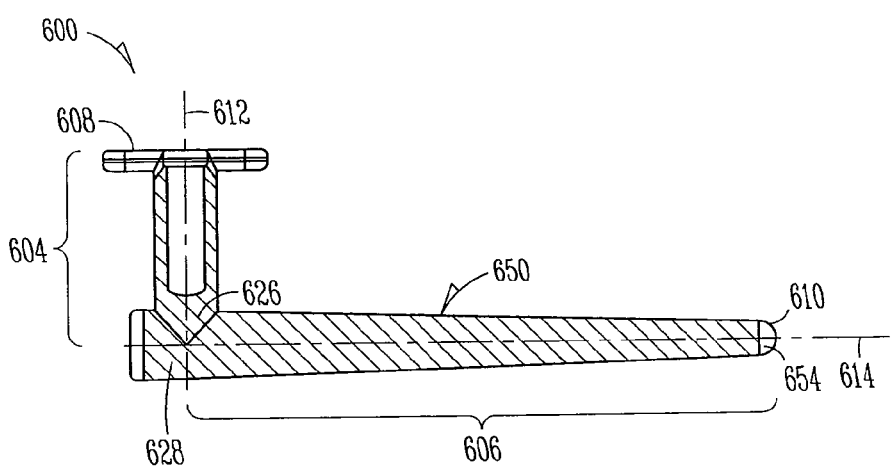
FIG. 6B illustrates a cross-sectional view of an example lacrimal implant taken along a line parallel to a longitudinal axis of the implant, such as along line 6B-6B.

FIGS. 6A-6B illustrate another lacrimal implant 600 example that is insertable through a lacrimal punctum 212, 214 and into the associated canaliculus 208, 210 (FIG. 2). In this example, the lacrimal implant 600 can comprises an implant body 602 including first 604 and second 606 portions, and can extend from a proximal end 608 of the first portion 604 to a distal end 610 of the second portion 606. The proximal end 608 can define a longitudinal proximal axis 612 and the distal end 610 can define a longitudinal distal axis 614. The implant body 600 can be configured such that, when implanted, an angled intersection of approximately 90 degrees exists between the proximal axis 612 and the distal axis 614 for biasing at least a portion of the implant body against at least a portion of the lacrimal canaliculus 208, 210 (FIG. 2) located at or more distal to a canaliculus curvature 250 (FIG. 2).

In this example, a proximal end 628 of the second implant body portion 606 can include a retention element 656 configured to bias against at least a portion of a lacrimal canaliculus ampulla 252 (FIG. 2) when implanted. In this example, the implant body 602 includes a first cavity 618, configured to receive a first drug-releasing or other agent-releasing drug insert, disposed near the proximal end 608 of the first implant body portion 604. Also in this example, the implant body 602 can include a graspable or other projection 632, such as a set of wings having a combined length of about 1 millimeter, for example, and extending laterally from the proximal end 308.

FIG. 6B illustrates an example cross-sectional view of the lacrimal implant 600 taken along a line parallel to a longitudinal axis of the implant, such as along line 6B-6B of FIG. 6A. As shown in FIG. 6B, a distal end 626 of the first portion 604 can be integral with the second portion 606 at or near a proximal end 628 of the second portion 606. In various examples, the second portion 606 can include a longitudinal length, as measured from the proximal axis 612 to the distal end 610, having a magnitude less than four times a longitudinal length of the first portion 604, as measured from the proximal end 608 to the distal axis 614. In some examples, the first portion can include a longitudinal length of about 1.54 millimeters and the second portion can include a longitudinal length of between about 4.5 millimeters to about 5.42 millimeters.

In various examples, the second portion 606 can comprise an integral dilator 650 to dilate anatomical tissue, such as one or both of the lacrimal punctum 212, 214 (FIG. 2) or associated canaliculus 208, 210, to a sufficient diameter as the lacrimal implant 600 is being implanted. In some examples, the second portion 606 tapers from a diameter of the proximal end of between about 0.50 millimeters to about 0.75 millimeters to a dilator tip 654 diameter of about 0.36 millimeters.

Figure 7A:
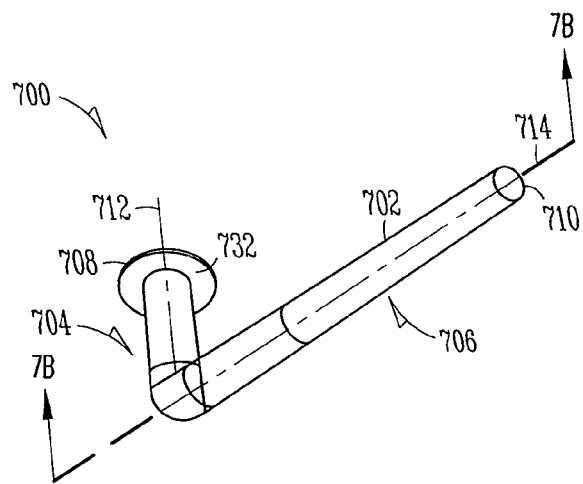
FIG. 7A illustrates an isometric view of an example lacrimal implant configured to be retained within a lacrimal punctum and associated canalicular anatomy, the lacrimal implant including an annular graspable projection.
Figure 7B:
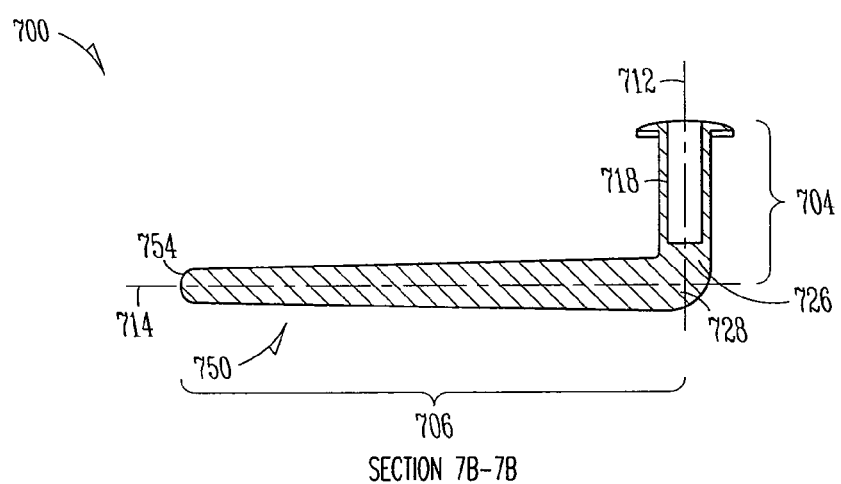
FIG. 7B illustrates a cross-sectional view of an example lacrimal implant taken along a line parallel to a longitudinal axis of the implant, such as along line 7B-7B.

FIGS. 7A-7B illustrate another lacrimal implant 700 example that is insertable through a lacrimal punctum 212, 214 and into the associated canaliculus 208, 210 (FIG. 2). In this example, the lacrimal implant 700 can comprises an implant body 702 including first 704 and second 706 portions, and can extend from a proximal end 708 of the first portion 704 to a distal end 710 of the second portion 706. The proximal end 708 can define a longitudinal proximal axis 712 and the distal end 710 can define a longitudinal distal axis 714. The implant body 700 can be configured such that, when implanted, an angled intersection of approximately 90 degrees exists between the proximal axis 712 and the distal axis 714 for biasing at least a portion of the implant body against at least a portion of the lacrimal canaliculus 208, 210 (FIG. 2) located at or more distal to a canaliculus curvature 250 (FIG. 2). As shown in the example of FIG. 7A, a smooth transition can exist between the first 704 and second 706 portions.

In this example, the implant body 702 includes a first cavity 718 configured to receive a first drug-releasing or other agent-releasing drug insert, disposed near the proximal end 708 of the first implant body portion 704. Also in this example, the implant body 702 can include a graspable or other projection 732, such as an annular projection extending laterally from, and completely around, the proximal end 708. In some examples, the graspable or other projection 732 includes a partially trimmed projection having a trimmed width of about 0.75 millimeters and extending varying amounts around the proximal end 708.

FIG. 7B illustrates an example cross-sectional view of the lacrimal implant 700 taken along a line parallel to a longitudinal axis of the implant, such as along line 7B-7B of FIG. 7A. As shown in FIG. 7B, a distal end 726 of the first portion 704 can be integral with the second portion 706 at or near a proximal end 728 of the second portion 706. In various examples, the second portion 706 can include a longitudinal length, as measured from the proximal axis 712 to the distal end 710, having a magnitude less than four times a longitudinal length of the first portion 704, as measured from the proximal end 708 to the distal axis 714. In some examples, the first portion can include a longitudinal length of about 1.5 millimeters and the second portion can include a longitudinal length of about 5 millimeters.

In various examples, the second portion 706 can comprise an integral dilator 750 to dilate anatomical tissue, such as one or both of the lacrimal punctum 212, 214 (FIG. 2) or associated canaliculus 208, 210, to a sufficient diameter as the lacrimal implant 700 is being implanted. In some examples, the second portion 706 tapers from a diameter of the proximal end of about 0.46 millimeters to a dilator tip 754 diameter of about 0.36 millimeters.

Figure 8A:
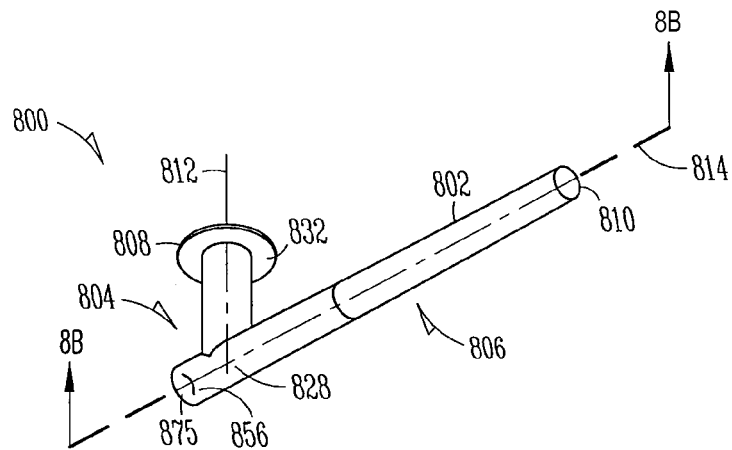
FIG. 8A illustrates an isometric view of an example lacrimal implant configured to be retained within a lacrimal punctum and associated canalicular anatomy, the lacrimal implant including a portion disposable within a lacrimal canaliculus ampulla and including an insertion-facilitating depression.
Figure 8B:
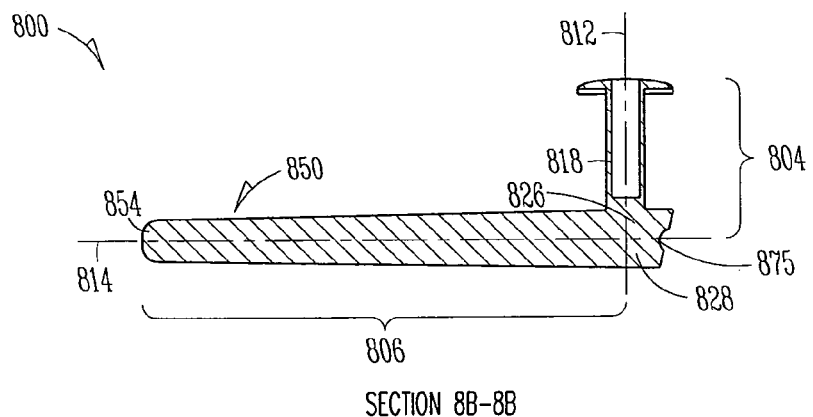
FIG. 8B illustrates a cross-sectional view of an example lacrimal implant taken along a line parallel to a longitudinal axis of the implant, such as along line 8B-8B.

FIGS. 8A-8B illustrate another lacrimal implant 800 example that is insertable through a lacrimal punctum 212, 214 and into the associated canaliculus 208, 210 (FIG. 2). In this example, the lacrimal implant 800 can comprises an implant body 802 including first 804 and second 806 portions, and can extend from a proximal end 808 of the first portion 804 to a distal end 810 of the second portion 806. The proximal end 808 can define a longitudinal proximal axis 812 and the distal end 810 can define a longitudinal distal axis 814. The implant body 800 can be configured such that, when implanted, an angled intersection of approximately 90 degrees exists between the proximal axis 812 and the distal axis 814 for biasing at least a portion of the implant body against at least a portion of the lacrimal canaliculus 208, 210 (FIG. 2) located at or more distal to a canaliculus curvature 250 (FIG. 2).

In this example, a proximal end 828 of the second implant body portion 806 can include a retention element 856 configured to bias against at least a portion of a lacrimal canaliculus ampulla 252 (FIG. 2) when implanted. The retention element 856 can include an insertion-facilitating depression 875 or other gripping means to aid in one or both of implant insertion or removal. In this example, the implant body 802 includes a first cavity 818 configured to receive a first drug-releasing or other agent-releasing drug insert, disposed near the proximal end 808 of the first implant body portion 804. Also in this example, the implant body 802 can include a graspable or other projection 832, such as an annular projection extending laterally from, and completely around, the proximal end 808. In some examples, the graspable or other projection 832 includes a partially trimmed projection extending varying amounts around the proximal end 808.

FIG. 8B illustrates an example cross-sectional view of the lacrimal implant 800 taken along a line parallel to a longitudinal axis of the implant, such as along line 8B-8B of FIG. 8A. As shown in FIG. 8B, a distal end 826 of the first portion 804 can be integral with the second portion 806 at or near the proximal end 828 of the second portion 806. In various examples, the second portion 806 can include a longitudinal length, as measured from the proximal axis 812 to the distal end 810, having a magnitude less than four times a longitudinal length of the first portion 804, as measured from the proximal end 808 to the distal axis 814. In some examples, the first portion can include a longitudinal length of between about 1.725 millimeters to about 1.77 millimeters and the second portion can include a longitudinal length of between about 4.77 millimeters to about 5 millimeters.

In various examples, the second portion 806 can comprise an integral dilator 850 to dilate anatomical tissue, such as one or both of the lacrimal punctum 212, 214 (FIG. 2) or associated canaliculus 208, 210, to a sufficient diameter as the lacrimal implant 800 is being implanted. In some examples, the second portion 806 tapers from a diameter of the proximal end 828 of about 0.46 millimeters to a dilator tip 854 diameter of about 0.36 millimeters.

Figure 9:
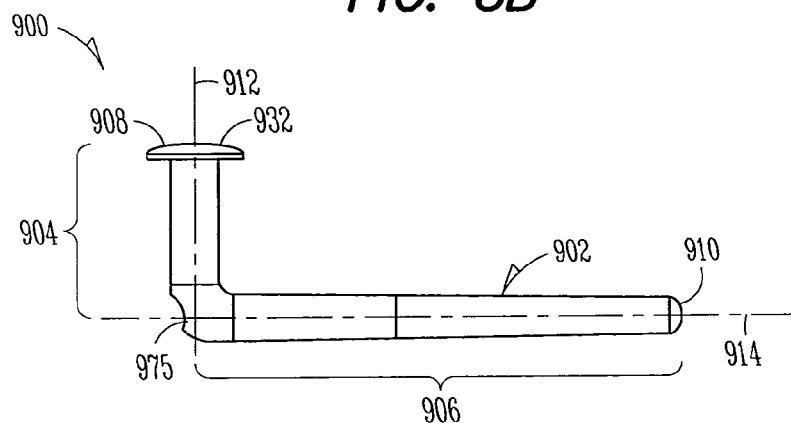
FIG. 9 illustrates a side view of an example lacrimal implant configured to be retained within a lacrimal punctum and associated canalicular anatomy, the lacrimal implant including an insertion-facilitating depression.

FIG. 9 illustrates another lacrimal implant 900 example that is insertable through a lacrimal punctum 212, 214 and into the associated canaliculus 208, 210 (FIG. 2). In this example, the lacrimal implant 900 can comprises an implant body 902 including first 904 and second 906 portions, and can extend from a proximal end 908 of the first portion 904 to a distal end 910 of the second portion 906. The proximal end 908 can define a longitudinal proximal axis 912 and the distal end 910 can define a longitudinal distal axis 914. The implant body 900 can be configured such that, when implanted, an angled intersection of approximately 90 degrees exists between the proximal axis 912 and the distal axis 914 for biasing at least a portion of the implant body against at least a portion of the lacrimal canaliculus 208, 210 (FIG. 2) located at or more distal to a canaliculus curvature 250 (FIG. 2).

As shown, a smooth transition can exist between the first 904 and second 906 portions. In this example, the smooth transition can include an insertion-facilitating depression 975 or other gripping means to aid in one or both of implant insertion or removal. Also in this example, the implant body 902 can include a graspable or other projection 932, such as an annular projection extending laterally from, and completely around, the proximal end 908. In some examples, the graspable or other projection 932 includes a partially trimmed projection extending varying amounts around the proximal end 908.

Figure 10A:
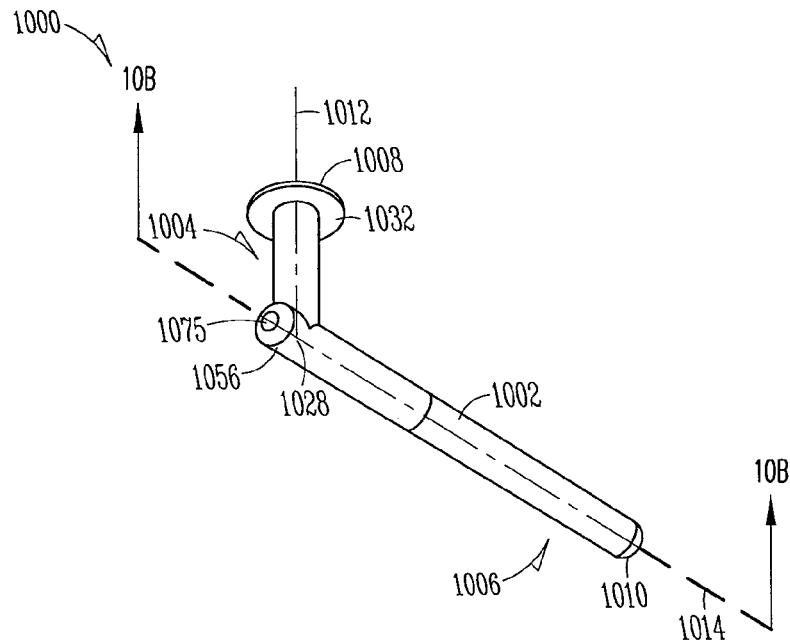
FIG. 10A illustrates an isometric view of an example lacrimal implant configured to be retained within a lacrimal punctum and associated canalicular anatomy, the lacrimal implant including a portion disposable within a lacrimal canaliculus ampulla.
Figure 10B:
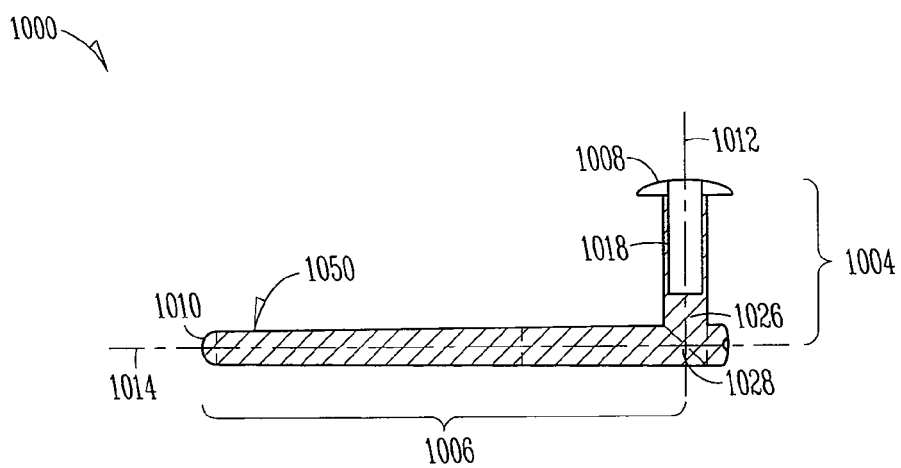
FIG. 10B illustrates a cross-sectional view of an example lacrimal implant taken along a line parallel to a longitudinal axis of the implant, such as along line 10B-10B.
Figure 11:
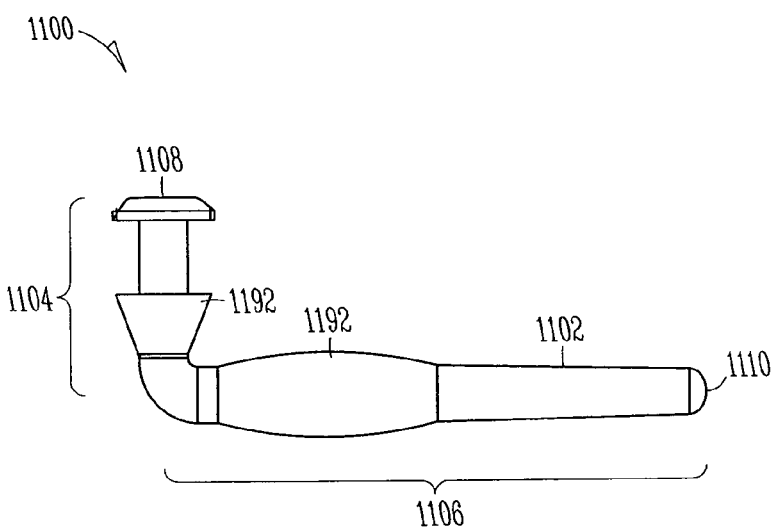
FIGS. 11-17 illustrate side or isometric views of various lacrimal implant examples configured to be retained within a lacrimal punctum and associated canalicular anatomy, each lacrimal implant including at least one intermediately-disposed retainment projection.

FIGS. 10A-10B illustrate another lacrimal implant 1000 example that is insertable through a lacrimal punctum 212, 214 and into the associated canaliculus 208, 210 (FIG. 2). In this example, the lacrimal implant 1000 can comprises an implant body 1002 including first 1004 and second 1006 portions, and can extend from a proximal end 1008 of the first portion 1004 to a distal end 1010 of the second portion 1006. The proximal end 1008 can define a longitudinal proximal axis 1012 and the distal end 1010 can define a longitudinal distal axis 1014. The implant body 1000 can be configured such that, when implanted, an angled intersection of approximately 90 degrees exists between the proximal axis 1012 and the distal axis 1014 for biasing at least a portion of the implant body against at least a portion of the lacrimal canaliculus 208, 210 (FIG. 2) located at or more distal to a canaliculus curvature 250 (FIG. 2).

In this example, a proximal end 1028 of the second implant body portion 1006 can include a retention element 1056 configured to bias against at least a portion of a lacrimal canaliculus ampulla 252 (FIG. 2) when implanted. The retention element 1056 can include an insertion-facilitating depression 1075 or other gripping means to aid in one or both of implant insertion or removal. In this example, the implant body 1002 includes a first cavity 1018 configured to receive a first drug-releasing or other agent-releasing drug insert, disposed near the proximal end 1008 of the first implant body portion 1004. Also in this example, the implant body 1002 can include a graspable or other projection 1032, such as an annular projection having a diameter of about 1.3 millimeters extending laterally from, and completely around, the proximal end 1008. In some examples, the graspable or other projection 1032 includes a partially trimmed projection extending varying amounts around the proximal end 1008.

FIG. 10B illustrates an example cross-sectional view of the lacrimal implant 1000 taken along a line parallel to a longitudinal axis of the implant, such as along line 10B-10B of FIG. 10A. As shown in FIG. 10B, a distal end 1026 of the first portion 1004 can be integral with the second portion 1006 at or near a proximal end 1028 of the second portion 1006. In various examples, the second portion 1006 can include a longitudinal length, as measured from the proximal axis 1012 to the distal end 1010, having a magnitude less than four times a longitudinal length of the first portion 1004, as measured from the proximal end 1008 to the distal axis 1014. In some examples, the first portion can include a longitudinal length of about 1.5 millimeters and the second portion can include a longitudinal length of about 5 millimeters.

In various examples, the second portion 1006 can comprise an integral dilator 1050 to dilate anatomical tissue, such as one or both of the lacrimal punctum 212, 214 (FIG. 2) or associated canaliculus 208, 210, to a sufficient diameter as the lacrimal implant 1000 is being implanted. In some examples, the second portion 1006 tapers from a proximal end 1028 diameter of about 0.46 millimeters to a dilator tip 1054 diameter of about 0.36 millimeters.

FIGS. 11-17 illustrate examples of other lacrimal implants 1100, 1200, 1300, 1400, 1500, 1600, 1700 that are insertable through a lacrimal punctum 212, 214 and into the associated canaliculus 208, 210 (FIG. 2). In these examples, each lacrimal implant 1100, 1200, 1300, 1400, 1500, 1600, 1700 can comprises an implant body 1102, 1202, 1302, 1402, 1502, 1602, 1702 including first 1104, 1204, 1304, 1404, 1504, 1604, 1704 and second 1106, 1206, 1306, 1406, 1506, 1606, 1706 portions, and can extend from a proximal end 1108, 1208, 1308, 1408, 1508, 1608, 1708 of the first portion 1104, 1204, 1304, 1404, 1504, 1604, 1704 to a distal end 1110, 1210, 1310, 1410, 1510, 1610, 1710 of the second portion 1106, 1206, 1306, 1406, 1506, 1606, 1706. Each implant body 1102, 1202, 1302, 1402, 1502, 1602, 1702 can include at least one intermediately-disposed retainment projection 1192, 1292, 1392, 1492, 1592, 1692, 1792 to potentially further secure an implanted position of the lacrimal implants. The intermediately-disposed retainment projections 1192, 1292, 1392, 1492, 1592, 1692, 1792 can be positioned on one or both of the first 1104, 1204, 1304, 1404, 1504, 1604, 1704 or second 1106, 1206, 1306, 1406, 1506, 1606, 1706 implant body portions, and can take the form of annular, semi-annular, column-like or barrel-like projection. The intermediately-disposed retainment projections 1192, 1292, 1392, 1492, 1592, 1692, 1792 can include a cross-sectional size greater than adjacent implant body portions and can slightly deform a portion of a canalicular wall to provide the added securement to keep the implants in place for the duration of use (see, e.g., FIG. 5).

It is believed that the occlusion of the lower lacrimal canaliculus 210, for example, by a lacrimal implant may cause back pressure to build-up within the canaliculus 210, thereby urging the implant from an implanted position. It is thought that this back pressure could, for example, occur during a blink (where tears are being pumped from an anterior surface of the eye down a drainage system) or a sneeze (where pressure is emanating up from the pulmonary system). Accordingly, one of more of the additional retention features now shown in the form of at least one intermediately-disposed retainment projection 1192, 1292, 1392, 1492, 1592, 1692, 1792 may be used to prevent implant migration and further secure an implanted lacrimal implant position. These additional retention features can be designed to prevent migration in the proximal direction while not increasing implant implantation difficultly an appreciable degree.

Ongoing clinical trials are performed to evaluate the safety, tolerability, comfort, ease of handling and insertion/removal, retention, efficacy and dosing of the various lacrimal implants disclosed in this patent document. Preliminary reports indicate the lacrimal implants, such as the lacrimal implants shown in FIGS. 12, 13 and 43A-43C, are effective and well tolerated by patients participating in the trials. For instance, based on preliminary data measured at 4 weeks of follow-up following placement of the lacrimal implants of the type shown in FIG. 13, the overall adverse events range from only 1.7% to 11.7%, when adverse events were noted. The most common adverse events are eye itching (commonly seen with initial implant wear and usually a part of adaptation), lacrimation and eye irritation (11.7%, 6.7% and 5.0%, respectively). Other adverse events with less reported frequency than the former include burning, ocular discomfort, superficial punctate keratitis. No conjunctival or ocular hyperemia was observed at 4 weeks of follow-up. Week-4 patient-reported comfort and tearing scores for the implant including the 44-µg latanoprost drug insert were as follows: 88% of patients rated comfort as 'no awareness' or 'mild awareness,' while 76% of patients rated tearing as 'none.' Physician handling assessments of lacrimal implants of the type shown in FIGS. 12, 13 and 43A-43C indicate that the implants are easy to insert and remove, with physicians rating lacrimal implants of the type shown in FIGS. 12 and 43A-43C as easy to insert (80%) and remove (100%).

Figure 12:
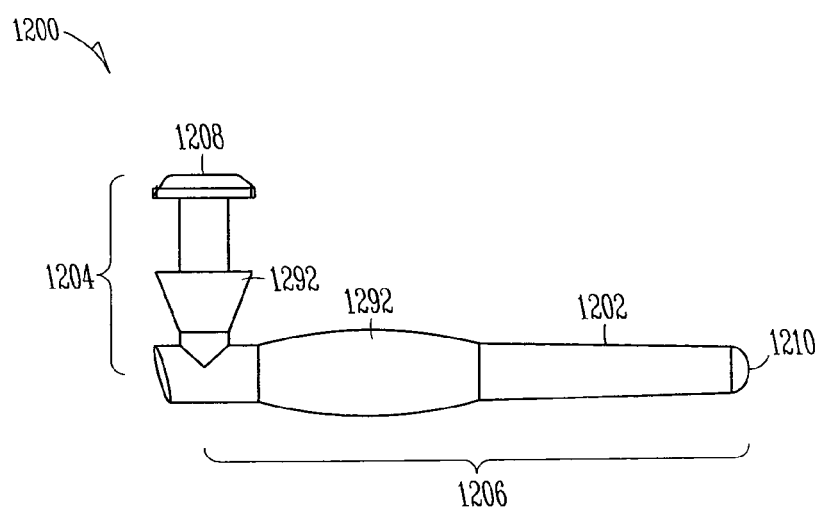
Figure 13:
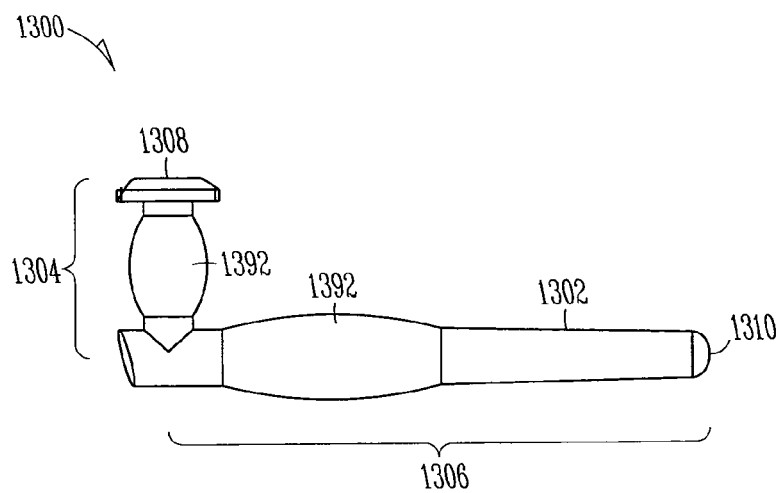
Figure 14:
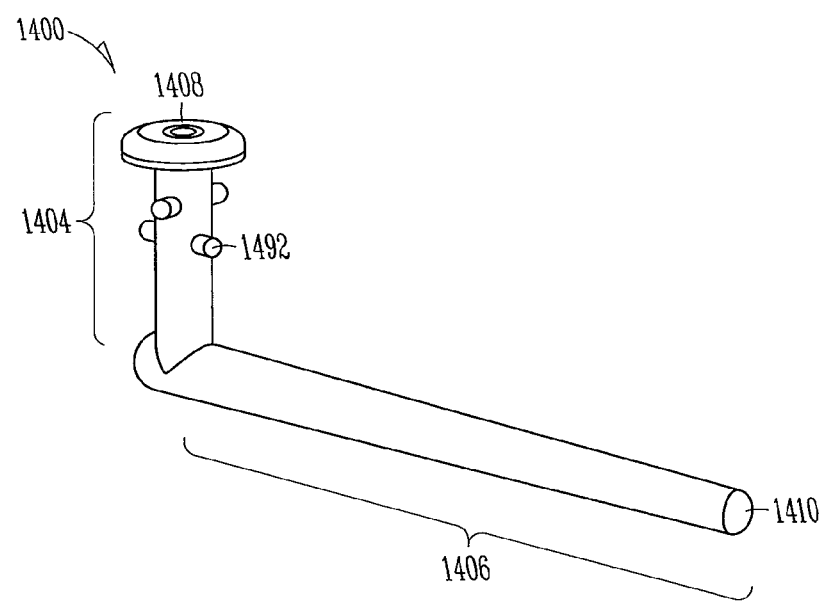
Figure 15:
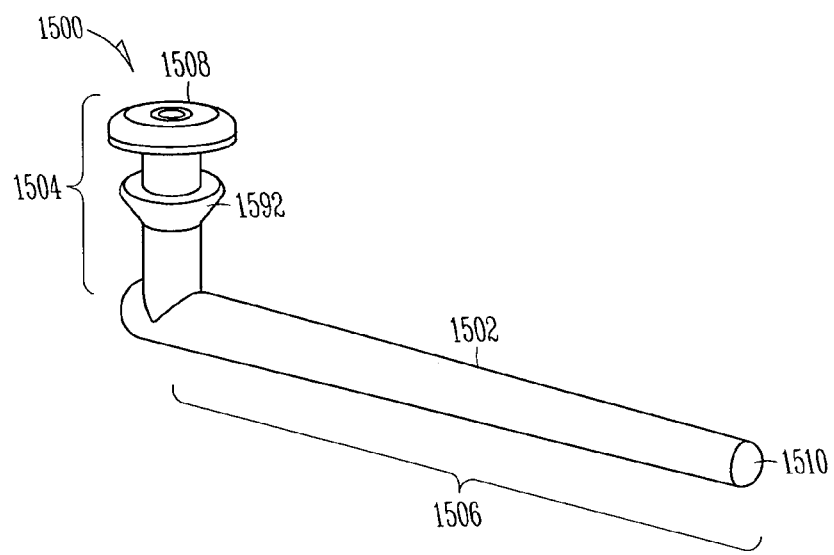
Figure 16:
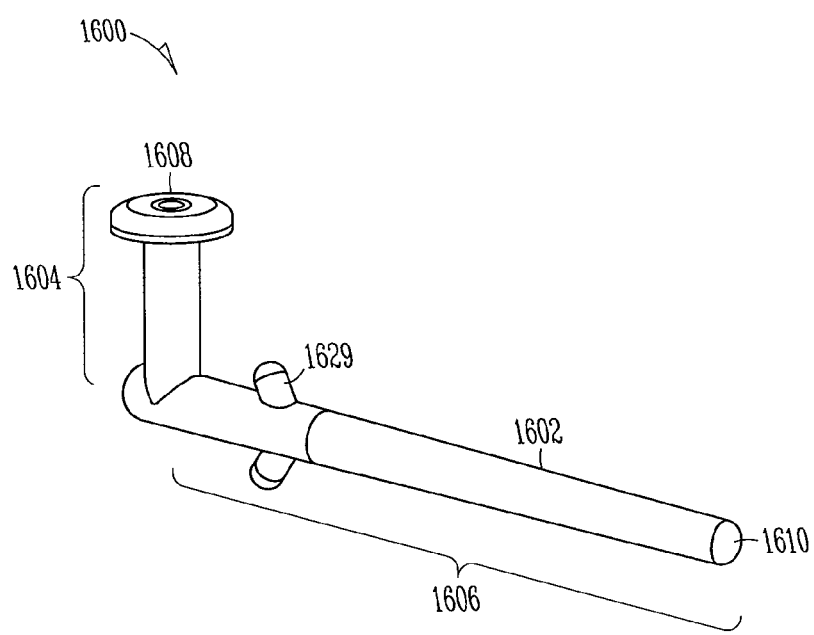
Figure 17:
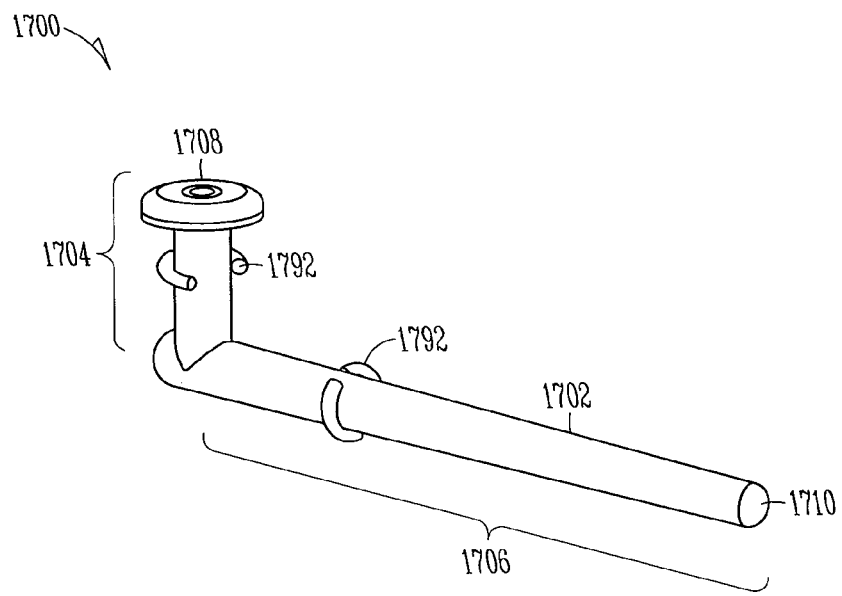

In an example, as shown generally in FIG. 12, the proximal end 1208 can provide a projection such as a cap having an outer diameter of about 1.2 mm, and a cap thickness of between about 0.13 mm to about 0.19 mm in a longitudinal direction of the first portion 1204. In this example, the proximal end 1208 cap portion can be separated from the retainment projection 1292 of the first portion 1204, such as by a shaft portion that can have an outer diameter of about 0.56 mm and a longitudinal shaft length of about 0.6 mm. In this example, the retainment projection 1292 of the first portion 1204 can have a proximal outer diameter of about 0.9 mm, which can taper down to a distal outer diameter (such as where the first portion 1204 and the second portion 1206 meet) that is less than or equal to the outer diameter of the shaft portion. Better retention may be obtained with a more sharply tapered retainment projection 1292 of the first portion 1204, which, in another example, can instead have a proximal outer diameter of about 1.1 mm. In still another example, the proximal end 1208 can instead provide a cap having an outer diameter of about 1.4 mm and the proximal outer diameter of the retainment projection 1292 of the first portion 1204 can instead be about 1.4 mm.

Similar dimensions and dimensional variations can be applied to the other examples described herein, including the examples shown generally in FIGS. 11-17. For instance, as shown generally in FIG. 13, the retainment projection 1392 of the first portion 1304 can barrel outward from a starting diameter of about 0.56 mm to about 0.70 mm. The first cavity within the first portion 1304 can have a diameter of about 0.42 mm (approx. 0.0165 inches) and a depth of about 1.22 mm (approx. 0.048 inches). Such a first cavity size can result in a first portion wall thickness surrounding the cavity of at least about 0.07 mm. In some examples, a drug insert having about 44 micrograms (µg) of latanoprost (assuming approx. 33% drug load) is inserted into and secured within the first cavity. Optionally, more or less drug or other agent can be inserted within the first cavity by increasing or decreasing the size (e.g., diameter or depth), respectively, of the cavity and the drug insert that can be placed therein. As an example, as shown and described in association with FIGS. 43A-43C, the first cavity can have a diameter of about 0.56 mm (approx. 0.022 inches) and a depth of 1.22 mm (approx. 0.048 inches). Such a first cavity size can receive a drug insert having about 81 µg of latanoprost (assuming approx. 33% drug load).

Figure 18:
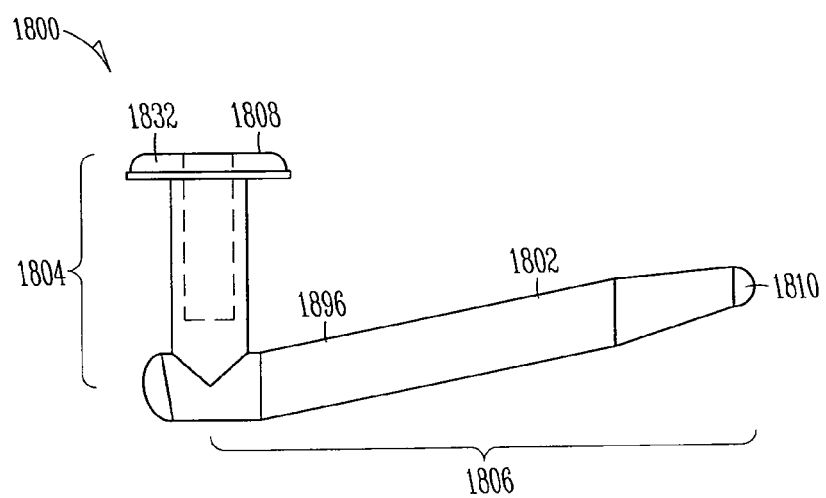
FIGS. 18-19 illustrate example lacrimal implants configured to be retained within a lacrimal punctum and associated canalicular anatomy, each lacrimal implant including a non-linear second implant body portion.
Figure 19:
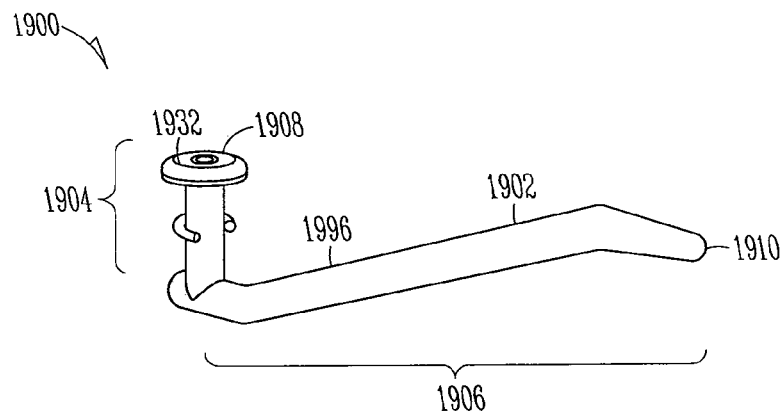

FIGS. 18-19 illustrate examples of other lacrimal implants 1800, 1900 that are insertable through a lacrimal punctum 212, 214 and into the associated canaliculus 208, 210 (FIG. 2). In these examples, each lacrimal implant 1800, 1900 can comprise an implant body 1802, 1902 including first 1804, 1904 and second 1806, 1906 portions, and can extend from a proximal end 1808, 1908 of the first portion 1804, 1904 to a distal end 1810, 1910 of the second portion 1806, 1906. As shown, an intermediate portion 1896, 1996 of each implant body 1802, 1902 can be angled relative to one or both of the first 1804, 1904 or second 1806, 1906 implant body portions to potentially further secure an implanted position of the lacrimal implants.

It is believed that the angling of the intermediate portion 1896, 1996 may help capture the anatomy of the lacrimal punctum 212, 214 and canaliculus 208, 210 to keep the lacrimal implants 1800, 1900 in an implanted position, such as via a directional force applied by the angling against the lacrimal canaliculus. This directional force can be designed to continuously urge a feedback or other projection 1832, 1932 flush with the punctum 212, 214.

Figure 20:
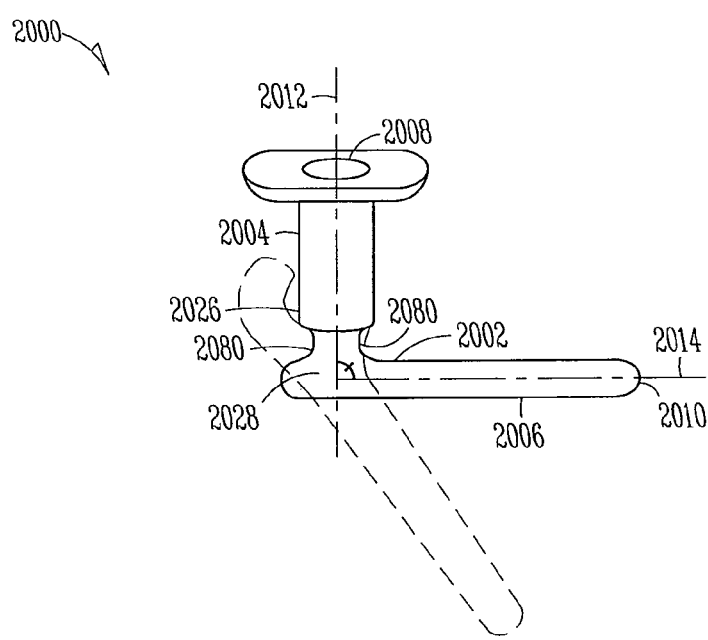
FIG. 20 illustrates an example lacrimal implant configured to be retained within a lacrimal punctum and associated canalicular anatomy, the lacrimal implant including one or more material cutouts allowing for flexure of a second body portion.
Figures 21A, 21B:
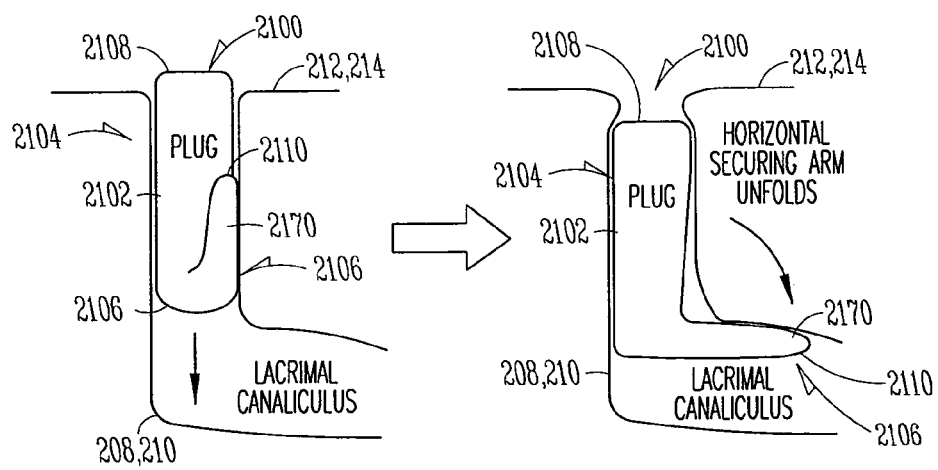
Figures 22A, 22B:
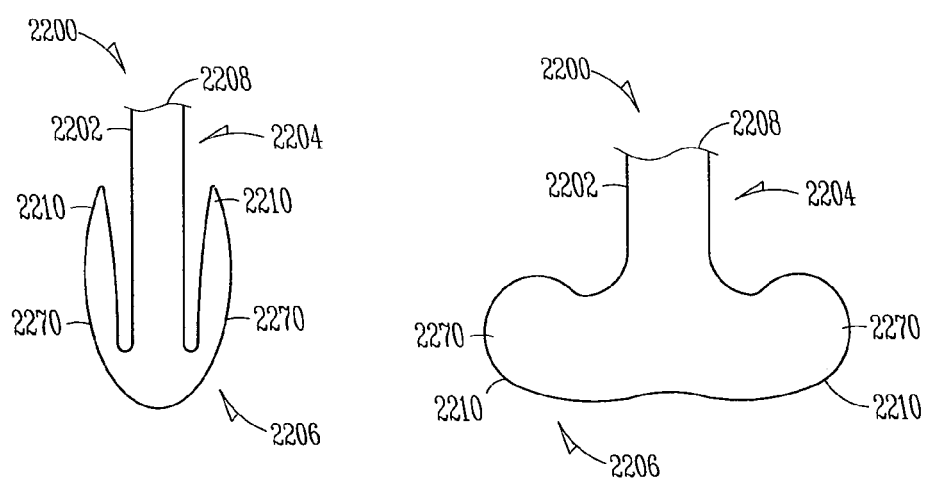

FIG. 20 illustrates another lacrimal implant 2000 example that is insertable through a lacrimal punctum 212, 214 and into the associated canaliculus 208, 210 (FIG. 2). In this example, the lacrimal implant 2000 can comprises an implant body 2002 including first 2004 and second 2006 portions, and can extend from a proximal end 2008 of the first portion 2004 to a distal end 2010 of the second portion 2006. The proximal end 2008 can define a longitudinal proximal axis 2012 and the distal end 2010 can define a longitudinal distal axis 2014. The implant body 2000 can be configured such that, when implanted, an angled intersection of approximately 90 degrees exists between the proximal axis 2012 and the distal axis 2014 for biasing at least a portion of the implant body against at least a portion of a lacrimal canaliculus 208, 210 (FIG. 2) located at or more distal to a canaliculus curvature 250 (FIG. 2). In various examples, a distal end 2026 of the first portion 2004 can be integral with the second portion 2006 at or near a proximal end 2028 of the second portion 2006.

In this example, one or more material cutouts 2080 are made in an outer surface of the implant body 2002. As a result, the angled intersection between the proximal axis 2012 and the distal axis 2014 can become more linearly aligned during implant, as shown in phantom, to facilitate insertion through the lacrimal punctum 212, 214 and into the associated canaliculus 208, 210.

FIGS. 21A-21B and 22A-22B illustrate examples of a side view of other lacrimal implants 2100, 2200 that are insertable through a lacrimal punctum 212, 214 and into the associated canaliculus 208, 210 (FIG. 2). In these examples, each lacrimal implant 2100, 2200 can comprises an implant body 2102, 2202 including first 2104, 2204 and second 2106, 2206 portions, and can extend from a proximal end 2108, 2208 of the first portion 2104, 2204 to a distal end 2110, 2210 of the second portion 2106, 2206. Each second portion 2106, 2206 can include one or more arm members 2170, 2270 movable between a first configuration, in which the one or more arm members 2170, 2270 are adjacent the implant body, and a second configuration, in which the one or more arm members 2170, 2270 laterally extend from a side of the implant body. In the first configuration, the one or more arm members 2170, 2270 facilitate insertion of the lacrimal implant through the lacrimal punctum 212, 214 and into the associated canaliculus 208, 210 by providing a narrow profile. In the second configuration, the one or more arm members 2170, 2270 laterally extend to fill at least one of a lacrimal canaliculus ampulla 252 (FIG. 2) or the canaliculus 208, 210 when implanted. Optionally, the one or more arm members 2170, 2270 can include a fluid swellable material, such as hydrogel, to further secure an implanted lacrimal implant within the lacrimal ampulla 252 or canaliculus 208, 210 when hydrated.

In some examples, the one or more arm members 2170, 2270 can be incorporated into a mold that is also used to form the implant body 2102, 2202. The one or more arm members 2170, 2270 can alternatively be attached by molding or gluing onto an existing implant body 2102, 2202. Different thicknesses and shapes for the one or more arm members 2170, 2270 can be employed for different stiffness and securing/removal characteristics. Beyond hydrogel, the one or more arm members 2170, 2270 can be made of other materials, such as those used for the haptics on the intraocular lenses or the like.

Figures 23A, 23B:
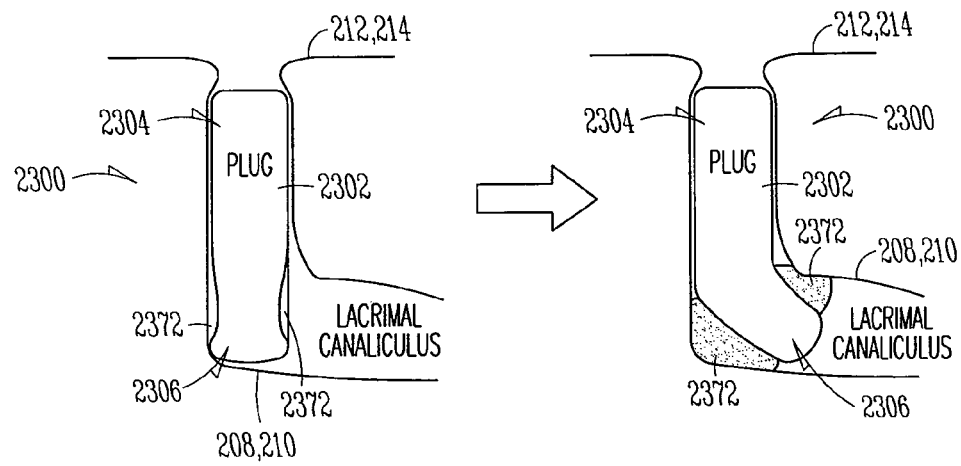
FIGS. 23A-23B illustrate a side view of an example lacrimal implant configured to be retained within a lacrimal punctum and associated canalicular anatomy, the lacrimal implant including an expandable retention element disposed around one or more portions of the implant body.

FIGS. 23A-23B illustrate an example side view of another lacrimal implant 2300 that is insertable through a lacrimal punctum 212, 214 and into the associated canaliculus 208, 210 (FIG. 2). In this example, the lacrimal implant 2300 can comprises an implant body 2302 including first 2304 and second 2306 portions, and can extend from a proximal end 2308 of the first portion 2304 to a distal end 2310 of the second portion 2306. The second portion 2306 can be surrounded, at least in part, by an expandable retention element (e.g., an inflatable balloon) 2372, which is configured to bias the second portion 2306 away from a lacrimal canaliculus wall upon expansion.

In some examples, the expandable retention element 2372 contains or can be inflated by an agent to be delivered to a tissue of the eye or nasolacrimal system. In some examples, the expandable retention element 2372 can employ one or more balloons which are separate from any drug insert or other agent retaining structure. The one or more balloons may optionally be similar to those used on balloon catheters, with an inflation lumen or the like optionally being included in an implant insertion tool so as to allow controlled inflation of the balloon. In such an example, the lacrimal implant 2300 may be inserted with the balloons deflated, as shown in FIG. 23A. Once the lacrimal implant 2300 is in place, the balloons can then inflated to secure an implanted position of the implant, as shown in FIG. 23B.

The balloons can also be deflatable to make removal of the lacrimal implant 2300 easier. The balloons can optionally partially or substantially conform to variations in the size and shape of the canaliculus 208, 210. Alternative examples of balloons may be inflated by swelling of a material disposed within the balloon, such as swelling of a hydrogel by absorption of water through perforations or openings in the balloon. The one or more balloons can be annular structures disposed around the supporting implant body, or may be disposed eccentrically about an axis of the implant body. As illustrated in FIG. 23B, the balloons may be disposed sufficiently distal to reside within or adjacent a horizontal portion of the tear drainage duct, within or adjacent a lacrimal ampulla of the tear drainage system, or the like. Alternative examples can include one or more balloons which are more proximal.

Figure 24:
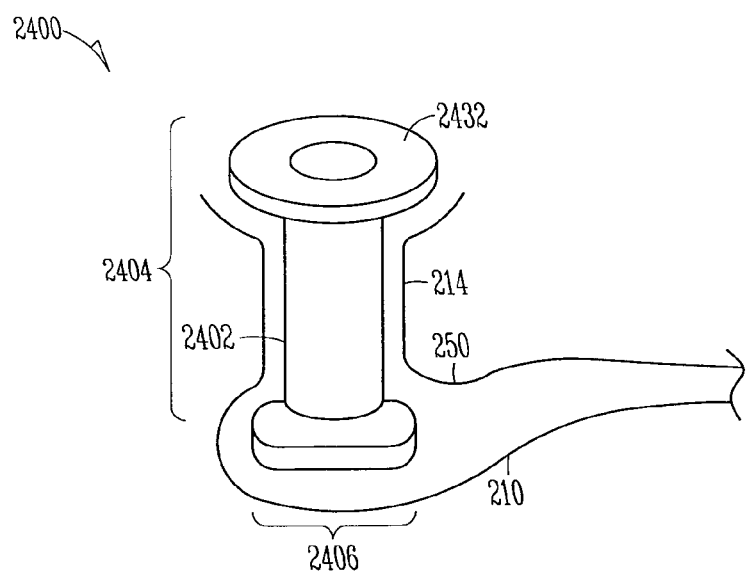
FIG. 24 illustrates a schematic view of an example lacrimal implant retained within a lacrimal punctum and associated canalicular anatomy.

FIG. 24 illustrates an example schematic view of another lacrimal implant 2400 implanted through a lower lacrimal punctum 214 and into the associated canaliculus 210. The lacrimal implant 2400 can comprise an implant body 2402 including first 2404 and second 2406 portions. In various examples, the implant body 2402 can be configured such that, when implanted, at least a portion of the implant body 2402 is biased against at least a portion of the lacrimal canaliculus 210 located at or more distal to a canaliculus curvature 250 to securely retain an implanted position of the implant 2400. In this example, the second portion 2406 includes a longitudinal length less than about 2 millimeters, such as a size greater than a diameter of the first portion 2404, but less than 2 millimeters. Also in this example, the implant body 2402 can include a graspable or other projection 2432, such as extending laterally at least partially around a proximal end of the first implant body portion 2404.

Figure 25A:
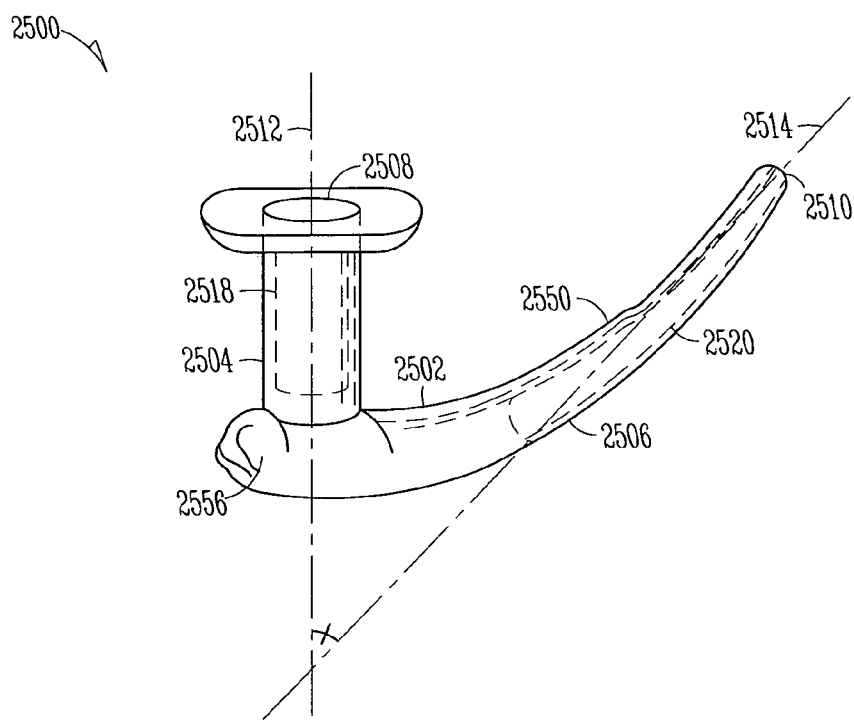
FIGS. 25A-25B illustrate an isomeric view of example lacrimal implants configured to be retained within a lacrimal punctum and associated canalicular anatomy, each lacrimal implant including an implant body portion having a generally concave shape.
Figure 25B:
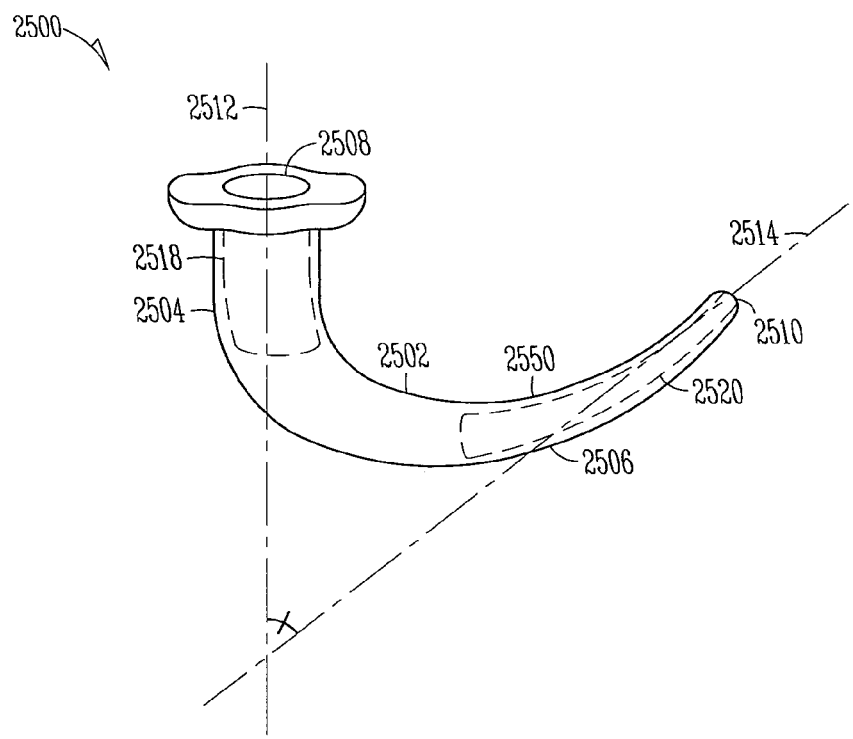

FIGS. 25A-25B illustrate examples of another lacrimal implant 2500 that is insertable through a lacrimal punctum 212, 214 and into the associated canaliculus 208, 210 (FIG. 2). In these examples, the lacrimal implant 2500 can comprise an implant body 2502 including first 2504 and second 2506 portions, and can extend from a proximal end 2508 of the first portion 2504 to a distal end 2510 of the second portion 2506. The implant body can include a general shape, which can generally match the anatomical features of a canaliculus 208, 210 to provide patient comfort and secure retainment, for example. The proximal end 2508 can define a longitudinal proximal axis 2512 and the distal end 2510 can define a longitudinal distal axis 2514. The implant body 2502 can be configured such that, when implanted, an angled intersection of between 45-90 degrees exists between the proximal axis 2512 and the distal axis 2514 such as for biasing at least a portion of the implant body 2502 against at least a portion of a lacrimal canaliculus 208, 210 (FIG. 2) located at or more distal to a canaliculus curvature 250 (FIG. 2).

Figure 26:
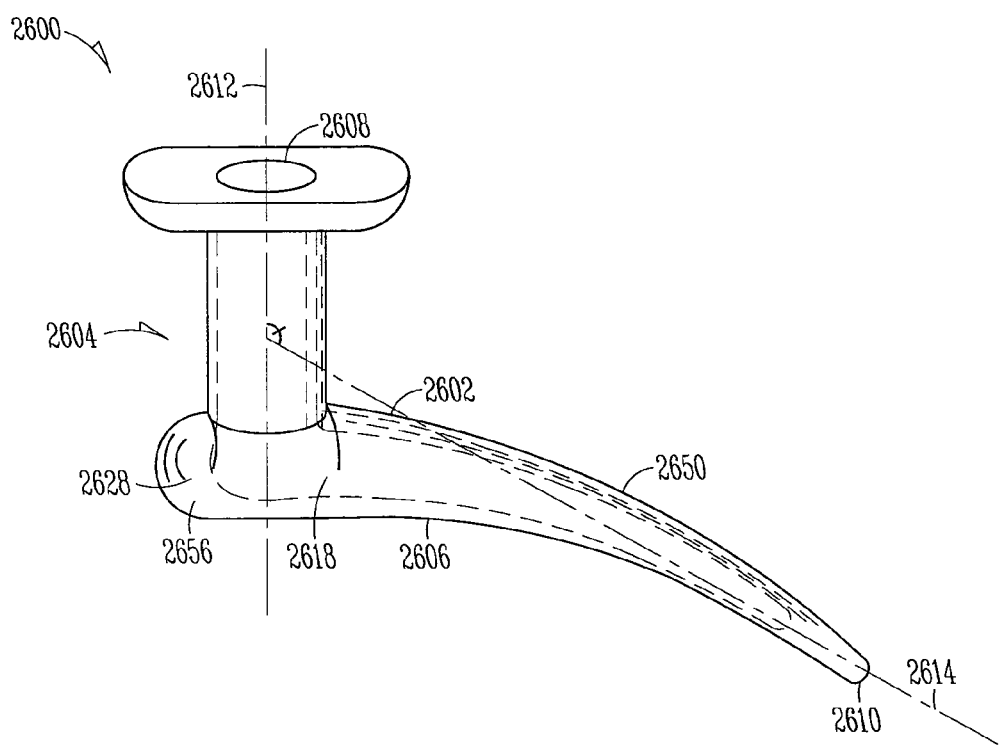
FIG. 26 illustrates an isometric view of an example lacrimal implant configured to be retained within a lacrimal punctum and associated canalicular anatomy, the lacrimal implant including an implant body portion having a generally convex shape.

In the examples of FIGS. 25A-25B, the implant body 2502 includes both of a first cavity 2518 disposed near the proximal end 2508 and a second cavity 2520 disposed near the distal end 2510. The first cavity 2518 extends inward from the proximal end 2508 of the first portion 2504, and the second cavity 2520 extends inward from the distal end 2510 of the second portion 2506. A first drug-releasing or other agent-releasing drug insert can be disposed in the first cavity 2518 to provide a sustained drug or other therapeutic agent release to an eye, while a second drug-releasing or other agent-releasing drug insert can be disposed in the second cavity 2520 to provide a sustained drug or other therapeutic agent release to a nasal passage or inner ear system, for example. In some examples, the first cavity 2518 can extend inward from the proximal end 2508 of the first portion 2504 to a position near the distal end 2510 of the second portion 2506, such as is shown in FIG. 26, and is filled with a first drug-releasing or other agent-releasing drug insert. In some examples, the second cavity 2520 can extend inward from the distal end 2510 of the second portion 2506 to a position near the proximal end 2508 of the first portion 2504 and is filled with a second drug-releasing or other agent-releasing drug insert.

In certain examples, the second portion 2506 comprises an integral dilator 2550 to dilate anatomical tissue, such one or both of the lacrimal punctum 212, 214 or canaliculus 208, 210, to a sufficient diameter as the lacrimal implant 2500 is being implanted. In this way, the lacrimal implant 2500 can be implanted in various size ocular anatomies without the need for pre-dilation via a separate enlarging tool. In these examples, the integral dilator 2550 includes a generally concave shape related to the first portion 2504. In some examples, the concave shape includes a radius less than a radius of the canaliculus curvature 250. In some examples, the concave shape includes a radius substantially the same as the radius of the canaliculus curvature 250. As shown in the example of FIG. 25B, a smooth transition can exist between the first 2504 and second 2506 portions.

In certain examples, a proximal end 2528 of the second implant body portion 2506 can include a retention element 2556 configured to bias against at least a portion of a lacrimal canaliculus ampulla 252 (FIG. 2) when implanted. In the example of FIG. 25A, the retention element 2556 projects proximally from the intersection between the first 2504 and second 2506 implant body portions.

FIG. 26 illustrates another lacrimal implant 2600 example that is insertable through a lacrimal punctum 212, 214 and into the associated canaliculus 208, 210 (FIG. 2). In this example, the lacrimal implant 2600 comprises an implant body 2602 including first 2604 and second 2606 portions, and extends from a proximal end 2608 of the first portion 2604 to a distal end 2610 of the second portion 2606. The proximal end 2608 can define a longitudinal proximal axis 2612 and the distal end 2610 can define a longitudinal distal axis 2614. The implant body 2600 can be configured such that, when implanted, an angled intersection of between 90-135 degrees exists between the proximal axis 2612 and the distal axis 2614 for biasing at least a portion of the implant body against at least a portion of a lacrimal canaliculus 208, 210 located at or more distal to a canaliculus curvature 250 (FIG. 2).

In certain examples, the implant body 2602 can include a first cavity 2618 disposed near the proximal end 2608. In this example, the first cavity 2618 extends inward from the proximal end 2608 of the first portion 2604 to a position near the distal end 2610 of the second portion 2606. A first drug-releasing or other agent-releasing drug insert having a volume between about 0.2 cubic centimeters to about 0.25 cubic centimeters, for example, can be disposed in the first cavity 2618 to provide a extended sustained drug or other therapeutic agent release to an eye.

In certain examples, the second portion 2606 comprises an integral dilator 2650 to dilate anatomical tissue, such one or both of the lacrimal punctum 212, 214 or canaliculus 208, 210, to a sufficient diameter as the lacrimal implant 2600 is being implanted. In this way, the lacrimal implant 2600 can be implanted in various size ocular anatomies without the need for pre-dilation via a separate enlarging tool. In this example, the dilator 2650 includes a generally convex shape relative to the first portion 2604. In some examples, the convex shape includes a radius less than a radius of the canaliculus curvature 250. In some examples, the convex shape includes a radius substantially the same as the radius of the canaliculus curvature 250.

Figure 29:
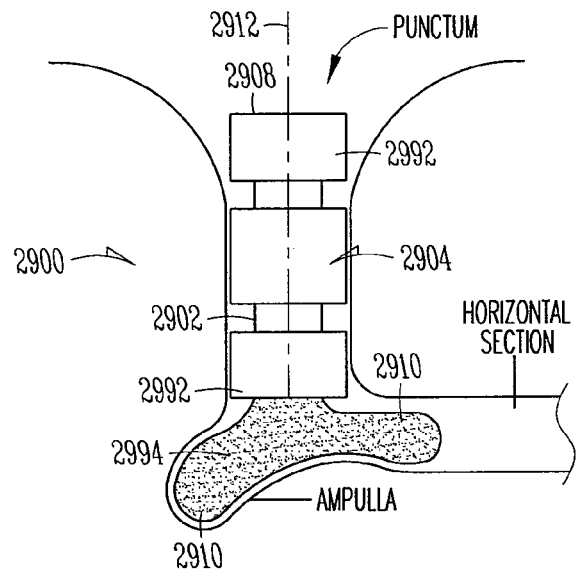
FIGS. 29-32 illustrate side views of various lacrimal implant examples configured to be retained within a lacrimal punctum and associated canalicular anatomy, each lacrimal implant including a fluid swellable retention element.
Figure 30:
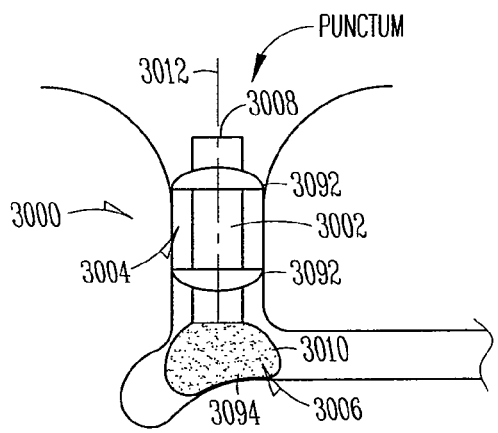
Figure 31:
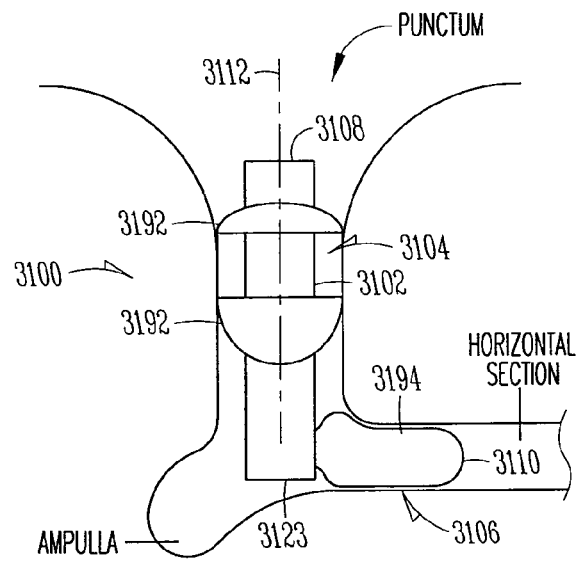
Figure 32:
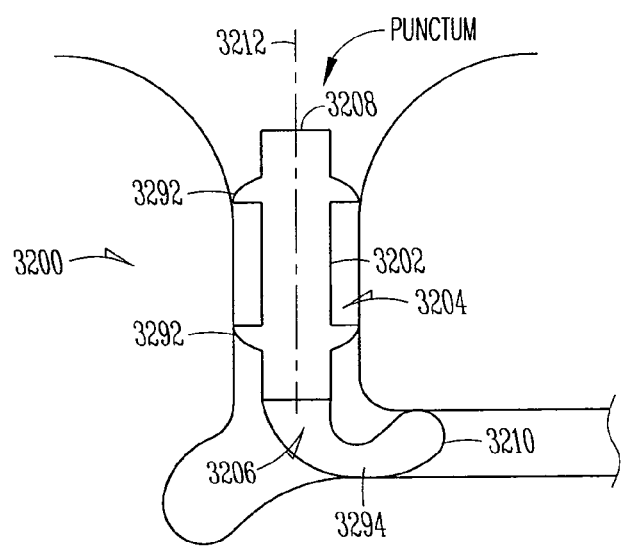

In certain examples, a proximal end 2628 of the second implant body portion 2606 can include a retention element 2656 configured to bias against at least a portion of a lacrimal canaliculus ampulla 252 (FIG. 2) when implanted. In this example, the retention element 2656 projects proximally from the intersection between the first 2604 and second 2606 implant body portions. In some examples, such as is shown in FIGS. 29-30, a proximal end 2628 of the second implant body portion 2606 can include a retention element 2656 comprising a hydrogel retention element, which is configured to expand into the ampulla 252 when the implant body 2602 is implanted.

Figure 27:
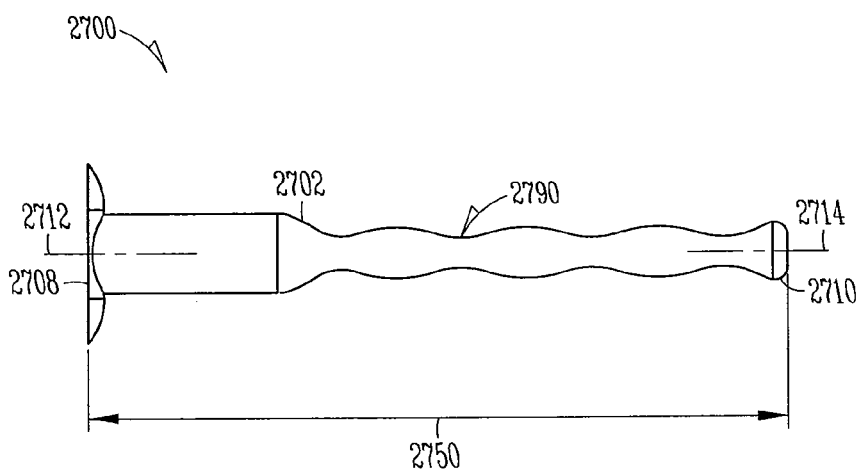
FIG. 27 illustrates a side view of an example lacrimal implant configured to be retained within a lacrimal punctum and associated canalicular anatomy, the lacrimal implant including an implant body portion having an undulating shape.

FIG. 27 illustrates an example side view of another lacrimal implant 2700 that is insertable through a lacrimal punctum 212, 214 and into the associated canaliculus 208, 210 (FIG. 2). In this example, the lacrimal implant 2700 comprises an implant body 2702 including first and second portions, which prior to implant, are linear relative to one another. The implant body 2702 extends from a proximal end 2708 of the first portion to a distal end 2710 of the second portion. The proximal end 2708 can define a longitudinal proximal axis 2712 and the distal end 2710 can define a longitudinal distal axis 2714. The implant body 2702 can be configured such that, when implanted, an angled intersection of between 45-135 degrees exists between the proximal axis 2712 and the distal axis 2714 such as for biasing at least a portion of the implant body 2702 against at least a portion of a lacrimal canaliculus 208, 210 (FIG. 2) located at or more distal to a canaliculus curvature 250 (FIG. 2). In this example, the second portion of the implant body 2702 includes at least one undulation 2790 to facilitate the biasing of the implant body 2702 against the portion of the lacrimal canaliculus 208, 210.

Figure 28:
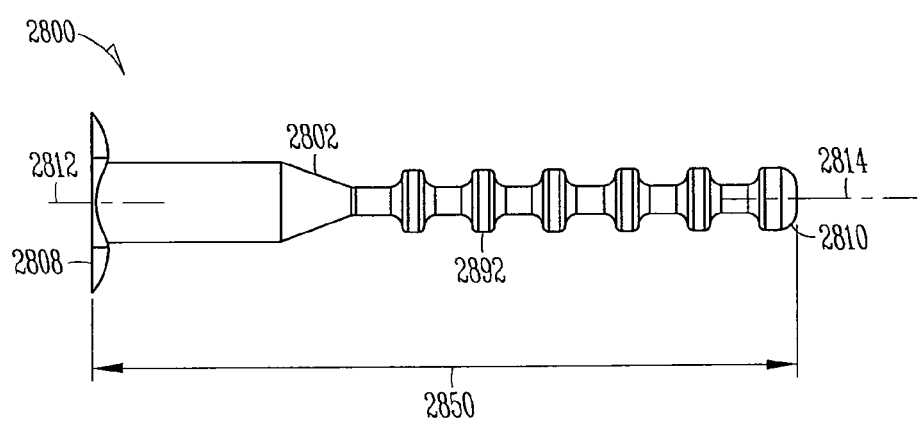
FIG. 28 illustrates a side view of an example lacrimal implant configured to be retained within a lacrimal punctum and associated canalicular anatomy, the lacrimal implant including at least one intermediately-disposed retainment projection.

FIG. 28 illustrates an example side view of another lacrimal implant 2800 that is insertable through a lacrimal punctum 212, 214 and into the associated canaliculus 208, 210 (FIG. 2). In this example, the lacrimal implant 2800 comprises an implant body 2802 including first and second portions, which prior to implant, are linear relative to one another. The implant body 2802 extends from a proximal end 2808 of the first portion to a distal end 2810 of the second portion. The proximal end 2808 can define a longitudinal proximal axis 2812 and the distal end 2810 can define a longitudinal distal axis 2814. The implant body 2802 can be configured such that, when implanted, an angled intersection of between 45-135 degrees exists between the proximal axis 2812 and the distal axis 2814 for biasing at least a portion of the implant body 2802 against at least a portion of a lacrimal canaliculus 208, 210 (FIG. 2) located at or more distal to a canaliculus curvature 250 (FIG. 2). In this example, the second portion of the implant body 2802 includes at least one intermediately-disposed retainment projection 2892, such an annular rib-like projection. The retainment projection 2892 includes a cross-sectional size greater than an adjacent implant body portion and can facilitate the securement of an implanted position of the implant body 2802, while the adjacent narrower implant body portion can facilitate the biasing of the implant body 2802 against the portion of the lacrimal canaliculus 208, 210.

FIGS. 29-32 illustrate examples of a side view of other lacrimal implants 2900, 3000, 3100, 3200 that are insertable through a lacrimal punctum 212, 214 and into the associated canaliculus 208, 210 (FIG. 2). In these examples, each lacrimal implant 2900, 3000, 3100, 3200 can comprise an implant body 2902, 3002, 3102, 3202 including first 2904, 3004, 3104, 3204 and second 2906, 3006, 3106, 3206 portions, and can extend from a proximal end 2908, 3008, 3108, 3208 of the first portion 2904, 3004, 3104, 3204 to a distal end 2910, 3010, 3110, 3210 of the second portion 2906, 3006, 3106, 3206. The proximal end 2908, 3008, 3108, 3208 can define a longitudinal proximal axis 2912, 3012, 3112, 3212.

The second portion 2906, 3006, 3106, 3206 can include a fluid swellable retention element 2994, 3094, 3194, 3294 configured to expand laterally, relative to the proximal axis 2912, 3012, 3112, 3212, when the implant body 2902, 3002, 3102, 3202 is implanted. In various examples, the fluid swellable retention element 2994, 3094, 3194, 3294 can be formed such that one or both of expansion direction or expansion amount can be controlled. For instance, the fluid swellable retention element 2994, 3094, 3194, 3294 can expand more in one plane than another to securely anchor the lacrimal implants. In some examples, the fluid swellable retention element 2994, 3094, 3194, 3294 includes a portion configured to expand laterally, relative to the proximal axis 2912, 3012, 3112, 3212, in a direction away from a lacrimal canaliculus ampulla 252 (FIG. 2) when the implant body is implanted. In some examples, as shown in FIGS. 29-30, the fluid swellable retention element 2994, 3094, 3194, 3294 includes a portion configured to expand laterally, relative to the proximal axis 2912, 3012, 3112, 3212, in a direction toward the lacrimal canaliculus ampulla 252 (FIG. 2) when the implant body is implanted.

In some examples, the fluid swellable retention element 2994, 3094, 3194, 3294 can comprise hydrogel, which is insertable through the lacrimal punctum 212, 214 and into the associated canaliculus 208, 210 in a narrow profile. After insertion, the hydrogel or other fluid swellable retention element can hydrate and expand to a wide configuration. Protrusions, such as at least one intermediately-disposed retainment projection 2992, 3092, 3192, 3292, can be used to retain to an implanted position of the lacrimal implants while the hydrogel or other swellable element expands.

Figure 33:
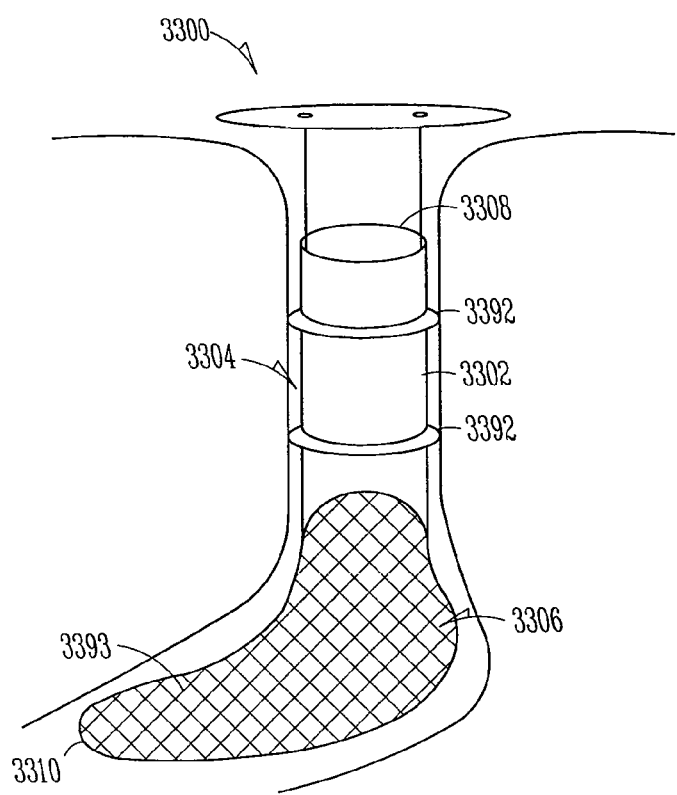
FIG. 33 illustrates a side view of an example lacrimal implant configured to be retained within a lacrimal punctum and associated canalicular anatomy, the lacrimal implant including an expandable retention element.

FIG. 33 illustrates an example side view of another lacrimal implant 3300 that is insertable through a lacrimal punctum 212, 214 and into the associated canaliculus 208, 210 (FIG. 2). In this example, the lacrimal implant 3300 can comprise an implant body 3302 including first 3304 and second 3306 portions, and can extend from a proximal end 3308 of the first portion 3304 to a distal end 3310 of the second portion 3306. As shown, the second portion 3306 can include an expandable retention element 3393 comprising at least one of a coil, a braid, a stent, a mesh tube, a suture, a thermoset polymer, a thermoplastic, a heat activatable material, or a shape memory material. The expandable retention element 3393 can be configured to expand laterally, relative to a proximal axis 3312 defined by the first portion 3304, when the implant body is implanted. Protrusions, such as at least one intermediately-disposed retainment projection 3392, can be used to potentially further secure an implanted position of the lacrimal implant.

FIGS. 34A-34B illustrate examples of a schematic view of another lacrimal implant 3400 and an implant environment. In various examples, the implant body 3402 can include a graspable or other projection 3432, such as one or more projections extending laterally at least partially from or around a proximal end 3408 of a first implant body portion. In some examples, such as is shown in FIG. 34B, the projections 3432 can include a set of wings for use in inserting the lacrimal implant 3400 into, or removing the implant from, an implanted position. The set of wings can be configured without migration in mind, as the implanted, non-linear configuration of the implant body 3402 can prevent migration by assuming a size or shape of a canaliculus curvature 250 and optionally, a lacrimal canaliculus ampulla 252.

In the examples of FIGS. 34A-34B, the one or more projections 3432 extend laterally in a direction parallel to or away from an eye 100 when implanted. In this way, the projections 3432 can still act as a graspable or feedback feature, but can limit patient discomfort when the lacrimal implant 3400 is implanted. In addition, the projections 3432, by extending away from the eye 100, may not be buried in tissue and may be easily recognized by the patient or physician. This can allow for a quick determination if the lacrimal implant 3400 is being retained in its proper place without having to dig and search in the soft tissue surrounding the eye 100. In some instances, a simple pull on the lower eyelid can expose the projection 3432 pointed in a direction away from the eye 100. In the example of FIG. 34B, a lateral extension of at least one projection 3432 from the proximal end 3408 is substantially the same as a lateral extension direction of a second implant body portion relative to a distal end of the first implant body portion.

FIGS. 35-38 illustrate examples of an isometric view of various graspable projections or other gripping means 3532, 3632, 3732, 3832 extending from a proximal end of a lacrimal implant 3500, 3600, 3700, 3800. The graspable or other projections 3532, 3632, 3732, 3832 can be used for various functions, including providing a structure to which a user can grasp onto during implant insertion or removal, inhibiting or preventing the associated lacrimal implant from passing completely within a lacrimal punctum 212, 2114 and associated canaliculus 208, 210 (FIG. 2), or for providing tactile or visual feedback information to the user, e.g., as to whether the implant is fully implanted.

Figure 35:
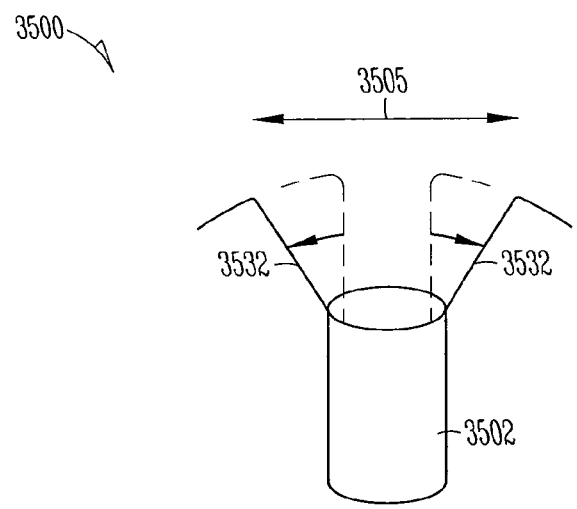
FIGS. 35-38 illustrate isomeric views of various lacrimal implant proximal end portions, each proximal end portion including a graspable projection or void.

In some examples, as shown in FIG. 35, the graspable projection 3532 can include two or more expandable arm members, which are sized to rest on an exterior of the lacrimal punctum. The arm members can be affixed to an implant body 3502, for example, via molding, adhesion or welding. The expandable arm members are capable of expanding so as to limit penetration of the lacrimal implant 3500 through the lacrimal punctum 212, 214 and into the associated canaliculus 208, 210. While two arm members are shown, some include more than two arm members, such as four arm members. The expandable arm members can assume an expanded profile separation distance 3505 that corresponds to about twice a diameter of the implant body, such that proximal ends of the proximal expandable arm members remain on the exterior of the punctum. The expandable arm members can expand in many ways from the narrow profile configuration to the expanded profile configuration, and can include at least one of a coil, a braid, a suture, a thermoset polymer, a thermoplastic, a heat activated material, Nitinol, a shape memory material, a polymer, polypropylene, polyester, nylon, natural fibers, stainless steel, polymethylmethacrylate or polyimide. In some examples, the expandable arm members can be expanded manually, for example by a physician, after the lacrimal implant has been positioned in the canalicular lumen 208, 210.

Figure 36:
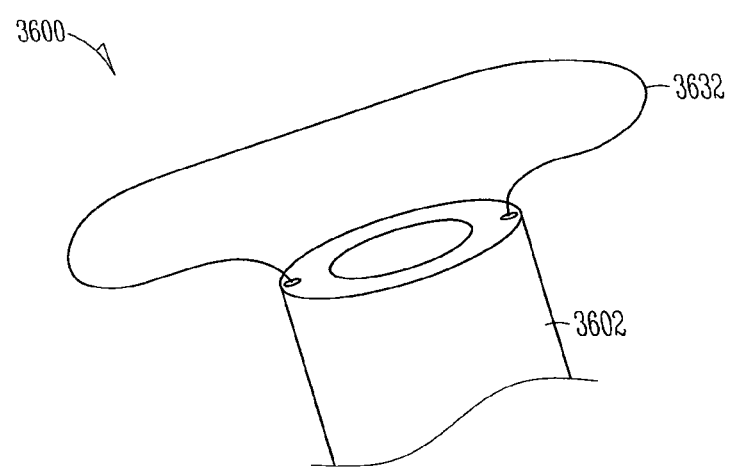

In some examples, as shown in FIG. 36, the graspable projection 3632 can include a loop of a filament embedded in the proximal end of the lacrimal implant 3600 to permit removal of the implant with proximal tension to the loop, for example with forceps. In some examples, the loop of filament assumes a shape similar to a purse handle that extends from the lacrimal implant with a loop so as to facilitate removal of the lacrimal implant. The filament can comprise at least one of a heat activated material, Nitinol, a shape memory material, a polymer, polypropylene, polyester, nylon, natural fibers, stainless steel, polymethylmethacrylate or polyimide. In some embodiments, the filament may comprise an absorbable thermo plastic polymer, for example at least one of polylactic acid (PLA), poly glycolic acid (PGA) or polylactic co-glycolic acid (PLGA). A distal end of the filament can be embedded in, molded to or other affixed to an implant body 3602 so as to secure the filament to the lacrimal implant.

Figure 37:
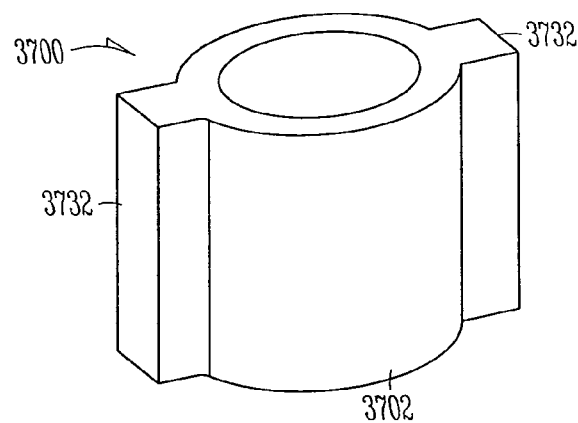

In some examples, as shown in FIG. 37, the graspable projection 3732 can include at least one axially extending projection coupled with an implant body 3702, which is configured to bias an outer most portion of the lacrimal canaliculus 208, 210. Due to the natural constriction against outward biasing of the canaliculus, the interplay between the axially extending projections and the canaliculus inhibits over insertion of an associated lacrimal implant 3700.

Figure 38:
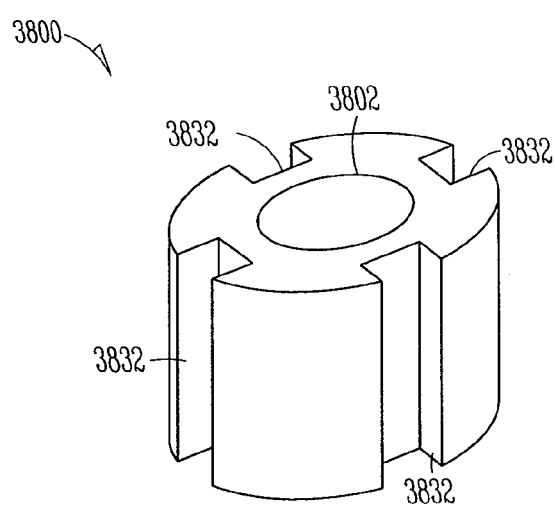

In some examples, as shown in FIG. 38, a longitudinal indentation, channel or other recess 3832 in an implant body 3802 can be used in lieu of a graspable projection to permit insertion or removal of a lacrimal implant 3800. The indentation, channel or other recess 3832 may extend axially along only a portion of an implant body a sufficient distance to facilitate removal of an associated lacrimal implant. In further examples, a lacrimal implant can include a filament molded into an implant body and extending proximally for removal of the implant from the punctum.

Figure 39A:
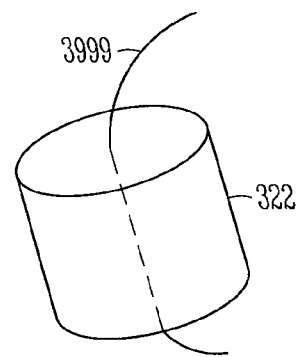
FIGS. 39A-39B illustrate an isomeric view of example drug inserts and a removal-facilitating filament.
Figure 39B:
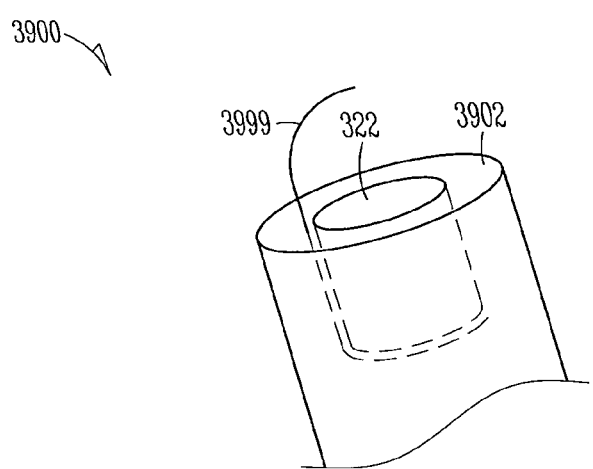

FIGS. 39A-39B illustrate examples of an isometric view of a drug insert 322 and a removal facilitating filament 3999. In some examples, as shown in FIG. 39A, the filament 3999 can extend from the drug insert 322 and is molded therein for removal purposes. Among other things, the filament 3999 can comprise a suture, a thermoset polymer, or a shape memory alloy. In some examples, as shown in FIG. 39B, the filament 3999 extends along the drug insert 322 adjacent an implant body 3902 and is bonded to a distal end of the insert for removal purposes. Filament can be bonded to the distal end of the drug core insert with an adhesive, such as cyanoacrylate, acrylic, epoxy, urethane or a hot melt adhesive.

Figure 40:
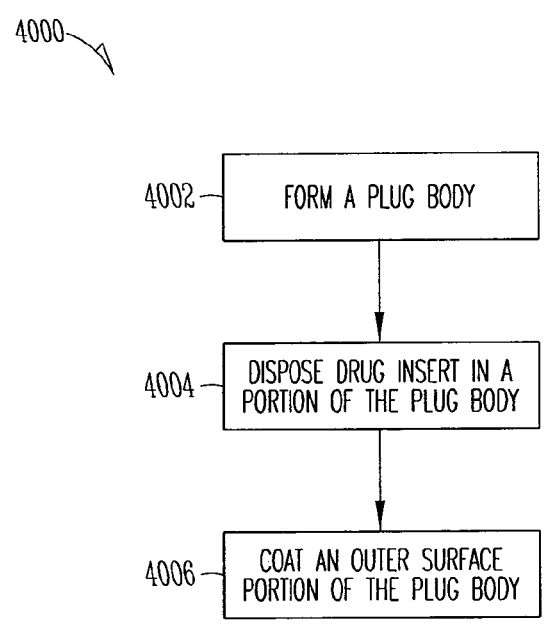
FIG. 40 illustrates an example method of manufacturing a lacrimal implant configured to be retained within a lacrimal punctum and associated canalicular anatomy.

FIG. 40 is a block diagram illustrating an example method 4000 of manufacturing a lacrimal implant configured to be at least partially insertable through a lacrimal punctum and into the associated canaliculus. At 4002, an implant body extending from a proximal end of a first body portion to a distal end of a second body portion is formed. In various examples, the proximal end is formed to define a longitudinal proximal axis and the distal end is formed to define a longitudinal distal axis. A formation of the implant body can be configured such that, when implanted, the proximal axis and the distal axis intersect at an angle of at least 45 degrees to laterally bias at least a portion of the implant body against at least a portion of a lacrimal canaliculus located at or more distal to a canaliculus curvature. Optionally, formation of the implant body can include integrating one or more drug or other therapeutic agent particles into the body. The implant body can then be optionally coated with a permeable or impermeable material to direct agent release, as desired, to a patient's bodily tissue(s).

In some examples, various sizes of implant bodies are formed to fit various patient anatomies. To determine a patient's punctal size, one or two drops of a topical ophthalmic anesthetic can be applied to an eye when the patient is in a reclined position with his/her eyelids closed for a brief period of time (e.g., approximately 60 seconds). Subsequently, a punctal gauge can be used to measure a diameter of one or both of the upper or lower puncta. The punctal gauge can be urged into a punctum until a slight resistance is felt on the gauge, at which time a measurement corresponding to a gradation on the gauge can be read and recorded.

In some examples, the second body portion is formed to include a dilator generally narrowing from a location near a proximal end of the second body portion to the distal end of the second body portion. In some examples, the dilator is formed by sloping an outer surface of the second portion of the implant body between about 1 degree and about 10 degrees with respect to the longitudinal distal axis. In some examples, the outer surface of the second implant body portion is sloped to a dilator tip of between about 0.2 millimeters and about 0.5 millimeters.

In some examples, the implant body is formed to include a graspable or other projection extending laterally from the proximal end of the first body portion. In certain examples, the projection is formed to substantially align with a lateral extension direction of the second body portion relative to the first body portion. In certain examples, the projection is formed such that, when implanted, it laterally extends from the proximal end of the first body portion in a direction that is parallel to or away from an eye.

At 4004, a drug insert can be disposed in at least one of the first body portion or the second body portion. In various examples, the drug insert is positioned such that an exposed drug insert surface sits adjacent at least one of the proximal end or the distal end for providing a sustained drug or other therapeutic agent release to an eye, nasal passage or inner ear, for example. In certain examples, a first drug insert is disposed in the first body portion and a second drug insert is disposed in the second body portion. In various examples, the one or more drug inserts comprise drug cores including the drug or other therapeutic agent.

At 4006, an outer surface portion of the implant body or implant body coating can be coated with at least one of a fluid swellable material, a lubricious coating or an antimicrobial coating. In various examples, the outer surface portion of the implant body is polished using a polishing process.

OTHER EXAMPLES

Figure 41:
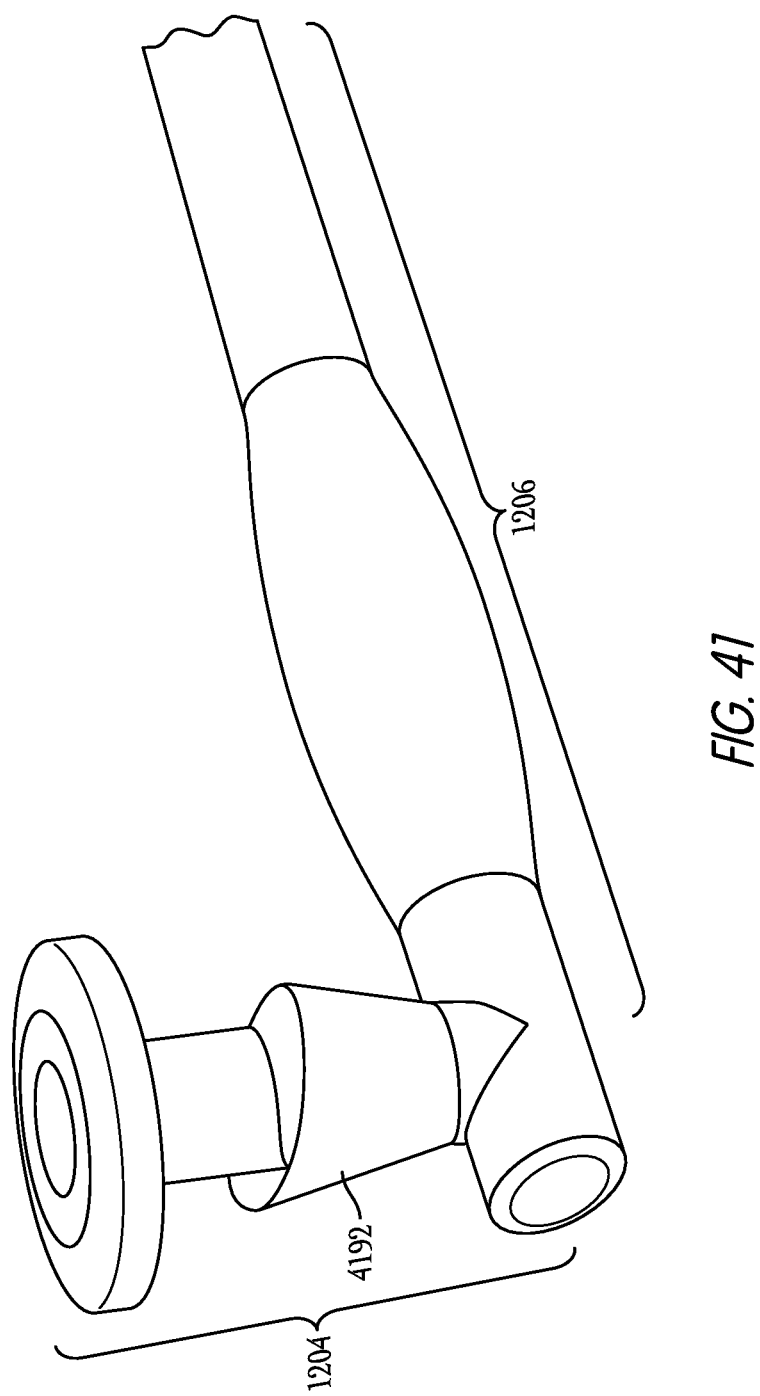
FIG. 41 illustrates a side view of an example lacrimal implant configured to be retained within a lacrimal punctum and associated canalicular anatomy, the lacrimal implant including at least one intermediately-disposed retainment projection.

FIG. 41 shows an example in which a lacrimal implant, such as the example of FIG. 12, can be modified such that the retention mechanism 1292 of the first portion 1204 need not laterally protrude equidistantly around its circumference. Instead, in an example such as shown in FIG. 41, a proximal end of a retention mechanism 4192 of the first portion 1204 can laterally protrude outward in an on-equal lateral distance around its circumference, and the retention mechanism 4192 of the first portion 1204 can taper down to an outer diameter of the first portion 1204 at a distal end of the retention mechanism 4192. In an example, the proximal end of the retention mechanism 4192 can include a perimeter numerically equal to a perimeter of a cap 1208 or other projection at a proximal end of the first portion 1204.

In an example, the proximal end of the retention mechanism 4192 of the first portion 1204 can protrude outward contralaterally, such as in opposite directions on opposing first and second sides of the retention mechanism 4192 of the first portion 1204, without protruding outwardly from the shaft portion outer dimension on opposing third and fourth sides of the retention mechanism (wherein the third and fourth sides define a second lateral direction that is substantially orthogonal to a first lateral direction defined by the first and second sides). In this way, the contralaterally protruding portions of the retention mechanism 4192 of the first portion 1204 can define an end-to-end lateral distance in the first lateral direction that can be substantially equal to the protruding outer diameter of the proximal end of the retention mechanism 1292 of the first portion 1204, such as shown and described with respect to FIG. 12.

Various other options for the implant are also possible. Smoothed corners can optionally be provided, such as to reduce tissue irritation or damage. Sharp corners can optionally be provided, such as to enhance retention. In a perpendicular second lateral direction, however, there can be no protrusion beyond the outer shaft diameter of the retention mechanism 4192 of the first portion 1204. In an example, the first lateral direction of the contralaterally protruding portions of the retention mechanism 4192 of the first portion 1204 is also substantially orthogonal to the direction in which the second portion 1206 extends from the first portion 1204, which can provide better retention. However, in another example, the first lateral direction of the contralaterally protruding portions of the retention mechanism 4192 of the first portion 1204 can be substantially parallel to the direction in which the second portion 1206 extends from the first portion 1204. In still other examples, the first lateral direction of the contralaterally protruding portions of the retention mechanism 4192 of the first portion 1204 can be at other angles (e.g., between 0 degrees and 90 degrees) with respect to the direction in which the second portion 1206 extends from the first portion 1204.

Figure 42A:
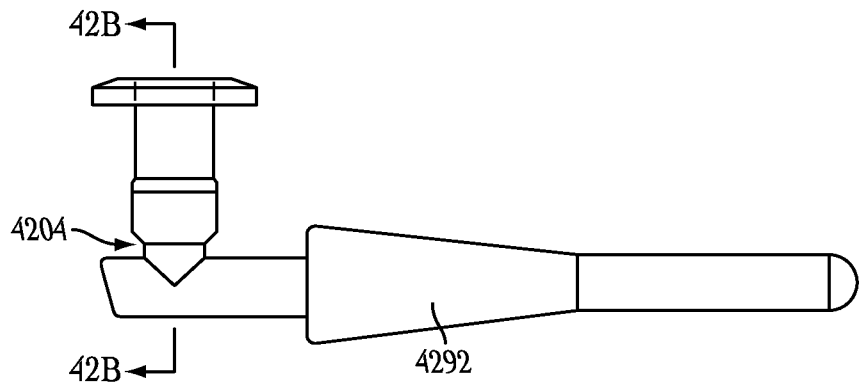
FIGS. 42A-42D illustrate an example lacrimal implant configured to be retained within a lacrimal punctum and associated canalicular anatomy, the lacrimal implant including at least one intermediately-disposed retainment projection, such as with a retention mechanism on a distal second segment that can include an abrupt step.
Figure 42B:
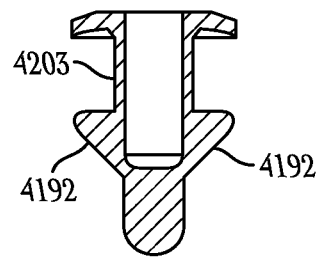
Figure 42C:
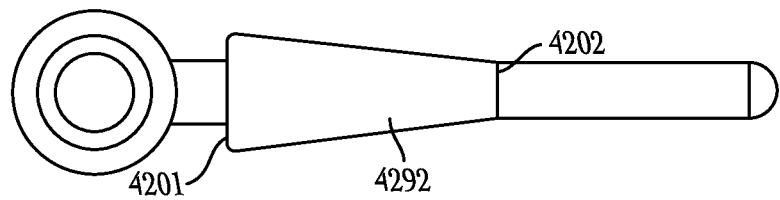
Figure 42D:
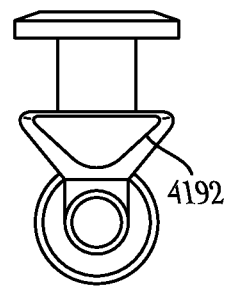

FIGS. 42A-42D show an example in which a lacrimal implant, such as those shown in the examples of FIGS. 12 and 41, can be modified such that the retention mechanism 1292 of the second portion 1206, need not gradually bulge outward from the lateral outer dimensional profile of the second portion 1206. More specifically, FIG. 42A shows a side view of the example lacrimal implant, FIG. 42B shows a cross-sectional view taken along the cutline A-A shown in FIG. 42A, FIG. 42C shows a top view of the lacrimal implant, and FIG. 42D shows an end view of the lacrimal implant such as when viewed from a proximal end of the second portion 1206.

In the examples of 42A-42D, the second portion 1206 can include a retention mechanism 4292 that has a more abrupt change profile, such as an outward lateral step, at one of the proximal end portion 4201 of the retention mechanism 4292 or the distal end portion 4202 of the retention mechanism 4292. For example, the retention mechanism 4292 can include at its proximal end portion 4201 an abrupt step, such as from an outer diameter of the second portion 1206 (e.g., about 0.46 mm to about 0.62 mm) to an at least partially circumferentially protruding outer diameter of the proximal end portion 4201 of the retention mechanism 4292 (e.g., about, 0.76 mm, about 0.86 mm or about 0.89 mm). Smoothed corners can optionally be provided, such as to reduce tissue irritation or damage. Sharp corners can optionally be provided, such as to enhance retention. In this example, the outer diameter of the retention mechanism 4292 can then taper back down toward the outer diameter of the second portion 1206 (e.g., about 0.46 mm to about 0.62 mm), as the distal end portion 4202 of the retention mechanism 4292 is approached.

The example of FIGS. 42A-42D can include the tapered retention mechanism 4192 of the first portion 1204 extending laterally outward in a direction perpendicular from the direction in which the second portion 1206 extends outward from the first portion 1204, without extending laterally outward in a direction parallel to the direction in which the second portion 1206 extends outward from the first portion 1204, and providing a shaft portion defining a narrowed, at least partially circumferential, neck 4203 portion between the proximal cap 1208 of the first portion 1204 and the retention mechanism 4192 of the first portion 1204, such as explained above with respect to FIG. 41. A narrowed, at least partially circumferential, neck portion 4204 can also be provided at the juncture between the first portion 1204 and the second portion 1206 for retainment purposes. It is believed that canalicular tissue can compress into and around the neck portion 4204, thereby helping to secure an implanted position of the lacrimal implant.

FIGS. 43A-43C show an example in which a lacrimal implant, such as those shown in the examples of FIGS. 12, 41 and 42A-42D, can be modified such that the retention mechanism 1292, 4192 of the first portion 1204 need not include a neck portion at the juncture between the first portion 1204 and the second portion 1206. More specifically, FIG. 43A shows a side view of the example lacrimal implant, FIG. 43B shows a bottom view of the lacrimal implant, and FIG. 43C shows a cross-sectional view of the lacrimal implant taken along the cutline A-A shown in FIG. 43B.

In the example of FIGS. 43A-43C, the proximal end 1208 can provide a projection such as a cap having an outer diameter of about 1.1 mm, and a cap thickness of about 0.13 mm in a longitudinal direction of the first portion 1204. In this example, the proximal end 1208 cap portion can be separated from a retainment projection 4392 of the first portion 1204, such as by a shaft portion that can have an outer diameter of about 0.56 mm and a longitudinal shaft length of about 0.66 mm. In this example, the retainment projection 4392 of the first portion 1204 can have a proximal outer diameter of about 1.1 mm, which can taper down over about 0.96 mm directly into the second portion 1206, such that there is no neck portion provided at the juncture 4305 between the first 1204 and second 1206 portions. By eliminating the neck portion, such as is shown in FIGS. 42A-42D, the length of the retainment projection 4392 can be made effectively longer allowing for wider proximal outer diameters, such as diameters greater than about 1.1 mm, and/or increased dilation and easier insertability via a more gradual taper angle. In some examples, the proximal outer perimeter can optionally include sharp corners, such as to enhance retention.

Other dimensional options for the example insert of FIGS. 43A-43C can be as follows. The proximal end 1208 can provide a projection such as a cap having an outer diameter of about 1.4 mm. The retainment projection 4392 of the first portion 1204 can have a proximal outer diameter of about 1.3 mm. The neck portion between the proximal cap 1208 and the retainment projection 4392 can have a diameter of about 0.7 mm and a first cavity within the first portion 1304 can have a diameter of about 0.56 mm. A thickness of the retainment projection 4392 at the juncture 4305 between the first 1204 and second 1206 portions, as measured perpendicular to an outer converging surface of the projection 4392, can be 0.043 mm, 0.086 mm, or 0.175 mm, for example, depending on the depth of the first cavity and the configuration and position of the projection 4392 relative to the first portion 1204.

In certain examples, the retention mechanisms 1292, 4192, 4392 of the first portion 1204 or the retention mechanisms 1292, 4292 of the second portion 1206 can optionally be implanted as a self-expanding hydrogel coating upon a plug body, wherein the self-expanding coating expands to form a shape that is generally similar to those such as shown in FIGS. 41, 42A-42D, and 43A-43C.

Figure 44A:
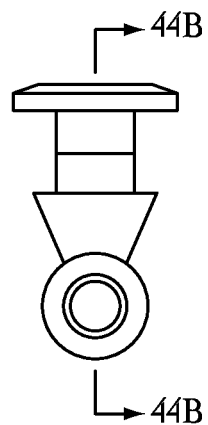
FIGS. 44A-44C illustrate an example lacrimal implant configured to be retained within a lacrimal punctum and associated canalicular anatomy, the lacrimal implant including a recess extending from a proximal end of a distal segment.
Figure 44B:
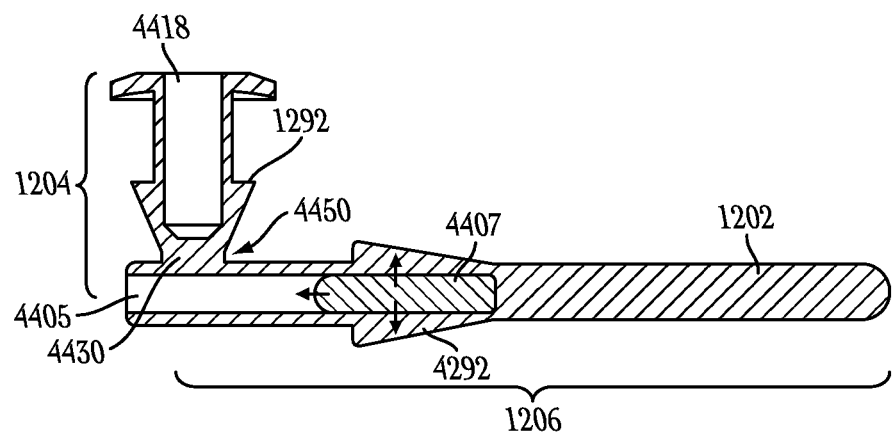
Figure 44C:
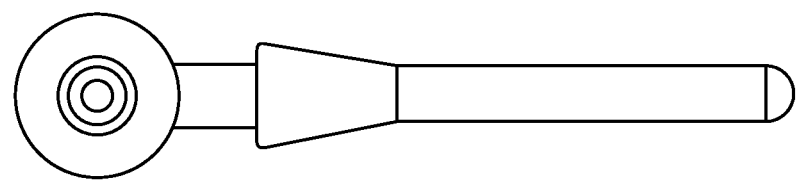
Figure 45A:
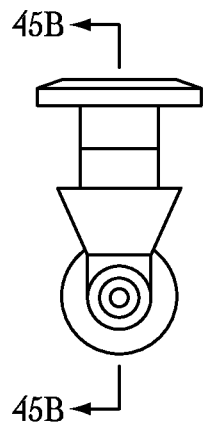
FIGS. 45A-45C illustrate an example lacrimal implant configured to be retained within a lacrimal punctum and associated canalicular anatomy, the lacrimal implant including a recess extending from a proximal end of a distal segment and including an expandable material therein.
Figure 45B:
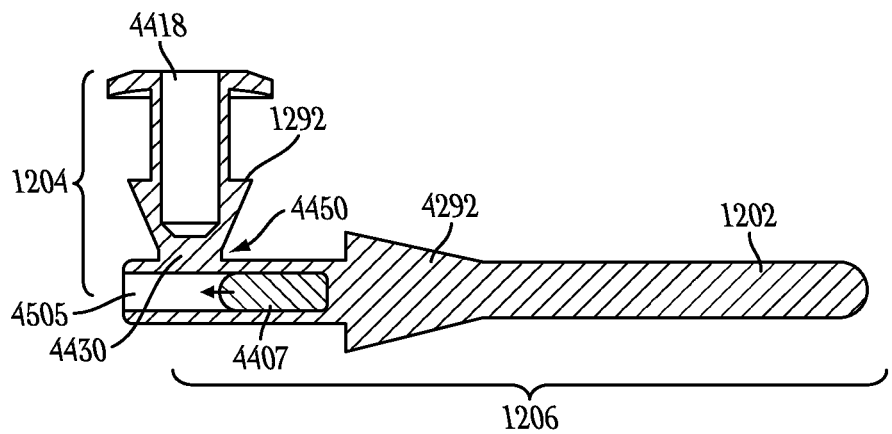
Figure 45C:
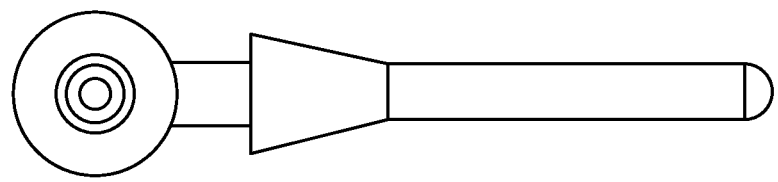

FIGS. 44A-44C and 45A-45C show examples in which a lacrimal implant, such as those shown in the examples of FIGS. 12, 41, 42A-42D, and 43A-43C, can be modified such that a relatively deep recess 4405 or relatively shallow recess 4505 can extend from a proximal end of the second portion 1206, such as extending into the second portion 1206. FIGS. 44A and 45A show examples of an end view of the lacrimal implant such as when respectively viewed from a distal end and the proximal end of a second portion 1206, FIGS. 44B and 45B show examples of a cross-sectional view of the lacrimal implant taken along the cutlines A-A shown in FIGS. 44A and 45A, respectively, and FIGS. 44C and 45C show examples of a top view of the lacrimal implant.

In an example, the recess 4405, 4505 can be used to assist during implant such as by allowing insertion of an instrument into the recess 4405, 4505. In an example, the recess 4405, 4505 can include an expandable material 4407, such as a hydrogel (e.g., "TG-500" or "TG-2000" manufactured by Lubrizol Corporation of Cleveland, Ohio), therein, which can expand when implanted and exposed to bodily fluid. In an example, the recess 4405, 4505 can serve both purposes, allowing insertion of an instrument during implant, and also allowing expansion of a hydrogel, when implanted, such as to assist retention. A depth of the recess 4405, 4505 relative to the proximal end of the second portion 1206 can be adequate to allow for at least some expansion of the expandable material 4407, if present. In some examples, the depth of the recess is twice a longitudinal length of the expandable material 4407. In some examples, the depth of the recess is slightly greater than the longitudinal length of the expandable material 4407.

The expandable material 4407 can be configured and positioned within the recess 4405, 4505 such as to expand in various directions (e.g., laterally and/or circumferentially in a balloon-like manner), when implanted, such as to urge one or more portions of an implant body 1202 outward and against a wall of a lacrimal canaliculus. Through an engagement between the outwardly-urged portions of the implant body 1202 and the canalicular wall, the lacrimal implant can be more securely retained within the punctum. Optionally, the location of the expandable material 4407 within the recess 4405, 4505 of the second portion 1206 can be adjusted, as needed, such as to achieve desired retainment characteristics. In some examples, the expandable material 4407 is positioned within the recess 4405, 4505 such that upon expansion, a portion of the expandable material 4407 protrudes externally relative to the recess 4405, 4505. In other examples, the expandable material 4407 is positioned within the recess 4405, 4505 such that upon expansion, the expandable material 4407 is substantially retained within the recess, and does not substantially protrude externally relative to the recess 4405, 4505.

In various examples, the implant body 1202 can comprise an elastic material, such as silicone, polyurethane or other urethane-based material, or an acrylic of a non-biodegradable, partially biodegradable or biodegradable nature (i.e., erodeable within the body), such as for allowing at least partial outward deformation of the implant body 1202 as the expandable material 4407 absorbs or otherwise retains fluid. In some examples, different portions of the implant body 1202 can be made of different materials. For instance, the first portion 1204 can comprise a more rigid, less expandable material and the second portion 1206 can comprise a more elastic material. The second portion 1206 can also comprise a fluid permeable material such as to promote or allow for fluid to better infiltrate the expandable material 4407. Optionally, a wall thickness of the second portion 1206 surrounding the expandable member 4407 can be made thinner such as to facilitate outward deformation as the expandable member 4407 absorbs or otherwise retains fluid.

As shown in the examples of FIGS. 44B and 45B, the expandable material 4407 can have a non-expanded, "dry" state, which can aid insertion through the punctum and into the lacrimal canaliculus. Once placed in the canaliculus, the expandable material 4407 can absorb or otherwise retain canalicular or other bodily fluid, such as via an orifice of the recess 4405, 4505 or via a fluid permeable material of, or lumen in, the second portion 1206 surrounding the material 4407. In some examples, the expandable material 4407 can include a material that is non-biodegradable. In some examples, the expandable material 4407 can include a material that is biodegradable. Other options for the expandable material 4407 can also be used. For instance, the expandable material 4407 can be molded with the implant body 1202 as a single piece, or can be formed separately and subsequently coupled to, or otherwise disposed in, the implant body 1202.

Desired expansion characteristics of the expandable material 4407 can be achieved such as through appropriate material configuring and processing. In some examples, the expandable material such as a hydrogel, is extruded with a high draw-down ratio such as to result in a dimension (e.g., diameter of about 0.3 millimeter) configured to fit within the recess 4405, 4505. It has been found that extrusions formed with a high draw-down ratio can have greater diametrical expansion than longitudinal expansion. In some examples, the expandable material 4407 is molded at a temperature and pressure found to result in a desirable expansion characteristics, such as greater longitudinal expansion than diametrical expansion. For instance, in some examples, the expandable material 4407 is configured and positioned to laterally expand out of the recess 4405, 4505, when implanted, such as into the ampulla to assist retention of the lacrimal implant within the punctum. The lateral expansion of the expandable material 4407 has been found to be able to continuously urge a cap 1208 or other projection at a proximal end of the first portion 1204 flush with the punctum. In an example, the expandable material 4407 can allow for an expansion capacity of up to about one time its "dry" volume, up to about ten times its "dry" volume, or up to about twenty times its "dry" volume.

It has been found that expansion of the expandable material 4407 within the recess 4405, 4505, when implanted, can help lock the angled intersection 4450 between the implant body first portion 1204 and the implant body second portion 1206 such as to assist retention of the lacrimal implant within the punctum. It is believed that as the expandable material 4407 expands in various directions within the recess 4405, 4505, portions of the implant body 1202 are urged outward becoming less elastic as these body portions become larger.

As shown in FIGS. 44B and 45B, the lacrimal implant can include a septum 4430 such as between a first cavity or recess 4418 configured to receive a drug-releasing or other agent-releasing insert (e.g., drug core) and the second recess 4405, 4505. The septum 4430 can be used to inhibit or prevent expansion of the expandable material 4407 into the drug insert-receiving recess 4418. However, in an example, the septum 4430 may include a lumen or porous portion allowing drug or other therapeutic agent(s) to travel from the insert and into and through the expandable material 4407 to surrounding canalicular tissue, thereby providing systemic drug or other agent release.

FIGS. 48A-48E show an example lacrimal implant 4800 including a robust retention element 4856 disposable within a lacrimal canaliculus ampulla, when implanted, an ovoid-shaped graspable or other projection 4832, and a lack of intermediate projections on first 4804 or second 4806 implant body portions. More specifically, FIG. 48A shows an isometric view of the example lacrimal implant, FIG. 48B shows a side view of the lacrimal implant, FIG. 48C shows a cross-sectional view taken along the cutline A-A shown in FIG. 48B, FIG. 48D shows a top view of the lacrimal implant, and FIG. 48E shows an end view of the lacrimal implant, such as when viewed from a proximal end of the second portion 4806.

In the example of FIGS. 48A-48D, the implant body 4802 includes the ovoid-shaped graspable or other projection 4832, which can be configured to seat against or near a punctal opening 212, 214 (FIG. 2) when the implant 4800 is fully inserted within a lacrimal canaliculus 208, 210. The projection 4832 can inhibit or prevent the implant 4800 from passing completely within the lacrimal canaliculus or provide tactile or visual feedback information to an implanting caregiver physician. In some examples, the ovoid shape can include a width of about 1.36 millimeters, a length of about 1.92 millimeters, and a thickness of about 0.30 millimeters.

A proximal end 4828 of the second implant body portion 4806 can include the robust retention element 4856, which is configured to bias against at least a portion of a lacrimal canaliculus ampulla 252 when the lacrimal implant is implanted. The retention element 4856 projects proximally from the intersection between the first 4804 and second 4806 implant body portions, in an opposite direction as the extension of a longitudinal dilator 4850 of the second body portion. In some examples, the retention element 4856 can project proximally about 0.44 millimeters and have a height or thickness of about 0.53 millimeters. In this example, the retention element 4856 includes a boat hull-like shape and can include an insertion-facilitating depression 4875 graspable by an insertion tool. When implanted in the ampulla 252, the retention element 4856 can help secure a seated position of the graspable or other projection 4832 against the punctal opening 212, 214.

In various examples, the second portion 4806 can include a length having a magnitude less than four times a length of the first portion 4804. In one example, the second portion 4806 can include a length less than about 10 millimeters and have a configuration including the longitudinal dilator 4850 and a constant diameter portion 4890. In some example, the implant body 4802 includes a first cavity 4818 disposed near a proximal end 4808. In this example, the first cavity 4818 extends inward about 1.22 millimeters from the proximal end 4808, and houses a first drug-releasing or other agent-releasing drug insert having an outer diameter of about 0.56 millimeters.

FIGS. 49A-49F show an example in which a lacrimal implant 4900, such as the implant example of FIG. 12, can be modified such that the graspable or other projection 4932 includes a retaining lip 4990. The retaining lip 4990 can be configured to secure a seated position of a drug-releasing or other agent-releasing drug insert placed in an implant body cavity 4918. More specifically, FIG. 49A shows an isometric view of the example lacrimal implant, FIG. 49B shows a side view of the lacrimal implant, FIG. 49C shows a cross-sectional view taken along the cutline A-A shown in FIG. 49B, FIG. 49D shows a top view of the lacrimal implant, FIG. 49E shows an end view of the lacrimal implant such as when viewed from a proximal end of the second portion 4906, and FIG. 49F shown an enlarged view of section B-B shown in FIG. 49C.

In various examples, the retaining lip 4990 can be configured to secure a position of a drug insert placed in the implant body cavity 4918 without appreciably effecting the release rate of drug or other agent stored in the insert. In some examples, the retaining lip 4990 extends inward about 0.05 millimeters (±0.02 millimeters) from a surface of the cavity 4918. In some examples, the retaining lip 4990 includes a thickness of about 0.05 millimeters (±0.02 millimeters). Other options to secure the drug insert within the implant cavity 4918 can include one or more of a tighter interference fit between an outer surface of the drug insert and an surface of the cavity, or an overlapping (e.g., snap fit-like) design between the drug insert and cavity at an intermediate or distal portion of the insert.

Due to the presence of the retaining lip 4990, an exposed, outward-facing surface of the drug insert fully seated in the implant cavity 4918 may be slightly below a proximal end 4908 of the first portion 4904 or a distal end 4910 of the second portion 4906; however, this sunken arrangement does not, and is in intended to create, any type of pore used to control the rate of drug or other agent release from the insert.

Figure 50A:
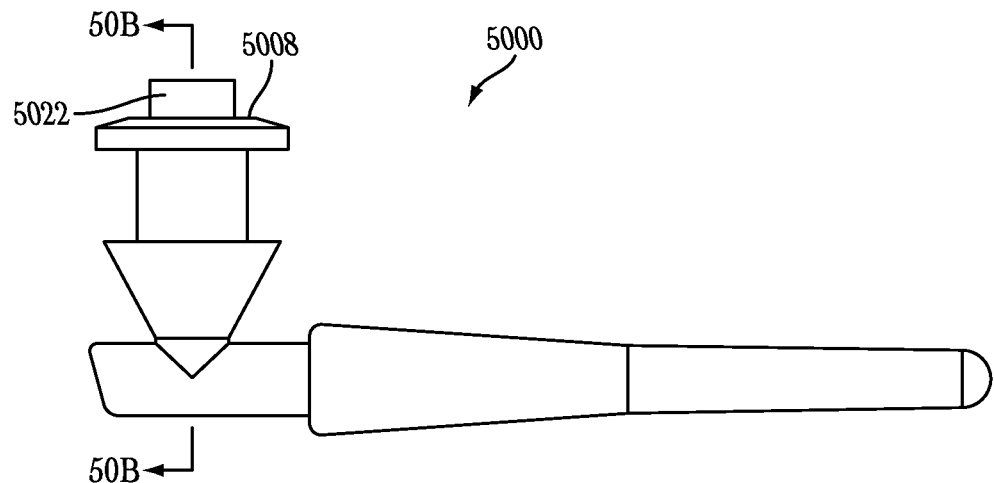
FIGS. 50A-50B illustrate an example lacrimal implant configured to be retained within a lacrimal punctum and associated canalicular anatomy, the lacrimal implant including a raised drug insert.
Figure 50B:
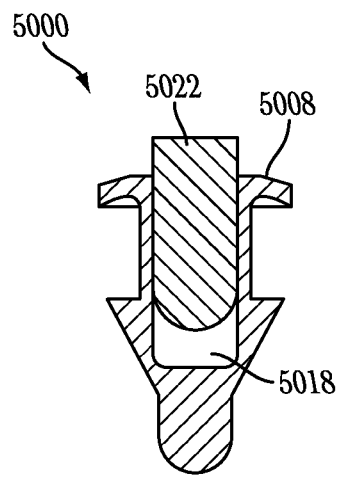

FIGS. 50A and 50B show an example in which a lacrimal implant 5000, such as the example of FIGS. 44A-44C (with the exception of the recess and expandable material), can be modified such that a proximal surface of a drug insert 5022 is positioned above a proximal end 5008 of the implant prior to being fully implanted within a patient. More specifically, FIG. 50A shows a side view of the example lacrimal implant, and FIG. 50B shows a cross-sectional view taken along the cutline A-A shown in FIG. 50A.

In some examples, the proximal surface of the drug insert 5022 can be positioned about 0.25 millimeters (±0.05 millimeters) above the proximal end 5008 of the implant. The distal end surface of the drug insert 5022 can be positioned a similar amount above the base of an implant body cavity 5018, which is configured to receive the insert. In this way, the exposed portion of the drug insert 5022 can be used to facilitate insertion of the lacrimal implant 5000 through a punctum and into an associated canaliculus. Then, post-implant, the drug insert 5022 can be urged fully, or near fully, within the cavity 5018. As the drug insert 5022 is urged within the cavity 5018, an optionally slightly larger insert diameter, relative to a cavity diameter, can result in biasing of an outer implant body surface against a portion of the lacrimal canaliculus providing further implant securing.

Figure 51:
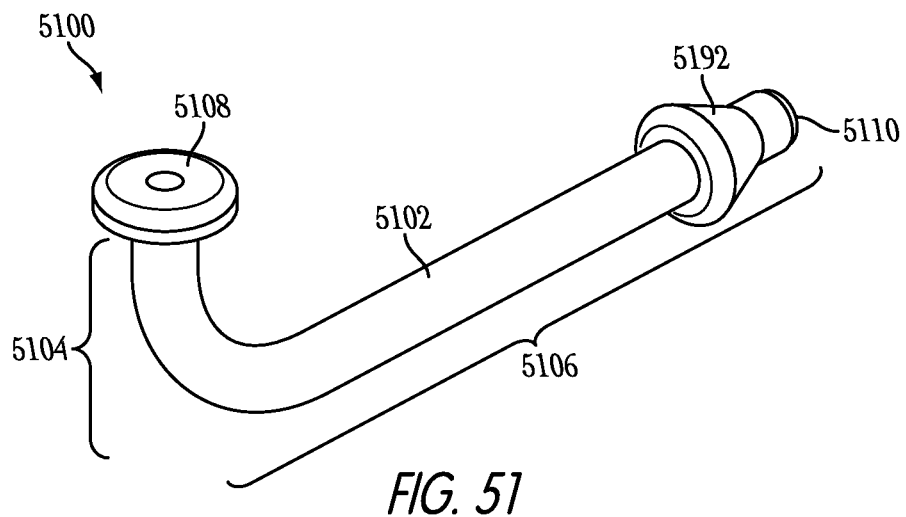
FIGS. 51-52 illustrate an example lacrimal implant configured to be retained within a lacrimal punctum and associated canalicular anatomy, the lacrimal implant including a retention element at or near a distal end.
Figure 52:
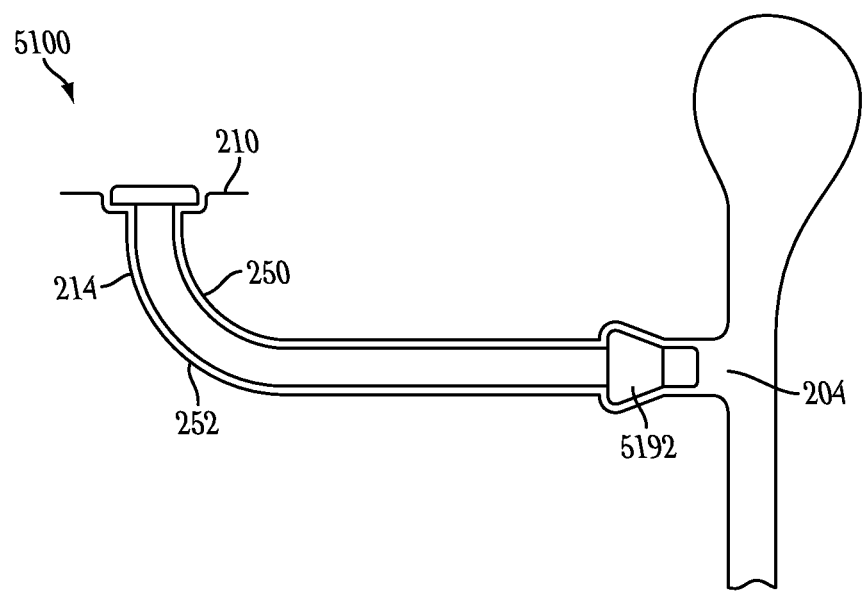

FIGS. 51 and 52, like FIGS. 25A and 25B, illustrate an example of another lacrimal implant 5100 that is insertable through a lacrimal punctum 212, 214 and into the associated canaliculus 208, 210 (FIG. 2). In this example, the lacrimal implant 5100 can comprise an implant body 5102 including first 5104 and second 5106 portions, and can extend from a proximal end 5108 of the first portion 5104 to a distal end 5110 of the second portion 5106. The implant body can include a shape generally matching the anatomical features of a lacrimal canaliculus 208, 210, thereby providing patient comfort and secure retainment. In some examples, a concave shape between the first 5104 and second 5106 portions includes a radius substantially the same as the radius of the canaliculus curvature 250 (FIG. 2).

In certain examples, a retention element 5192 can be disposed at or near the distal end 5110 of the second implant body portion 5106. In this way, the implant 5100 can take advantage of the more rigid lacrimal bone region and the smaller, deeper diameter region of the canaliculus to help secure an implanted position. Further, tear fluid flowing from an eye and around the implant may generate a force against a proximal surface of the distally-located retention element 5192 to aid implant retainment. The retention element 5192 can be passive or active (e.g., using hydrogel or other expandable materials). In some examples, the second implant body portion 5106 includes a length between about 6 to 12 millimeters, such as about 10 millimeters.

FIG. 52 illustrates an example schematic view of the lacrimal implant 5100 implanted in a lower lacrimal punctum 214 and associated canaliculus 210. In some examples, the lacrimal implant 5100 can be implanted in an upper lacrimal punctum 212 and canaliculus 208. As shown, the first portion 5104 can be configured to be inserted through the lacrimal punctum 214 and into the associated canaliculus 210 and rest between the punctal opening and a lacrimal canaliculus ampulla 252, while the second portion 5106 can be configured to insert through the lacrimal punctum 214 and into the canaliculus 210 and rest between the ampulla 252 and the lacrimal sac 204.

Similar dimensions and dimensional variations as shown and described with regard to FIGS. 41, 42A-42D, 43A-43C, 44A-44D, 45A-45D, 48A-48E, 49A-49F, and 50-52 can be applied to the other examples described throughout this patent document.

FIGS. 53A-53D illustrate further lacrimal implant 5300 examples (not shown in their entirety) configured to be retained within a lacrimal punctum and associated canalicular anatomy, which include one or both of a distinct drug insert 5322 or drug integrated with one or more portions of an implant body 5302. Drug or other therapeutic agent stored in the distinct drug insert 5322 or integrated with the implant body 5302 can be delivered on a sustained release basis, at a desired rate, to one or more of an eye, nasal passage or inner ear system. Where greater amounts of drug or other agent are desired, it is possible that the implant body 5302 can be used as a storing mechanism, with or without the drug insert 5322, due to its greater volume.

In some examples, such as is shown in FIGS. 53A, 53B and 53C, a first amount of agent is stored in a drug insert 5322 and a second amount of agent is stored in the implant body 5302. It is believed that such an arrangement may provide for the greatest agent holding capacity, since drug load may negatively impact curing of the implant body material or strength. Accordingly, the amount of drug load in the implant body 5302 may be limited. Optionally, the drug insert 5322 may not include a sheath body 5366 covering one or more portions of the insert 5322, and as a/result, drug or agent diffusion between the implant body 5302 and the insert 5322 is possible.

In some examples, such as is shown in FIG. 53D, the implant body 5302 is substantially solid in the fact that it does not include one or more cavities or other voids for receiving a distinct drug-releasing or other agent-releasing insert. Rather, the implant body 5302 can be configured to receive one or more drugs or other agents integrated throughout one or more body portions. In this way, the entire implant body 5302, or portions thereof, can act as the drug-releasing or other agent-releasing insert, and agent release can be directed using preformed openings in an impermeable or substantially impermeable cover (e.g., parylene cover) surrounding portions of the implant body 5302. In other examples, a permeable cover material can be used to allow for drug or other agent release.

Coating materials 5396 can be applied in varying thicknesses to one or more portions of an outer implant body surface, depending on a desired release rate and direction. In some examples, such as is shown in FIG. 53A, a coating material 5396 is applied to a majority of the implant body surfaces except for surfaces of a graspable or other projection 5332 located at a proximal end 5308. In some examples, such as is shown in FIG. 53B, a coating material 5396 is applied to a majority of implant body surfaces, but does not cover an exposed surface of the drug insert 5322. In some examples, such as is shown in FIGS. 53C and 53D, a coating material 5396 having a first thickness (e.g., about 5-6 µm) is applied to a majority of implant body surfaces, and a coating material 5398 having a second thickness (e.g., about 1 µm) is applied to a proximal surface 5308 of the implant body 5302 and/or drug insert 5322.

Some preferred coating materials are believed to be parylene, ceramic and silver, all of which can exhibit good flexibility. In some examples, a parylene coating material is used and can advantageously be vapor-deposited on an implant body at relatively low temperatures.

EXPERIMENTAL EXAMPLES

In order that the present lacrimal implants of FIGS. 44A-44C and 45A-45C can be more fully understood, the following examples are given by way of illustration but not of limitation.

Experimental Example 1

Figure 46:
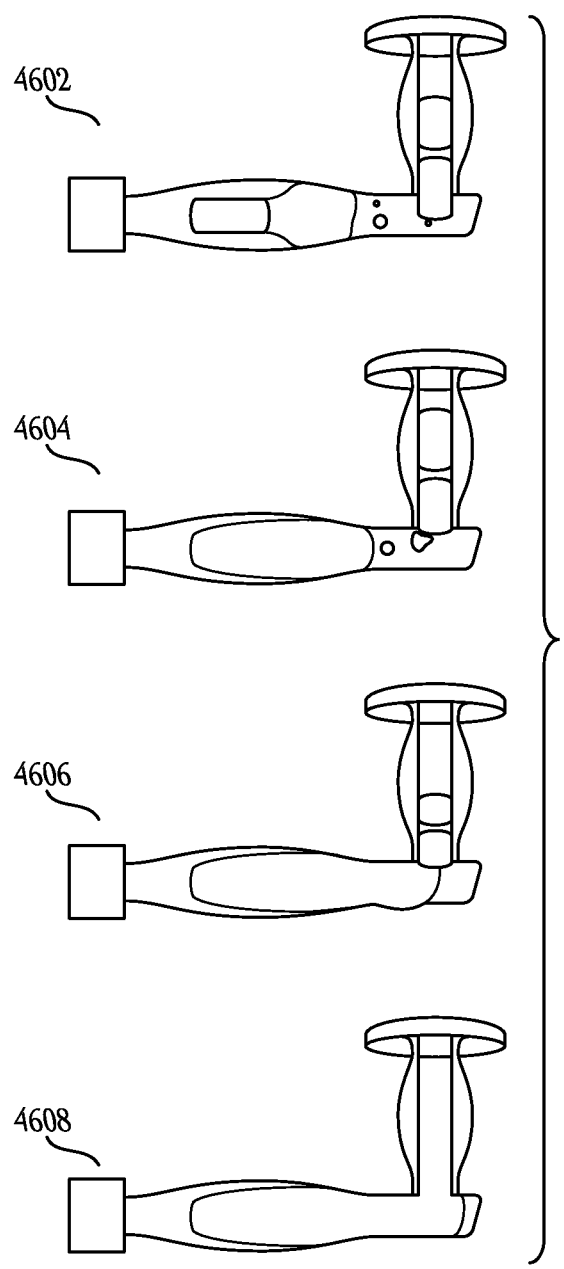
FIGS. 46-47 illustrate example experimental results of a lacrimal implant including a recess extending from a proximal end of a distal segment, the recess including an expandable material therein.

FIG. 46 illustrates a lacrimal implant comprising a recess extending from a proximal end of an implant body second portion. In the recess, an expandable hydrogel material is disposed. To allow fluid to be received by the hydrogel material, an orifice of the recess is left open.

At 4602, the hydrogel material and the partially surrounding implant body is shown at a time of 30 minutes hydration. At 4604, the hydrogel material and the partially surrounding implant body is shown at a time of 120 minutes hydration. At 4606, the hydrogel material and the partially surrounding implant body is shown at a time of 240 minutes hydration. At 4608, the hydrogel material and the partially surrounding implant body is shown at a time of 1440 minutes hydration. As shown, the expansion of the hydrogel material causes surrounding portions of the implant body, particularly the second portion of the implant body, to expand outward such as to a size and shape of a canalicular wall to securely retain a desired position of the implant. Further, the expansion of the hydrogel material locks an angled intersection between the implant body first portion and the implant body second by pressing against the septum, which separates a first cavity or recess holding a drug-releasing or other agent-releasing insert (e.g., drug core) and the second recess holding the hydrogel material.

Experimental Example 2

Figure 47:
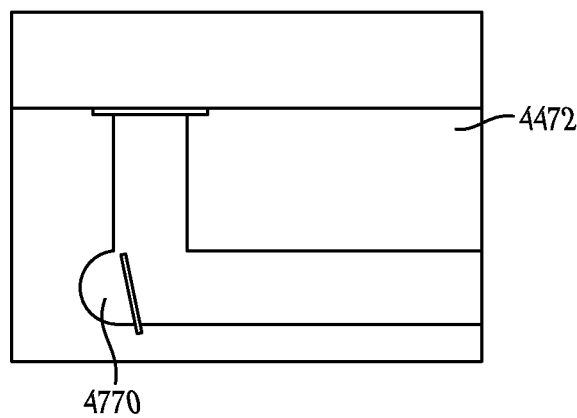

FIG. 47 illustrates a lacrimal implant comprising a recess extending from a proximal end of an implant body second portion. In the recess, an expandable hydrogel material is disposed. To allow fluid to be received by the hydrogel material, an orifice of the recess is left open.

In this example, the hydrogel material is configured and positioned to laterally expand out of the recess, when implanted, and into an ampulla-like region 4770 to assist retention of the lacrimal implant within the punctum. As shown, the lateral expansion of the hydrogel material urges a cap or other projection at a proximal end of the first portion flush with a punctum-like surface 4772.

Sheath Body Examples:

In various ways, the sheath body can comprise appropriate shapes and materials to control migration of drug or other therapeutic agents from a distinct drug insert or an implant body including integrated drug or other agent. In some examples, the sheath body is configured to be conformable to an implant anatomy, such as an anatomy of a lacrimal punctum or associated canaliculus. In some examples, the sheath body at least partially covers or surrounds the drug insert and can fit snugly against an outer surface of a matrix/agent mixture. In other examples, the sheath body covers or surrounds portions of an implant body including one or more integrated agents. The sheath body can be made from a material that is substantially impermeable to the drug or other therapeutic agent so that the rate of migration of the drug or agent is largely controlled by an exposed surface area of the drug insert or implant body that is not covered by the sheath body. In many examples, migration of the agents through the sheath body can be about one tenth of the migration of the agent through the exposed surface of the drug insert, or less.

Suitable sheath body materials can include, among others, polyimide, polyethylene terephthalate (PET), or parylene. The sheath body can have a thickness, as defined from the sheath surface adjacent the outer matrix/agent mixture surface to an opposing sheath surface away from the outer surface, of about 0.00025 inches to about 0.0015 inches. The total diameter of the sheath that extends across a drug insert can range from about 0.2 millimeters to about 1.2 millimeters. The drug insert can be formed by dip coating the matrix in the sheath body. In some examples, the sheath body can comprise a tube into which the matrix/agent mixture is introduced. The sheath body can also be dip coated around the matrix/agent mixture, for example dip coated around a pre-formed matrix/agent core or implant body.

The sheath body can be provided with one or more additional features such as to facilitate clinical use of the lacrimal implants discussed herein. For example, the sheath can receive a drug insert that is exchangeable in situ, while the implant body remains implanted in the patient, or after its removal. In some examples, the sheath body can be provided with one or more external protrusions that apply force to the sheath body when squeezed, which cause the matrix/agent mixture to be ejected from the sheath body. A replacement drug insert can then be positioned in the sheath body.

Therapeutic Agent Examples:

A therapeutic agent (or simply "agent") can comprise, among other things, a drug made from one or any combination of the following or their equivalents, derivatives or analogs, including, anti-glaucoma medications, (e.g. adrenergic agonists, adrenergic antagonists (beta blockers), carbonic anhydrase inhibitors (CAIs, systemic and topical), parasympathomimetics, prostaglandins and hypotensive lipids, and combinations thereof), antimicrobial agent (e.g., antibiotic, antiviral, antiparacytic, antifungal, etc.), a corticosteroid or other anti-inflammatory (e.g., an NSAID or other analgesic and pain management compounds), a decongestant (e.g., vasoconstrictor), an agent that prevents of modifies an allergic response (e.g., an antihistamine, cytokine inhibitor, leucotriene inhibitor, IgE inhibitor, immunomodulator), a mast cell stabilizer, cycloplegic, mydriatic or the like.

Example available agents include, but are not limited to, thrombin inhibitors; antithrombogenic agents; thrombolytic agents; fibrinolytic agents; vasospasm inhibitors; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluorometalone, betamethasone, triamcinolone, triamcinolone acetonide); non steroidal anti-inflammatories (NSAIDs) (such as salicylate, indomethacin, ibuprofen, diclofenac, flurbiprofen, piroxicam indomethacin, ibuprofen, naxopren, piroxicam and nabumetone). Examples of such anti-inflammatory steroids contemplated for use with the present lacrimal implants, include triamcinolone acetonide (generic name) and corticosteroids that include, for example, triamcinolone, dexamethasone, fluocinolone, cortisone, prednisolone, flumetholone, and derivatives thereof.); antiallergenics (such as sodium chromoglycate, antazoline, methapyriline, chlorpheniramine, cetrizine, pyrilamine, prophenpyridamine); anti proliferative agents (such as 1,3-cis retinoic acid, 5-fluorouracil, taxol, rapamycin, mitomycin C and cisplatin); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouracil3; immunological drugs (such as vaccines and immune stimulants); hormonal agents (such as estrogens,—estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotropin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix; components; ACE inhibitors; free radical scavengers; chelators; antioxidants; anti polymerases; photodynamic therapy agents; gene therapy agents; and other therapeutic agents such as prostaglandins, antiprostaglandin, prostaglandin precursors, including antiglaucoma drugs including beta-blockers such as Timolol, betaxolol, levobunolol, atenolol, and prostaglandin analogues such as bimatoprost, travoprost, latanoprost etc; carbonic anhydrase inhibitors such as acetazolamide, dorzolamide, brinzolamide, methazolamide, dichlorphenamide, diamox; and neuroprotectants such as lubezole, nimodipine and related compounds; and parasympathomimetrics such as pilocarpine, carbachol, physostigmine and the like.

Additional agents that can be used with the present lacrimal implants include, but are not limited to, drugs that have been approved under Section 505 of the United States Federal Food, Drug, and Cosmetic Act or under the Public Health Service Act, some of which can be found at the U.S. Food and Drug Administration (FDA) website http://www.accessdata.fda.gov/scripts/cder/drugsatfda/index. The present lacrimal implants can also be used with drugs listed in the Orange Book, either in paper or in electronic form, which can be found at the FDA Orange Book website (http://www.fda.gov/cder/ob/)), that has or records the same date as, earlier date than, or later date than, the filing date of this patent document. For example, these drugs can include, among others, dorzolamide, olopatadine, travoprost, bimatoprost, cyclosporin, brimonidine, moxifloxacin, tobramycin, brinzolamide, aciclovir timolol maleate, ketorolac tromethamine, prednisolone acetate, sodium hyaluronate, nepafenac, bromfenac, diclofenac, flurbiprofen, suprofenac, binoxan, patanol, dexamethasone/tobramycin combination, moxifloxacin, or acyclovir.

Examples of diseases or disorders that can be treated with above-listed agents include, but are not limited to, glaucoma, pre- and post-surgical ocular treatments, dry eye, anti-eye allergy, anti-infective, post-surgical inflammation or pain, respiration-related disorders, such as allergies, inner ear disorders, such as dizziness or migraines, or other systemic disorders, such as hypertension, cholesterol management, pulmonary disorders or immunological disorders. In some examples, the therapeutic agent can include a lubricant or a surfactant, for example a lubricant to treat dry eye. In other examples, the therapeutic agent can include an absorbent capable of absorbing tear from an eye.

Drug Insert Examples:

A drug insert can comprise one or more drugs or other therapeutic agents, and in some examples, one or more matrix materials to provide sustained release of the drug or other agents. Similarly, where greater amounts of agerit are desired, substantial portions of an implant body can comprise one or more integrated drugs or other agents and matrix materials configured to provide release of the agents.

The one or more drugs or other therapeutic agents can migrate from an exposed surface of the drug insert to the target tissue based, at least in part, on a solubility of the drugs or agents in the matrix. The rate of migration of the drugs or agents from the exposed surface can also be related to the concentration of drugs or agents dissolved in the matrix. In some examples, the concentration of drugs or agents dissolved in the drug insert can be controlled to provide the desired release rate of the drugs or agents. In addition or in combination, the rate of migration of drugs or agents from the exposed surface can be related to one or more properties of the matrix in which the drugs or agents dissolve, such as the properties of a silicone matrix formulation. In some examples, the drugs or agents included in the drug insert can include liquid, solid, solid gel, solid crystalline, solid amorphous, solid particulate, or dissolved forms. In one such example, liquid Latanoprost droplets or solid Bimatoprost particles are dispersed in a silicone matrix.

The drug insert can comprise one or more biocompatible materials capable of providing a sustained release of the one or more drugs or agents. Although the drug insert is primarily discussed above with respect to an example comprising a matrix including a substantially non-biodegradable silicone matrix with dissolvable inclusions of the drugs or agents located therein, the drug insert can include other structures that provide sustained release of the drugs or agents, for example a biodegradable matrix, a porous drug insert, a liquid drug insert or a solid drug insert. A matrix that includes the drugs or agents can be formed from either biodegradable or non-biodegradable polymers. In some examples, a non-biodegradable drug insert can include silicone, acrylates, polyethylenes, polyurethane, polyurethane, hydrogel, polyester (e.g., DACRON® from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, stainless steel, nickel-titanium alloy (e.g., Nitinol), titanium, stainless steel, cobalt-chrome alloy (e.g., ELGILOY® from Elgin Specialty Metals, Elgin, Ill.; CONICHROME® from Carpenter Metals Corp., Wyomissing, Pa.). In some examples, a biodegradable drug insert can comprise one or more biodegradable polymers, such as protein, hydrogel, polyglycolic acid (PGA), polylactic acid (PLA), poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid) and combinations thereof. In some examples, the drug insert can comprise a hydrogel polymer.

Closing Notes:

Among other things, lacrimal implants and related methods providing secure retention within a lacrimal punctum and canaliculus of an eye are discussed. The lacrimal implants can comprise an implant body configured for at least partial insertion through the lacrimal punctum and into the canaliculus. The implant body can include first and second portions, and can extend from a proximal end of the first portion defining a longitudinal proximal axis to a distal end of the second portion defining a longitudinal distal axis. The implant body can be configured such that, when implanted using an integral dilator, an at least 45 degree angled intersection exists between the proximal axis and the distal axis. In this way, at least a portion of the implant body can be biased against at least a portion of the lacrimal canaliculus located at or more distal to a canalicular curvature, thereby retaining an implanted position of the lacrimal implant using anatomical structures. In various examples, the lacrimal implant can further comprise a drug insert disposed in at least one of the first portion or the second portion of the implant body to provide a sustained release of a drug or other therapeutic agent to an eye, nasal passage, or inner ear system, for instance. The drug insert can include a distinct drug core disposed within an implant body cavity or can include a mixture of drug or other agent particles throughout one or more implant body portions, or both.

Advantageously, in some examples, the present lacrimal implants can successfully block the flow of tears or provide sustained delivery of a drug or other therapeutic agent to an eye, nasal passage, or inner ear for varying periods of time, such as from days to months to years. In addition, by optionally including first and second implant body cavities or drug releasing implant body portions, a dual drug or other agent releasing profile can be possible. For instance, two separate drugs can be released from two different implant locations. Further, the canalicular curve retaining configuration of the present implant body can reduce over-stretching of the lacrimal punctum and canaliculus and inadvertent fall out of implants. It is believe the present lacrimal implants can, but need not, be implemented so-as-to provide a one-size-fits-all regime, as an expandable coating or other expandable retention material can be applied to or within the implant body, such as to fit in and against hollow tissue structures of varying sizes. The expandable nature of the present lacrimal can allow for easier implantation, as some of the retention features of the implant can be activated post-implantation.

The present lacrimal implant may also be better retained within a punctum and canaliculus of a patient due to the combination of, for example, a cap-like projection at a proximal end of a first implant portion, a heel-like retainment projection at a proximal end of a second implant portion, or one or more intermediate or distally located projections on the first or second implant portions. As further discussed above, the cap-like projection may inhibit the implant wholly from migrating below the punctum and into the lacrimal canaliculus. The intermediate, distal and heel-like projections may help hold the implant in place until a caregiver physician chooses to remove it.

The above Detailed Description includes references to the accompanying drawings, which form a part of the Detailed Description. The drawings show, by way of illustration, specific embodiments in which the invention can be practiced. These embodiments are also referred to herein as "examples." All publications, patents, and other patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the term "about" is used to refer to an amount that is approximately, nearly, almost, or in the vicinity of being equal to a stated amount.

In this document, the term "proximal" refers to a location relatively closer to the cornea of an eye, and the term "distal" refers to a location relatively further from the cornea and inserted deeper into a lacrimal canaliculus.

In this document, the term "hydrogel" is used to refer to an absorbing or otherwise retaining material (e.g., adsorbing material), such as super-absorbent polymers, hydrocolloids, and water-absorbent hydrophilic polymers, for example. Examples of hydrogels for use with the present lacrimal implants include, among others, aliphatic thermoplastic polyurethanes (TPU), such as hydrophilic, aliphatic, and polyether-based thermoplastic polyurethanes. Suitable thermoplastic polyurethanes include those commercially available from the Lubrizol Corporation of Cleveland, Ohio under the trade name, Tecophilic. In certain applications, hydrogels commercially available under the trade names "Tecophilic TG-500" (or simply "TG-500") and "Tecophilic TG-2000" (or simply "TG-2000") can be utilized. The term "hydrogel" can refer to super-absorbent polymer particles in a "dry" state, such as when the hydrogel is not expanded and contains less to no water weight. The term "hydrogel" can also be used to refer to super-absorbent polymer particles in a hydrated or expanded state, more specifically, hydrogels that have absorbed at least their weight in water, such as several hundred times their weight in water (e.g., TG-500, which can absorb about 500 times its weight in water and TG-2000, which can absorb about 2000 times its weight in water). As the hydrogel material absorbs fluid, its size can increase (e.g., swell) and its shape can change to bias against, or cause a surrounding material to bias against, at least a portion of a lacrimal ampulla or lacrimal canalicular wall.

In the appended claims, the terms "including" and "in which" are used as the plain-English equivalents of the respective terms "comprising" and "wherein." Also, in the following claims, the terms "including" and "comprising" are open-ended, that is, a system, assembly, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above Detailed Description is intended to be illustrative, and not restrictive. For example, the above-described examples (or one or more features thereof) can be used in combination with each other. As an example, one or more dimensions from the various implant embodiments shown or described may be grouped together to form an implant embodiment capable of providing a desired drug concentration. Other embodiments can be used, such as by one of ordinary skill in the art upon reviewing the above description. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

What is claimed is:

1. A lacrimal implant for insertion into a lacrimal canaliculus, comprising:
   an implant body, comprising first and second portions, the implant body non-linearly extending from a proximal end portion positionable within a vertical section of the lacrimal canaliculus to a distal end portion positionable within a horizontal section of the lacrimal canaliculus and having an intermediate portion therebetween, the proximal end of the first portion defining a longitudinal proximal axis and the distal end of the second portion defining a longitudinal distal axis, the first portion including a cavity;
   an insert disposed in the cavity, the insert comprising solid agent particles dispersed in a polymeric matrix;
   the intermediate portion partially extending in a first direction toward the proximal end portion, partially extending in a second direction toward the distal end portion, and partially extending in a third direction along the longitudinal distal axis to form a retention element, configured to bias against a portion of a lacrimal canaliculus ampulla wherein the third direction is perpendicular to the first direction of the intermediate portion, such that, when implanted in the lacrimal canaliculus, the implant body directionally biases laterally against at least a portion of the lacrimal canaliculus located at or more distal to a canalicular curvature; and a graspable projection extending at least partially from the proximal end of the first portion, the graspable projection including an inward-extending retaining lip that overhangs a cavity to secure the drug insert within the cavity of the first portion, wherein the inward-extending retaining lip overhangs a proximal surface of the insert, when fully seated in the cavity, thereby securing a position of the insert, wherein the implant body inhibits fluid flow into and through the lacrimal canaliculus.

2. The lacrimal implant of claim 1, wherein the graspable projection extending at least partially from the proximal end of the first portion, is configured to seat against or near a lacrimal punctum when the implant body is implanted.

3. The lacrimal implant of claim 1, wherein the agent is a dry eye agent.

4. The lacrimal implant of claim 1, wherein the retention element comprises a flat hull-like shape.

5. The lacrimal implant of claim 1, wherein the retention element projects proximally about 0.44 millimeters from an intersection of the first and second portions of the implant body.

6. The lacrimal implant of claim 1, wherein the retention element further comprises an insertion-facilitating depression graspable by an insertion tool.

7. The lacrimal implant of claim 1, wherein an outer surface slope of the second portion is between about 1 degree to about 10 degrees with respect to the longitudinal distal axis.

8. The lacrimal implant of claim 1, wherein the first direction and second direction of the intermediate portion comprise an angle that is from about 45 degrees to about 135 degrees.

9. The lacrimal implant of claim 1, wherein the implant body comprises silicone, polyurethane or acrylic.

10. The lacrimal implant of claim 1, wherein the implant body comprises a biocompatible colorant.

11. The lacrimal implant of claim 1, wherein the graspable projection is ovoid shaped.

12. The lacrimal implant of claim 1, wherein the agent treats at least one of glaucoma, pre-surgical ocular indications, post-surgical ocular indications, dry eye, eye allergy symptoms, ocular infection, post-surgical inflammation or post-surgical pain.

13. The lacrimal implant of claim 1, wherein the agent is a lubricant or surfactant.

14. The lacrimal implant of claim 1, wherein the matrix comprises silicone, acrylate, polyethylene, polyurethane, hydrogel, polyester, polypropylene, polytetrafluoroethylene (PTFE), polyether ether ketone (PEEK), nylon, silicone rubber, polyethylene terephthalate, polycarbonate urethane, polyimide, polyglycolic acid (PGA), polylactic acid (PLA), poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoester, polyhydroxybutyrate, polyanhydride, polyphosphoester, poly(alpha-hydroxy acid) or combinations thereof.

15. A lacrimal implant insertable into a lacrimal canaliculus, comprising:

an implant body, including first and second portions, the implant body extending from a proximal end of the first portion to a distal end of the second portion, the proximal end of the first portion defining a longitudinal proximal axis and the distal end of the second portion defining a longitudinal distal axis;

the first portion including a cavity extending inward from the proximal end of the first portion, an insert disposed in the cavity of the first portion to provide a sustained agent release to an eye, wherein the insert comprises solid agent particles dispersed in a polymeric matrix having at least one exposed surface to deliver a sustained release of the agent;

a graspable projection extending at least partially from the proximal end of the first portion, the graspable projection including an inward-extending retaining lip that overhangs a cavity to secure the insert within the cavity of the first portion, wherein the inward-extending retaining lip overhangs a proximal surface of the insert, when fully seated in the cavity, thereby securing a position of the insert, wherein a proximal end of the second portion comprises a retention element configured to bias against a portion of a lacrimal canaliculus ampulla; and the implant body configured such that, when implanted in the lacrimal canaliculus, an angled intersection exists between the proximal axis and the distal axis for biasing at least a portion of the implant body against at least a portion of the lacrimal canaliculus located at or more distal to a canalicular curvature.

16. The lacrimal implant of claim 15, wherein the matrix comprises silicone, acrylate, polyethylene, polyurethane, hydrogel, polyester, polypropylene, polytetrafluoroethylene (PTFE), expanded PTFE (ePTFE), polyether ether ketone (PEEK), nylon, silicone rubber, polyethylene terephthalate, polycarbonate urethane, polyimide, polyglycolic acid (PGA), polylactic acid (PLA), poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoester, polyhydroxybutyrate, polyanhydride, polyphosphoester, poly(alpha-hydroxy acid) or combinations thereof.

17. The lacrimal implant of claim 15, wherein the agent is a lubricant or surfactant.

18. The lacrimal implant of claim 15, wherein the implant body comprises silicone, polyurethane or acrylic.

19. An agent delivery system for insertion into a lacrimal canaliculus of a patient, comprising:

a lacrimal insert of claim 1, wherein the agent treats at least one of glaucoma, pre-surgical ocular indications, post-surgical ocular indications, dry eye, eye allergy symptoms, ocular infection, post-surgical inflammation or post-surgical pain.

20. The agent delivery system of claim 19, wherein the agent is a lubricant or surfactant.

* * * * *